(12) United States Patent
Chambon et al.

(10) Patent No.: US 7,112,715 B2
(45) Date of Patent: Sep. 26, 2006

(54) TRANSGENIC MOUSE FOR TARGETED RECOMBINATION MEDIATED BY MODIFIED CRE-ER

(75) Inventors: Pierre Chambon, Blaesheim (FR); Daniel Metzger, Strasbourg (FR)

(73) Assignee: Gie-Cerbm, Centre Europeen de Recherche en Biologie et en Medecine (GIE), Illkirch (FR)

( * ) Notice: Subject to any disclaimer, the term of this patent is extended or adjusted under 35 U.S.C. 154(b) by 130 days.

(21) Appl. No.: 09/853,033

(22) Filed: May 11, 2001

(65) Prior Publication Data
US 2002/0100068 A1   Jul. 25, 2002

(30) Foreign Application Priority Data
Oct. 3, 2000   (FR)   .................... 00 12570

(51) Int. Cl.
 *G01N 33/00*   (2006.01)
(52) U.S. Cl. ................ 800/3; 800/18; 800/21
(58) Field of Classification Search .............. 800/3, 800/18, 22; 530/350
See application file for complete search history.

(56) References Cited

U.S. PATENT DOCUMENTS 6,093,873 A   7/2000   Chambon et al.

FOREIGN PATENT DOCUMENTS

| EP | 0 698 392 A | 2/1996 |
| WO | WO 92 06104 A | 4/1992 |
| WO | WO 94 26100 A | 11/1994 |
| WO | WO 95 00555 A | 1/1995 |
| WO | WO 97 10819 A | 3/1997 |
| WO | WO 97 31108 A | 8/1997 |
| WO | WO 99 18222 A | 4/1999 |
| WO | WO 99 25851 A | 5/1999 |
| WO | WO 00 49147 A | 8/2000 |

OTHER PUBLICATIONS

Campbell and Wilmut. Totipotency or Multipotentiality of Cultured Cells: Applications and Progress. Theriogenology. Jan. 1, 1997. Vol. 47, No. 1, pp. 63-70.*
Jacks et al. Effects of an Rb mutation in the mouse. Sep. 24, 1992. Nature. vol. 359, pp. 295-300.*
Bradley et al. Modifying the Mouse: Design Desire. May 1992. Biotechnology. vol. 10, pp. 534-539.*
Mullins and Mullins. Perspective Series: Molecular Medicine in Genetically Engineered Animals. Apr. 1, 1996. Clinical Investigation. vol. 97, No. 7, pp. 1557-1560.I*
Sigmund. Viewpoint: Are Studies in Genetically Altered mice Out of Control? Jun. 2000. Arterioscler Thromb. Vasc. Biol. vol. 20. pp. 1425-1429.*
Wall. Transgenic Livestock: Progress and Prospects for the Future. 1996. Theriogenology. vol. 45, pp. 57-68.*
Indra et al. Nucleic Acid Research, 1999. vol. 27, p. 4324-4327.*
Feil et al. PNAS, 1996, vol. 93, pp. 10887-10890.*
Schwenk et al. Nucleic Acid Research, 1998. vol. 26, p. 1427-1432.*
Ross et al. PNAS, 1990. vol. 87, p. 9590-9594.*
Tontonoz et al. PNAS, 1997, vol. 94, pp. 237-241.*
Indra A. et al., Temporally-controlled site-specific mutagenesis in the basal layer of the epidermis: comparison of the recombinase activity of the tamoxifen-inducible Cre-ER(T) and Cre-ER(T2) recombinases, Nucleic Acids Research, Nov. 15, 1999, pp. 4324-4327, vol. 27, No. 22, Oxford University Press, Surrey, GB.
Vasioukhin V. et al., The magical touch: Genome targeting in epidermal stem cells induced by tamoxifen application to mouse skin, Proceedings of the National Academy of Sciences of USA, Jul. 20, 1999, pp. 8551-8556, vol. 96, No. 15.
Raghavan S. et al., Conditional ablation of betal integrin in skin. Severe defects in epidermal proliferation, basement membrane formation, and hair follicle invagination, The Journal of Cell Biology, Sep. 4, 2000, pp. 1149-1160, vol. 150, No. 5.
Feng X. et al., Suprabasal expression of a dominant-negative RXR alpha mutant in transgenic mouse epidermis impairs regulation of gene transcription and basal keratinocyte proliferation by RAR-selective retinoids, Genes & Development, 1997, pp. 59-71, vol. 11, No. 1.
Saltou M. et al., Inhibition of skin development by targeted expression of a dominant-negative retinoic acid receptor, Nature, Mar. 9, 1995, pp. 159-162, vol. 374, MacMillan Journals Ltd., London, GB.
Li M. et al., Skin abnormalities generated by temporally controlled RXRalpha mutations in mouse epidermis, Nature, Oct. 5, 2000, pp. 633-636, vol. 407, No. 6804.
Kastner P. et al., Vitamin A deficiency and mutations of RXRalpha, RXRbeta and RARalpha lead to early differentiation of embryonic ventricular cardiomyocytes, Development, Dec. 1997, pp. 4749-4758, vol. 124, No. 23.
Sumi-Ichinose C. et al., SNF2beta-BRG1 is essential for the viability of F9 murine embryonal carcinoma cells, Mol. Cell Biol., Oct. 1997, pp. 5976-5986, vol. 17, No. 10.
Feil R. et al., Regulation of Cre recombinase activity by mutated estrogen receptor ligand-binding domains, Biochemical and Biophysical Research Communications, Aug. 28, 1997, pp. 752-757, vol. 237, No. 3.

(Continued)

*Primary Examiner*—Celine Qian
(74) *Attorney, Agent, or Firm*—Foley & Lardner LLP

(57) ABSTRACT

The present invention relates to a metazoan organism, with the exception of humans, and in particular a mouse, characterized in that at least one cell of this organism comprises at least one fusion protein between a recombinase Cre and a modified ligand binding domain of the nuclear estrogen receptor alpha, allowing the inactive fused recombinase to be induced by synthetic antiestrogens, but not by natural estrogens, and one or more DNA sequences of interest belonging to the genome of said organism into which one or more sites of recognition of said recombinase protein are inserted. The invention also covers the methods using said organism for the screening of medicaments, the mutagenesis and the analysis of the biological function of the DNA sequences) of interest, in particular of gene(s) of interest, such as $RXR_\alpha$.

14 Claims, 21 Drawing Sheets

OTHER PUBLICATIONS

Figure 1A:
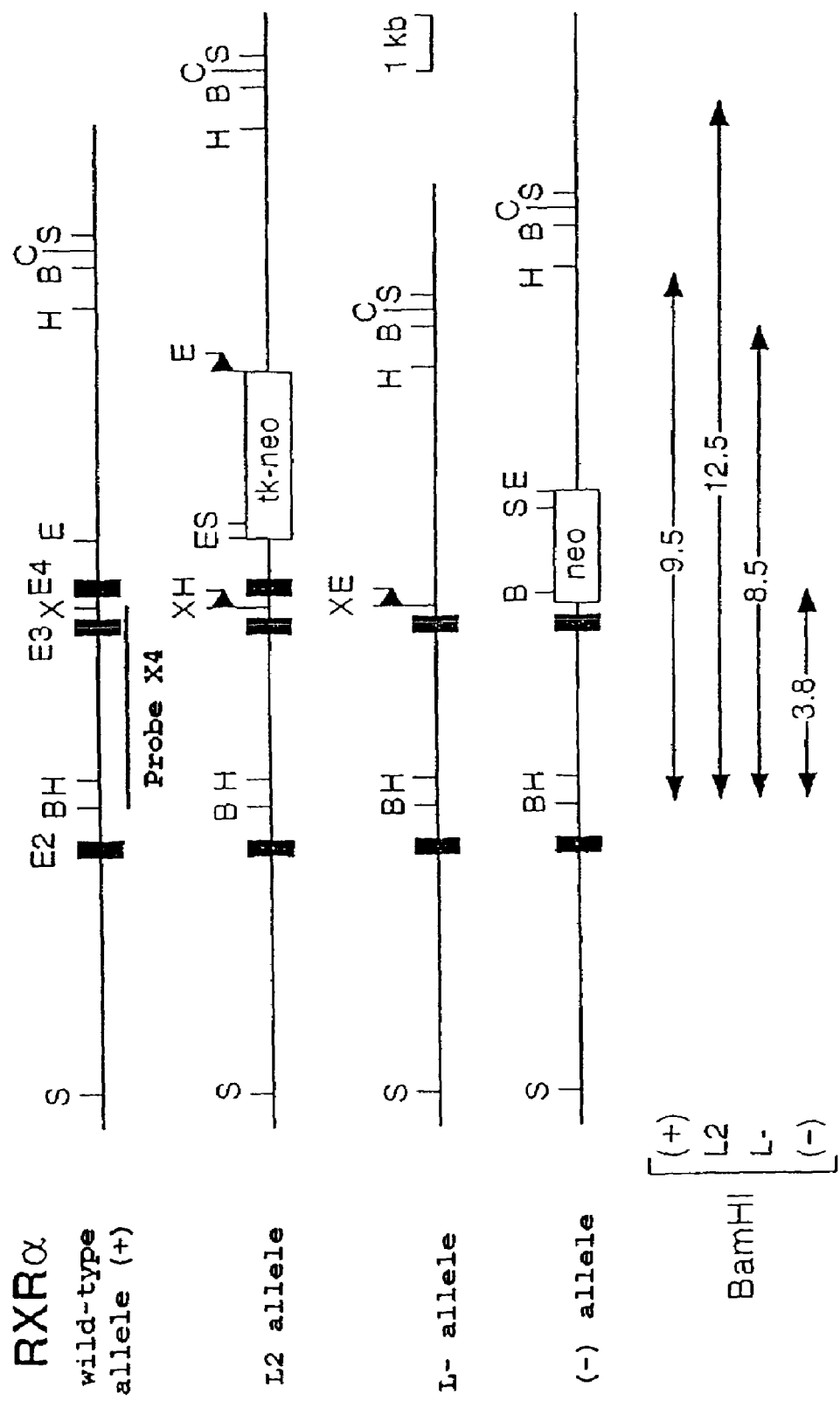

Metzger D. et al., Conditional site-specific recombination in mammalian cells using a ligand-dependent chimeric Cre recombinase, Proceedings of the National Academy of Sciences of USA, Jul. 18, 1995, pp. 6991-6995, vol. 92, No. 15, National Academy of Science, Washington, USA.

Metzger D. et al., Engineering the mouse genome by site-specific recombination, Current Opinion in Biotechnology, Oct. 1999, pp. 470-476, vol. 10, No. 5, London, GB.

Barlow C. et al., Targeted expression of Cre recombinase to adipose tissue of transgenic mice directs adipose-specific excision of loxP-flanked gene segments, Nucleic Acids Research, 1997, pp. 2543-2545, vol. 25, No. 12.

Imai T. et al., Impaired adipogenesis and lipolysis in the mouse upon selective ablation of the retinoid X receptor alpha mediated by a tamoxifen-inducible chimeric Cre recombinase (Cre-ERT2) in adipocytes, Proceedings of the National Academy of Sciences of USA, Jan. 2, 2001, pp. 224-228, vol. 98, No. 1, USA.

Imai T. et al., Inducible site-specific somatic mutagenesis in mouse hepatocytes, Genesis, Feb. 2000, pp. 147-148, No. 2, Wiley-Liss, New York, NY, US.

Wan Y. et al., Hepatocyte-specific mutation established retinoid X receptor alpha as a heterodimeric integrator of multiple physiological processes in the liver, Mol. Cell Biol., Jun. 2000, pp. 4436-4444, vol. 20, No. 12.

Mahfoudi A. et al., Specific mutations in the estrogen receptor change the properties of antiestrogens to full agonists, Proceedings of the National Academy of Sciences of the United States, 1995, pp. 4206-4210, vol. 92, No. 10.

* cited by examiner

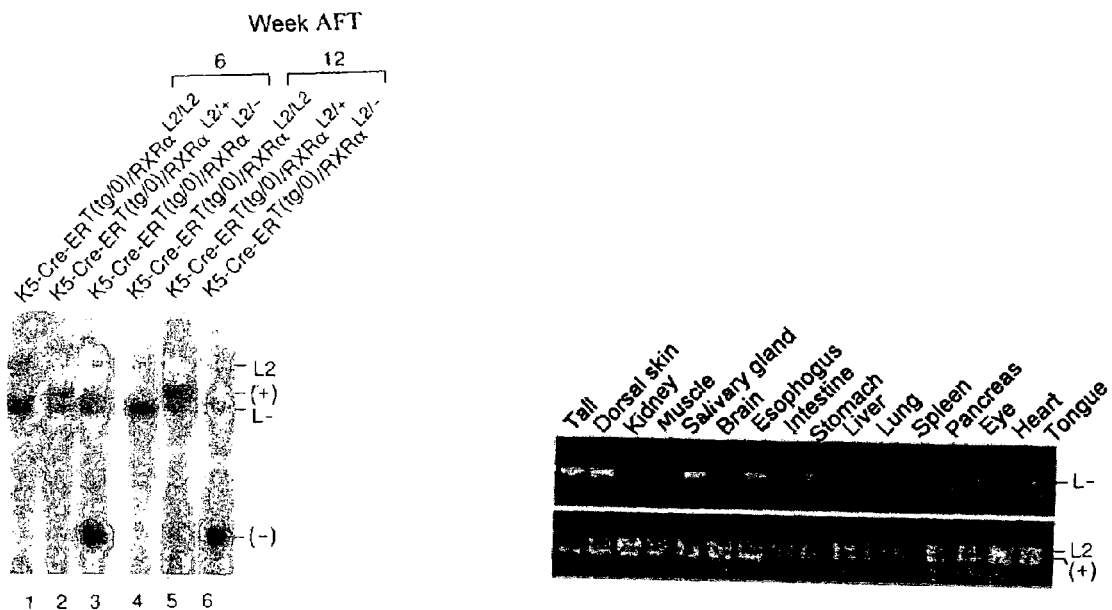
FIG. 1B
FIG. 1C
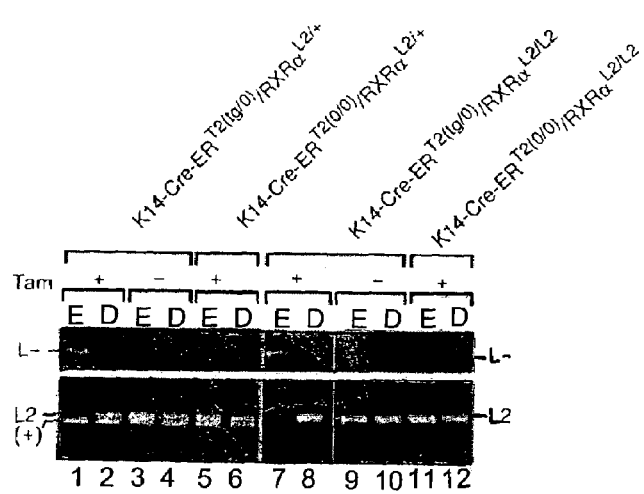
FIG. 1D

A
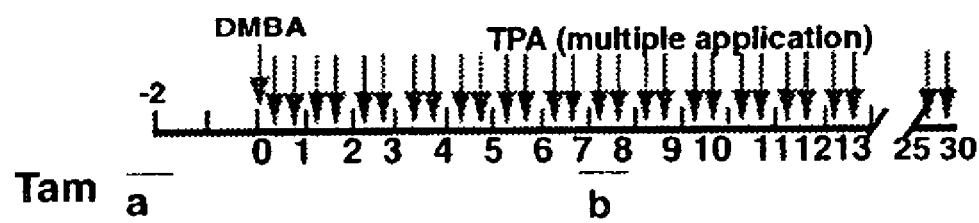
B
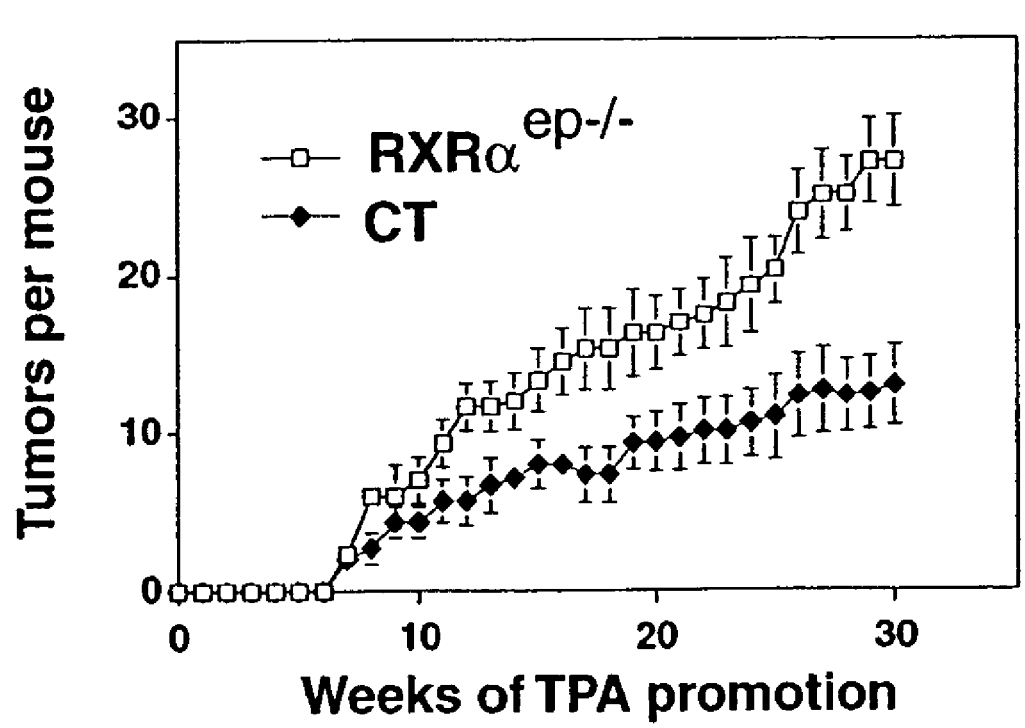
FIG. 12A-B

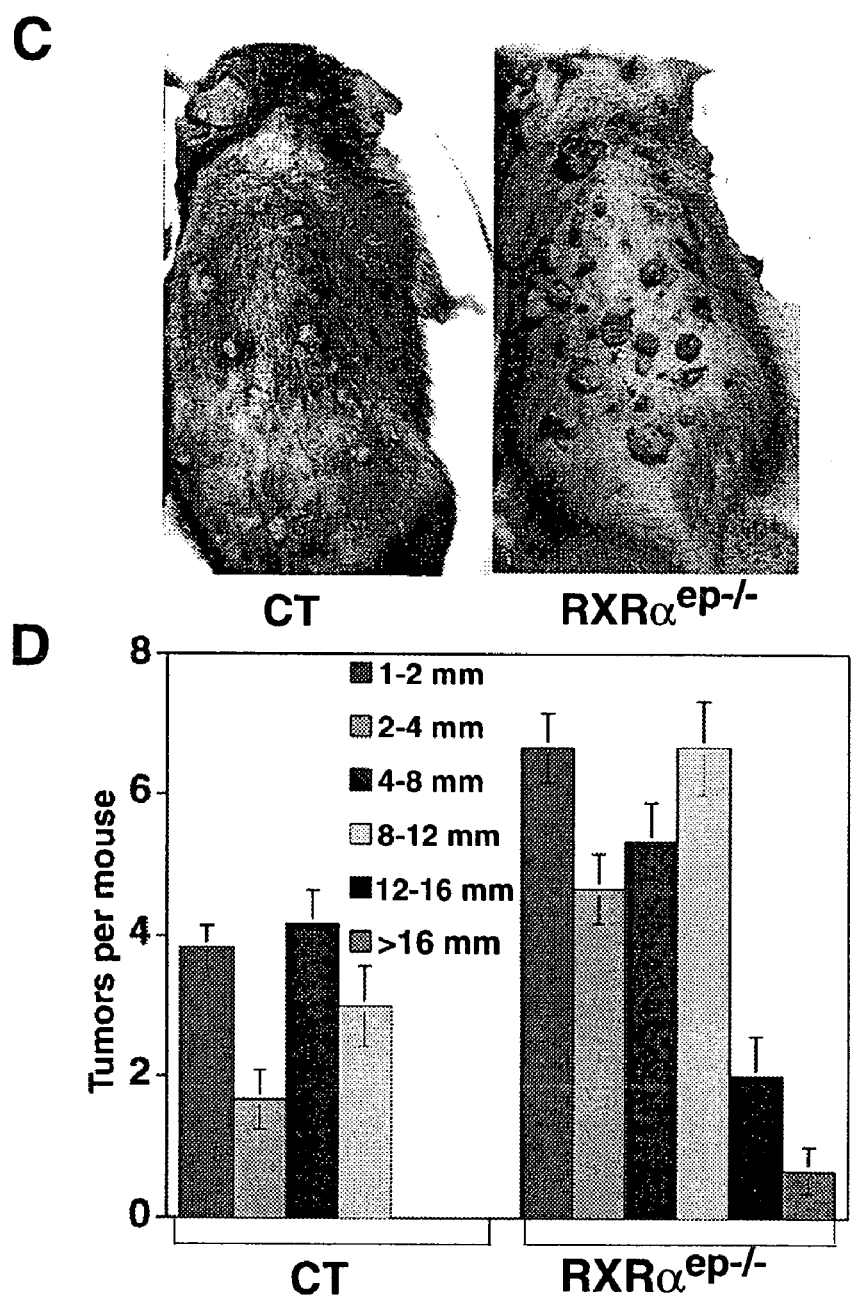
FIG. 12C-D

A
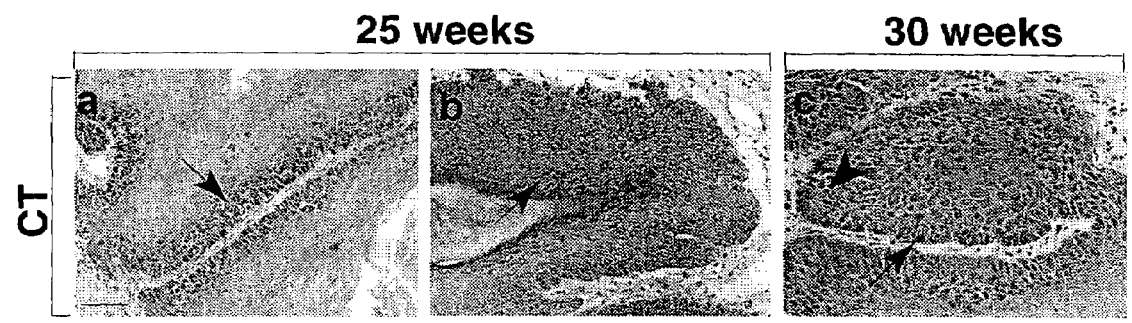
B
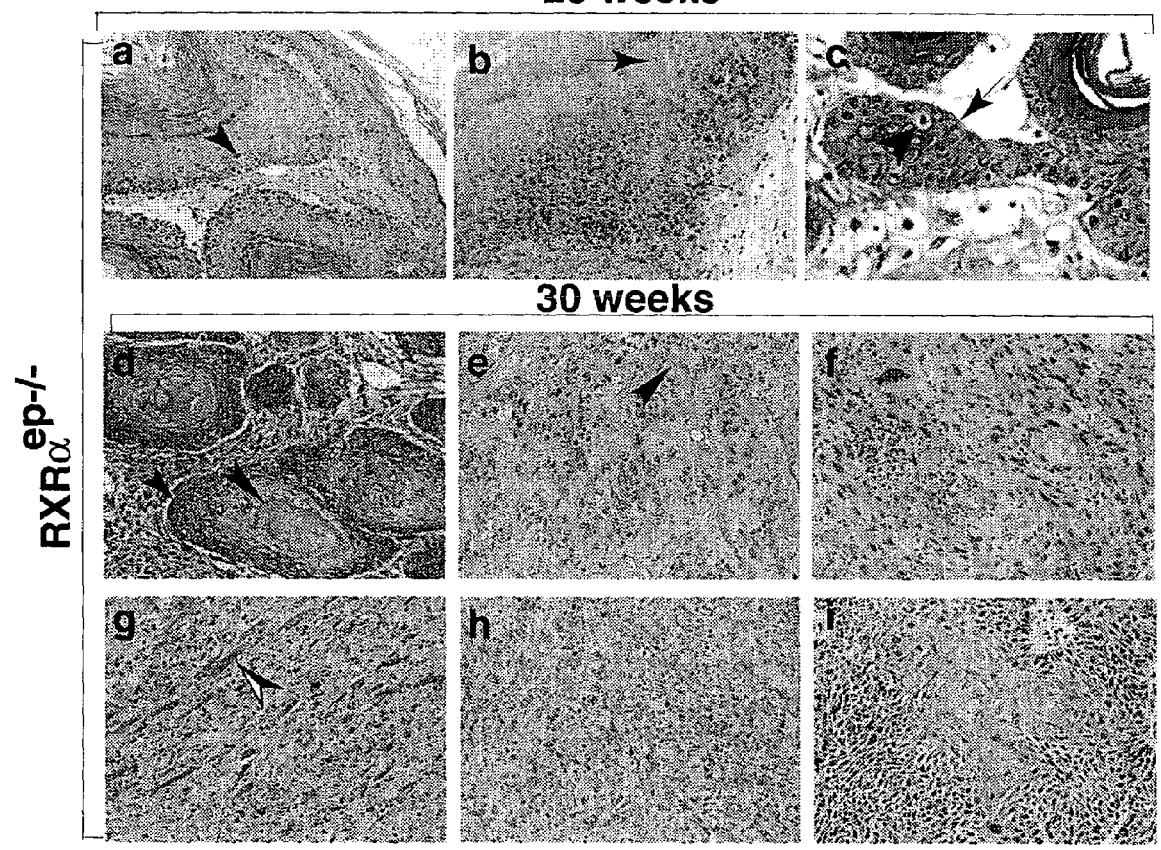
FIG. 13A-B

Histological analysis of paraffin sections (5 μm-thick) of biopsies of 8-16 mm tumors from CT and RXRα ep-/- mice, 25 and 30 weeks after the start of the DMBA/TPA treatment

| | Weeks of DMBA/TPA treatment | number of tumors analysed | benign papillomas | In situ carcinoma | Papillomas exhibiting | | | | | | |
|---|---|---|---|---|---|---|---|---|---|---|---|
| | | | | | FC | SCC (I) | SCC (II) | SCC(III) | SCC (IV) | SpCC | BCC |
| CT mice | 25 | 20 | 19 (95 %) | 1 (5%) | 0 | 0 | 0 | 0 | 0 | 0 | 0 |
| | 30 | 31 | 25 (80 %) | 1 (~3%) | 5 (~16%) | 0 | 0 | 0 | 0 | 0 | 0 |
| RXRα ep-/- mice | 25 | 20 | 10 (50 %) | 2 (10%) | 8 (40%) | 0 | 0 | 0 | 0 | 0 | 0 |
| | 30 | 35 | 13 (37 %) | 1 (~3%) | 7 (20%) | 3 (~9%) | 3 (~9%) | 1 (~3%) | 2 (~6%) | 2 (~6%) | 3 (~9%) |

FC, focal carcinoma; SCC, squamous cell carcinoma; SpCC, spindle cell carcinoma; BCC, basal cell carcinoma

FIG. 13C

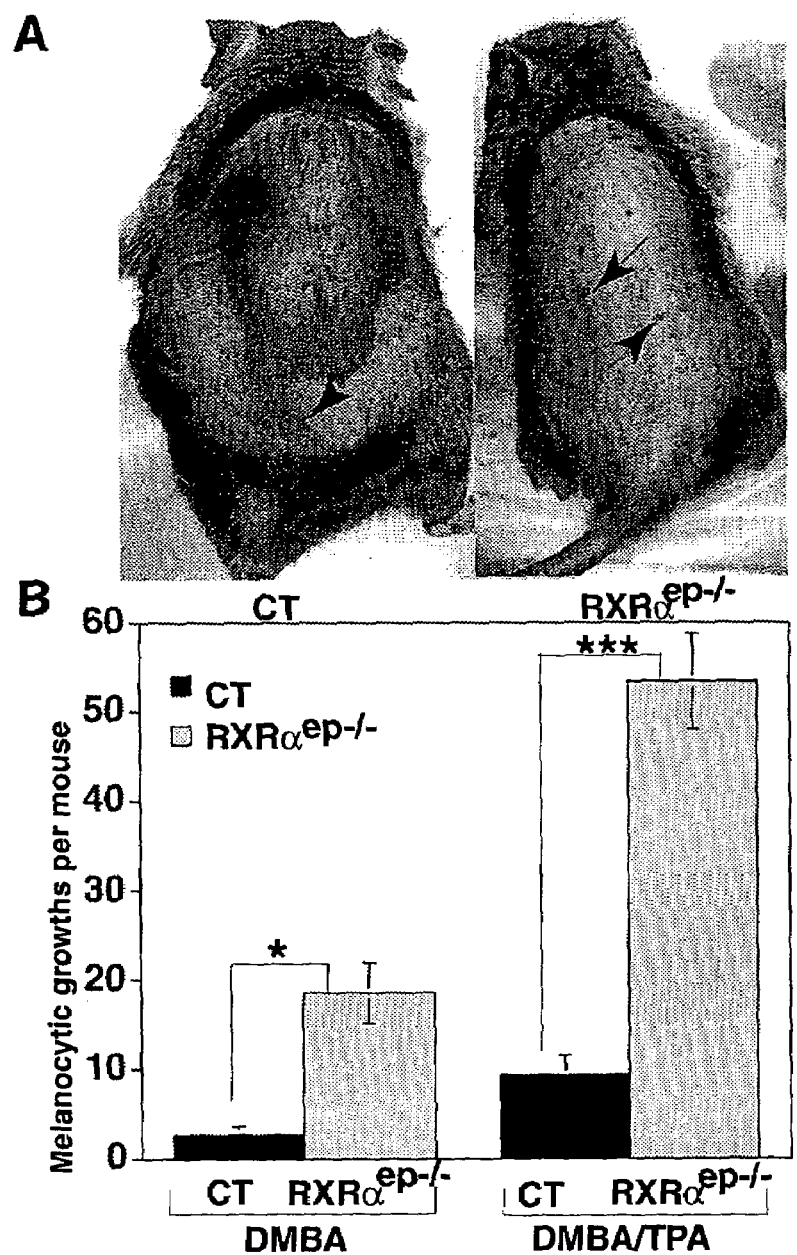
FIG. 14A-B

SEQUENCE LISTING

```
<160> NUMBER OF SEQ ID NOS: 14

<210> SEQ ID NO 1
<211> LENGTH: 1788
<212> TYPE: DNA
<213> ORGANISM: Homo sapiens
<220> FEATURE:
<221> NAME/KEY: CDS
<222> LOCATION: (1)..(1788)

<400> SEQUENCE: 1 atg acc atg acc ctc cac acc aaa gca tct ggg atg gcc cta ctg cat      48
Met Thr Met Thr Leu His Thr Lys Ala Ser Gly Met Ala Leu Leu His
  1               5                  10                  15 cag atc caa ggg aac gag ctg gag ccc ctg aac cgt ccg cag ctc aag      96
Gln Ile Gln Gly Asn Glu Leu Glu Pro Leu Asn Arg Pro Gln Leu Lys
             20                  25                  30 atc ccc ctg gag cgg ccc ctg ggc gag gtg tac ctg gac agc agc aag     144
Ile Pro Leu Glu Arg Pro Leu Gly Glu Val Tyr Leu Asp Ser Ser Lys
         35                  40                  45 ccc gcc gtg tac aac tac ccc gag ggc gcc gcc tac gag ttc aac gcc     192
Pro Ala Val Tyr Asn Tyr Pro Glu Gly Ala Ala Tyr Glu Phe Asn Ala
     50                  55                  60 gcg gcc gcc gcc aac gcg cag gtc tac ggt cag acc ggc ctc ccc tac     240
Ala Ala Ala Ala Asn Ala Gln Val Tyr Gly Gln Thr Gly Leu Pro Tyr
 65                  70                  75                  80 ggc ccc ggg tct gag gct gcg gcg ttc ggc tcc aac ggc ctg ggg ggt     288
Gly Pro Gly Ser Glu Ala Ala Ala Phe Gly Ser Asn Gly Leu Gly Gly
                 85                  90                  95 ttc ccc cca ctc aac agc gtg tct ccg agc ccg ctg atg cta ctg cac     336
Phe Pro Pro Leu Asn Ser Val Ser Pro Ser Pro Leu Met Leu Leu His
            100                 105                 110
```

```
                                                     -continued ccg ccg ccg cag ctg tcg cct ttc ctg cag ccc cac ggc cag cag gtg        384
Pro Pro Pro Gln Leu Ser Pro Phe Leu Gln Pro His Gly Gln Gln Val
        115                 120                 125 ccc tac tac ctg gag aac gag ccc agc ggc tac acg gtg cgc gag gcc        432
Pro Tyr Tyr Leu Glu Asn Glu Pro Ser Gly Tyr Thr Val Arg Glu Ala
130                 135                 140 ggc ccg ccg gca ttc tac agg cca aat tca gat aat cga cgc cag ggt        480
Gly Pro Pro Ala Phe Tyr Arg Pro Asn Ser Asp Asn Arg Arg Gln Gly
145                 150                 155                 160 ggc aga gaa aga ttg gcc agt acc aat gac aag gga agt atg gct atg        528
Gly Arg Glu Arg Leu Ala Ser Thr Asn Asp Lys Gly Ser Met Ala Met
            165                 170                 175 gaa tct gcc aag gag act cgc tac tgt gca gtg tgc aat gac tat gct        576
Glu Ser Ala Lys Glu Thr Arg Tyr Cys Ala Val Cys Asn Asp Tyr Ala
        180                 185                 190 tca ggc tac cat tat gga gtc tgg tcc tgt gag ggc tgc aag gcc ttc        624
Ser Gly Tyr His Tyr Gly Val Trp Ser Cys Glu Gly Cys Lys Ala Phe
    195                 200                 205 ttc aag aga agt att caa gga cat aac gac tat atg tgt cca gcc acc        672
Phe Lys Arg Ser Ile Gln Gly His Asn Asp Tyr Met Cys Pro Ala Thr
210                 215                 220 aac cag tgc acc att gat aaa aac agg agg aag agc tgc cag gcc tgc        720
Asn Gln Cys Thr Ile Asp Lys Asn Arg Arg Lys Ser Cys Gln Ala Cys
225                 230                 235                 240 cgg ctc cgc aaa tgc tac gaa gtg gga atg atg aaa ggt ggg ata cga        768
Arg Leu Arg Lys Cys Tyr Glu Val Gly Met Met Lys Gly Gly Ile Arg
            245                 250                 255 aaa gac cga aga gga ggg aga atg ttg aaa cac aag cgc cag aga gat        816
Lys Asp Arg Arg Gly Gly Arg Met Leu Lys His Lys Arg Gln Arg Asp
        260                 265                 270 gat ggg gag ggc agg ggt gaa gtg ggg tct gct gga gac atg aga gct        864
Asp Gly Glu Gly Arg Gly Glu Val Gly Ser Ala Gly Asp Met Arg Ala
    275                 280                 285 gcc aac ctt tgg cca agc ccg ctc atg atc aaa cgc tct aag aag aac        912
Ala Asn Leu Trp Pro Ser Pro Leu Met Ile Lys Arg Ser Lys Lys Asn
290                 295                 300 agc ctg gcc ttg tcc ctg acg gcc gac cag atg gtc agt gcc ttg ttg        960
Ser Leu Ala Leu Ser Leu Thr Ala Asp Gln Met Val Ser Ala Leu Leu
305                 310                 315                 320 gat gct gag ccc ccc ata ctc tat tcc gag tat gat cct acc aga ccc       1008
Asp Ala Glu Pro Pro Ile Leu Tyr Ser Glu Tyr Asp Pro Thr Arg Pro
            325                 330                 335 ttc agt gaa gct tcg atg atg ggc tta ctg acc aac ctg gca gac agg       1056
Phe Ser Glu Ala Ser Met Met Gly Leu Leu Thr Asn Leu Ala Asp Arg
        340                 345                 350 gag ctg gtt cac atg atc aac tgg gcg aag agg gtg cca ggc ttt gtg       1104
Glu Leu Val His Met Ile Asn Trp Ala Lys Arg Val Pro Gly Phe Val
    355                 360                 365 gat ttg acc ctc cat gat cag gtc cac ctt cta gaa tgt gcc tgg cta       1152
Asp Leu Thr Leu His Asp Gln Val His Leu Leu Glu Cys Ala Trp Leu
370                 375                 380 gag atc ctg atg att ggt ctc gtc tgg cgc tcc atg gag cac cca ggg       1200
Glu Ile Leu Met Ile Gly Leu Val Trp Arg Ser Met Glu His Pro Gly
385                 390                 395                 400 aag cta ctg ttt gct cct aac ttg ctc ttg gac agg aac cag gga aaa       1248
Lys Leu Leu Phe Ala Pro Asn Leu Leu Leu Asp Arg Asn Gln Gly Lys
            405                 410                 415 tgt gta gag ggc atg gtg gag atc ttc gac atg ctg ctg gct aca tca       1296
Cys Val Glu Gly Met Val Glu Ile Phe Asp Met Leu Leu Ala Thr Ser
```

```
                420             425             430
tct cgg ttc cgc atg atg aat ctg cag gga gag gag ttt gtg tgc ctc    1344
Ser Arg Phe Arg Met Met Asn Leu Gln Gly Glu Glu Phe Val Cys Leu
        435             440             445 aaa tct att att ttg ctt aat tct gga gtg tac aca ttt ctg tcc agc    1392
Lys Ser Ile Ile Leu Leu Asn Ser Gly Val Tyr Thr Phe Leu Ser Ser
        450             455             460 acc ctg aag tct ctg gaa gag aag gac cat atc cac cga gtc ctg gac    1440
Thr Leu Lys Ser Leu Glu Glu Lys Asp His Ile His Arg Val Leu Asp
465             470             475             480 aag atc aca gac act ttg atc cac ctg atg gcc aag gca ggc ctg acc    1488
Lys Ile Thr Asp Thr Leu Ile His Leu Met Ala Lys Ala Gly Leu Thr
                485             490             495 ctg cag cag cag cac cag cgg ctg gcc cag ctc ctc ctc atc ctc tcc    1536
Leu Gln Gln Gln His Gln Arg Leu Ala Gln Leu Leu Leu Ile Leu Ser
        500             505             510 cac atc agg cac atg agt aac aaa ggc atg gag cat ctg tac agc atg    1584
His Ile Arg His Met Ser Asn Lys Gly Met Glu His Leu Tyr Ser Met
        515             520             525 aag tgc aag aac gtg gtg ccc ctc tat gac ctg ctg ctg gag atg ctg    1632
Lys Cys Lys Asn Val Val Pro Leu Tyr Asp Leu Leu Leu Glu Met Leu
530             535             540 gac gcc cac cgc cta cat gcg ccc act agc cgt gga ggg gca tcc gtg    1680
Asp Ala His Arg Leu His Ala Pro Thr Ser Arg Gly Gly Ala Ser Val
545             550             555             560 gag gag acg gac caa agc cac ttg gcc act gcg ggc tct act tca tcg    1728
Glu Glu Thr Asp Gln Ser His Leu Ala Thr Ala Gly Ser Thr Ser Ser
                565             570             575 cat tcc ttg caa aag tat tac atc acg ggg gag gca gag ggt ttc cct    1776
His Ser Leu Gln Lys Tyr Tyr Ile Thr Gly Glu Ala Glu Gly Phe Pro
        580             585             590 gcc aca gtc tga                                                    1788
Ala Thr Val
        595

<210> SEQ ID NO 2
<211> LENGTH: 595
<212> TYPE: PRT
<213> ORGANISM: Homo sapiens

<400> SEQUENCE: 2

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
```

-continued

```
            130                 135                 140
Gly Pro Pro Ala Phe Tyr Arg Pro Asn Ser Asp Asn Arg Arg Gln Gly
145                 150                 155                 160
Gly Arg Glu Arg Leu Ala Ser Thr Asn Asp Lys Gly Ser Met Ala Met
                    165                 170                 175
Glu Ser Ala Lys Glu Thr Arg Tyr Cys Ala Val Cys Asn Asp Tyr Ala
                    180                 185                 190
Ser Gly Tyr His Tyr Gly Val Trp Ser Cys Glu Gly Cys Lys Ala Phe
                    195                 200                 205
Phe Lys Arg Ser Ile Gln Gly His Asn Asp Tyr Met Cys Pro Ala Thr
210                 215                 220
Asn Gln Cys Thr Ile Asp Lys Asn Arg Arg Lys Ser Cys Gln Ala Cys
225                 230                 235                 240
Arg Leu Arg Lys Cys Tyr Glu Val Gly Met Met Lys Gly Gly Ile Arg
                    245                 250                 255
Lys Asp Arg Arg Gly Gly Arg Met Leu Lys His Lys Arg Gln Arg Asp
                    260                 265                 270
Asp Gly Glu Gly Arg Gly Glu Val Gly Ser Ala Gly Asp Met Arg Ala
                    275                 280                 285
Ala Asn Leu Trp Pro Ser Pro Leu Met Ile Lys Arg Ser Lys Lys Asn
290                 295                 300
Ser Leu Ala Leu Ser Leu Thr Ala Asp Gln Met Val Ser Ala Leu Leu
305                 310                 315                 320
Asp Ala Glu Pro Pro Ile Leu Tyr Ser Glu Tyr Asp Pro Thr Arg Pro
                    325                 330                 335
Phe Ser Glu Ala Ser Met Met Gly Leu Leu Thr Asn Leu Ala Asp Arg
                    340                 345                 350
Glu Leu Val His Met Ile Asn Trp Ala Lys Arg Val Pro Gly Phe Val
                    355                 360                 365
Asp Leu Thr Leu His Asp Gln Val His Leu Leu Glu Cys Ala Trp Leu
                    370                 375                 380
Glu Ile Leu Met Ile Gly Leu Val Trp Arg Ser Met Glu His Pro Gly
385                 390                 395                 400
Lys Leu Leu Phe Ala Pro Asn Leu Leu Leu Asp Arg Asn Gln Gly Lys
                    405                 410                 415
Cys Val Glu Gly Met Val Glu Ile Phe Asp Met Leu Leu Ala Thr Ser
                    420                 425                 430
Ser Arg Phe Arg Met Met Asn Leu Gln Gly Glu Glu Phe Val Cys Leu
                    435                 440                 445
Lys Ser Ile Ile Leu Leu Asn Ser Gly Val Tyr Thr Phe Leu Ser Ser
450                 455                 460
Thr Leu Lys Ser Leu Glu Glu Lys Asp His Ile His Arg Val Leu Asp
465                 470                 475                 480
Lys Ile Thr Asp Thr Leu Ile His Leu Met Ala Lys Ala Gly Leu Thr
                    485                 490                 495
Leu Gln Gln Gln His Gln Arg Leu Ala Gln Leu Leu Ile Leu Ser
                    500                 505                 510
His Ile Arg His Met Ser Asn Lys Gly Met Glu His Leu Tyr Ser Met
                    515                 520                 525
Lys Cys Lys Asn Val Val Pro Leu Tyr Asp Leu Leu Leu Glu Met Leu
530                 535                 540
Asp Ala His Arg Leu His Ala Pro Thr Ser Arg Gly Gly Ala Ser Val
545                 550                 555                 560
```

```
Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
        595

<210> SEQ ID NO 3
<211> LENGTH: 1983
<212> TYPE: DNA
<213> ORGANISM: Artificial sequence
<220> FEATURE:
<221> NAME/KEY: CDS
<222> LOCATION: (1)..(1983)
<223> OTHER INFORMATION: Description of Artificial Sequence: Chimeric
      sequence Homosapiens-Bacteriophage P1

<400> SEQUENCE: 3 atg tcc aat tta ctg acc gta cac caa aat ttg cct gca tta ccg gtc    48
Met Ser Asn Leu Leu Thr Val His Gln Asn Leu Pro Ala Leu Pro Val
  1               5                  10                  15 gat gca acg agt gat gag gtt cgc aag aac ctg atg gac atg ttc agg    96
Asp Ala Thr Ser Asp Glu Val Arg Lys Asn Leu Met Asp Met Phe Arg
             20                  25                  30 gat cgc cag gcg ttt tct gag cat acc tgg aaa atg ctt ctg tcc gtt   144
Asp Arg Gln Ala Phe Ser Glu His Thr Trp Lys Met Leu Leu Ser Val
         35                  40                  45 tgc cgg tcg tgg gcg gca tgg tgc aag ttg aat aac cgg aaa tgg ttt   192
Cys Arg Ser Trp Ala Ala Trp Cys Lys Leu Asn Asn Arg Lys Trp Phe
     50                  55                  60 ccc gca gaa cct gaa gat gtt cgc gat tat ctt cta tat ctt cag gcg   240
Pro Ala Glu Pro Glu Asp Val Arg Asp Tyr Leu Leu Tyr Leu Gln Ala
 65                  70                  75                  80 cgc ggt ctg gca gta aaa act atc cag caa cat ttg ggc cag cta aac   288
Arg Gly Leu Ala Val Lys Thr Ile Gln Gln His Leu Gly Gln Leu Asn
                 85                  90                  95 atg ctt cat cgt cgg tcc ggg ctg cca cga cca agt gac agc aat gct   336
Met Leu His Arg Arg Ser Gly Leu Pro Arg Pro Ser Asp Ser Asn Ala
            100                 105                 110 gtt tca ctg gtt atg cgg cgg atc cga aaa gaa aac gtt gat gcc ggt   384
Val Ser Leu Val Met Arg Arg Ile Arg Lys Glu Asn Val Asp Ala Gly
        115                 120                 125 gaa cgt gca aaa cag gct cta gcg ttc gaa cgc act gat ttc gac cag   432
Glu Arg Ala Lys Gln Ala Leu Ala Phe Glu Arg Thr Asp Phe Asp Gln
    130                 135                 140 gtt cgt tca ctc atg gaa aat agc gat cgc tgc cag gat ata cgt aat   480
Val Arg Ser Leu Met Glu Asn Ser Asp Arg Cys Gln Asp Ile Arg Asn
145                 150                 155                 160 ctg gca ttt ctg ggg att gct tat aac acc ctg tta cgt ata gcc gaa   528
Leu Ala Phe Leu Gly Ile Ala Tyr Asn Thr Leu Leu Arg Ile Ala Glu
                165                 170                 175 att gcc agg atc agg gtt aaa gat atc tca cgt act gac ggt ggg aga   576
Ile Ala Arg Ile Arg Val Lys Asp Ile Ser Arg Thr Asp Gly Gly Arg
            180                 185                 190 atg tta atc cat att ggc aga acg aaa acg ctg gtt agc acc gca ggt   624
Met Leu Ile His Ile Gly Arg Thr Lys Thr Leu Val Ser Thr Ala Gly
        195                 200                 205 gta gag aag gca ctt agc ctg ggg gta act aaa ctg gtc gag cga tgg   672
Val Glu Lys Ala Leu Ser Leu Gly Val Thr Lys Leu Val Glu Arg Trp
    210                 215                 220
```

-continued

| | | |
|---|---|---|
| att tcc gtc tct ggt gta gct gat gat ccg aat aac tac ctg ttt tgc<br>Ile Ser Val Ser Gly Val Ala Asp Asp Pro Asn Asn Tyr Leu Phe Cys<br>225                         230                         235                   240 | 720 | |
| cgg gtc aga aaa aat ggt gtt gcc gcg cca tct gcc acc agc cag cta<br>Arg Val Arg Lys Asn Gly Val Ala Ala Pro Ser Ala Thr Ser Gln Leu<br>                        245                         250                       255 | 768 | |
| tca act cgc gcc ctg gaa ggg att ttt gaa gca act cat cga ttg att<br>Ser Thr Arg Ala Leu Glu Gly Ile Phe Glu Ala Thr His Arg Leu Ile<br>         260                         265                       270 | 816 | |
| tac ggc gct aag gat gac tct ggt cag aga tac ctg gcc tgg tct gga<br>Tyr Gly Ala Lys Asp Asp Ser Gly Gln Arg Tyr Leu Ala Trp Ser Gly<br>         275                         280                       285 | 864 | |
| cac agt gcc cgt gtc gga gcc gcg cga gat atg gcc cgc gct gga gtt<br>His Ser Ala Arg Val Gly Ala Ala Arg Asp Met Ala Arg Ala Gly Val<br>     290                         295                       300 | 912 | |
| tca ata ccg gag atc atg caa gct ggt ggc tgg acc aat gta aat att<br>Ser Ile Pro Glu Ile Met Gln Ala Gly Gly Trp Thr Asn Val Asn Ile<br>305                         310                         315                   320 | 960 | |
| gtc atg aac tat atc cgt aac ctg gat agt gaa aca ggg gca atg gtg<br>Val Met Asn Tyr Ile Arg Asn Leu Asp Ser Glu Thr Gly Ala Met Val<br>                       325                       330                       335 | 1008 | |
| cgc ctg ctg gaa gat ggc gat ctc gag cca tct gct gga gac atg aga<br>Arg Leu Leu Glu Asp Gly Asp Leu Glu Pro Ser Ala Gly Asp Met Arg<br>         340                         345                       350 | 1056 | |
| gct gcc aac ctt tgg cca agc ccg ctc atg atc aaa cgc tct aag aag<br>Ala Ala Asn Leu Trp Pro Ser Pro Leu Met Ile Lys Arg Ser Lys Lys<br>                355                       360                       365 | 1104 | |
| aac agc ctg gcc ttg tcc ctg acg gcc gac cag atg gtc agt gcc ttg<br>Asn Ser Leu Ala Leu Ser Leu Thr Ala Asp Gln Met Val Ser Ala Leu<br>370                         375                         380 | 1152 | |
| ttg gat gct gag ccc ccc ata ctc tat tcc gag tat gat cct acc aga<br>Leu Asp Ala Glu Pro Pro Ile Leu Tyr Ser Glu Tyr Asp Pro Thr Arg<br>385                         390                         395                   400 | 1200 | |
| ccc ttc agt gaa gct tcg atg atg ggc tta ctg acc aac ctg gca gac<br>Pro Phe Ser Glu Ala Ser Met Met Gly Leu Leu Thr Asn Leu Ala Asp<br>                       405                         410                   415 | 1248 | |
| agg gag ctg gtt cac atg atc aac tgg gcg aag agg gtg cca ggc ttt<br>Arg Glu Leu Val His Met Ile Asn Trp Ala Lys Arg Val Pro Gly Phe<br>                420                       425                       430 | 1296 | |
| gtg gat ttg acc ctc cat gat cag gtc cac ctt cta gaa tgt gcc tgg<br>Val Asp Leu Thr Leu His Asp Gln Val His Leu Leu Glu Cys Ala Trp<br>                       435                         440                   445 | 1344 | |
| cta gag atc ctg atg att ggt ctc gtc tgg cgc tcc atg gag cac cca<br>Leu Glu Ile Leu Met Ile Gly Leu Val Trp Arg Ser Met Glu His Pro<br>450                         455                         460 | 1392 | |
| ggg aag cta ctg ttt gct cct aac ttg ctc ttg gac agg aac cag gga<br>Gly Lys Leu Leu Phe Ala Pro Asn Leu Leu Leu Asp Arg Asn Gln Gly<br>465                         470                         475                   480 | 1440 | |
| aaa tgt gta gag ggc atg gtg gag atc ttc gac atg ctg ctg gct aca<br>Lys Cys Val Glu Gly Met Val Glu Ile Phe Asp Met Leu Leu Ala Thr<br>                       485                         490                   495 | 1488 | |
| tca tct cgg ttc cgc atg atg aat ctg cag gga gag gag ttt gtg tgc<br>Ser Ser Arg Phe Arg Met Met Asn Leu Gln Gly Glu Glu Phe Val Cys<br>                       500                         505                   510 | 1536 | |
| ctc aaa tct att att ttg ctt aat tct gga gtg tac aca ttt ctg tcc<br>Leu Lys Ser Ile Ile Leu Leu Asn Ser Gly Val Tyr Thr Phe Leu Ser<br>                515                       520                       525 | 1584 | |
| agc acc ctg aag tct ctg gaa gag aag gac cat atc cac cga gtc ctg<br>Ser Thr Leu Lys Ser Leu Glu Glu Lys Asp His Ile His Arg Val Leu<br>530                         535                         540 | 1632 | |

-continued

```
gac aag atc aca gac act ttg atc cac ctg atg gcc aag gca ggc ctg      1680
Asp Lys Ile Thr Asp Thr Leu Ile His Leu Met Ala Lys Ala Gly Leu
545                 550                 555                 560 acc ctg cag cag cag cac cag cgg ctg gcc cag ctc ctc ctc atc ctc      1728
Thr Leu Gln Gln Gln His Gln Arg Leu Ala Gln Leu Leu Leu Ile Leu
                565                 570                 575 tcc cac atc agg cac atg agt aac aaa aga atg gag cat ctg tac agc      1776
Ser His Ile Arg His Met Ser Asn Lys Arg Met Glu His Leu Tyr Ser
            580                 585                 590 atg aag tgc aag aac gtg gtg ccc ctc tat gac ctg ctg ctg gag atg      1824
Met Lys Cys Lys Asn Val Val Pro Leu Tyr Asp Leu Leu Leu Glu Met
        595                 600                 605 ctg gac gcc cac cgc cta cat gcg ccc act agc cgt gga ggg gca tcc      1872
Leu Asp Ala His Arg Leu His Ala Pro Thr Ser Arg Gly Gly Ala Ser
    610                 615                 620 gtg gag gag acg gac caa agc cac ttg gcc act gcg ggc tct act tca      1920
Val Glu Glu Thr Asp Gln Ser His Leu Ala Thr Ala Gly Ser Thr Ser
625                 630                 635                 640 tcg cat tcc ttg caa aag tat tac atc acg ggg gag gca gag ggt ttc      1968
Ser His Ser Leu Gln Lys Tyr Tyr Ile Thr Gly Glu Ala Glu Gly Phe
                645                 650                 655 cct gcc aca gtc tga                                                   1983
Pro Ala Thr Val
        660

<210> SEQ ID NO 4
<211> LENGTH: 660
<212> TYPE: PRT
<213> ORGANISM: Artificial sequence
<220> FEATURE:
<223> OTHER INFORMATION: Description of Artificial Sequence: Chimeric
      sequence Homosapiens-Bacteriophage P1

<400> SEQUENCE: 4

Met Ser Asn Leu Leu Thr Val His Gln Asn Leu Pro Ala Leu Pro Val
 1               5                  10                  15

Asp Ala Thr Ser Asp Glu Val Arg Lys Asn Leu Met Asp Met Phe Arg
                20                  25                  30

Asp Arg Gln Ala Phe Ser Glu His Thr Trp Lys Met Leu Leu Ser Val
            35                  40                  45

Cys Arg Ser Trp Ala Ala Trp Cys Lys Leu Asn Asn Arg Lys Trp Phe
        50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190
```

```
Met Leu Ile His Ile Gly Arg Thr Lys Thr Leu Val Ser Thr Ala Gly
            195                 200                 205

Val Glu Lys Ala Leu Ser Leu Gly Val Thr Lys Leu Val Glu Arg Trp
            210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
            275                 280                 285

His Ser Ala Arg Val Gly Ala Ala Arg Asp Met Ala Arg Ala Gly Val
            290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp Leu Glu Pro Ser Ala Gly Asp Met Arg
            340                 345                 350

Ala Ala Asn Leu Trp Pro Ser Pro Leu Met Ile Lys Arg Ser Lys Lys
            355                 360                 365

Asn Ser Leu Ala Leu Ser Leu Thr Ala Asp Gln Met Val Ser Ala Leu
            370                 375                 380

Leu Asp Ala Glu Pro Pro Ile Leu Tyr Ser Glu Tyr Asp Pro Thr Arg
385                 390                 395                 400

Pro Phe Ser Glu Ala Ser Met Met Gly Leu Leu Thr Asn Leu Ala Asp
                405                 410                 415

Arg Glu Leu Val His Met Ile Asn Trp Ala Lys Arg Val Pro Gly Phe
            420                 425                 430

Val Asp Leu Thr Leu His Asp Gln Val His Leu Leu Glu Cys Ala Trp
            435                 440                 445

Leu Glu Ile Leu Met Ile Gly Leu Val Trp Arg Ser Met Glu His Pro
450                 455                 460

Gly Lys Leu Leu Phe Ala Pro Asn Leu Leu Leu Asp Arg Asn Gln Gly
465                 470                 475                 480

Lys Cys Val Glu Gly Met Val Glu Ile Phe Asp Met Leu Leu Ala Thr
                485                 490                 495

Ser Ser Arg Phe Arg Met Met Asn Leu Gln Gly Glu Glu Phe Val Cys
            500                 505                 510

Leu Lys Ser Ile Ile Leu Leu Asn Ser Gly Val Tyr Thr Phe Leu Ser
            515                 520                 525

Ser Thr Leu Lys Ser Leu Glu Glu Lys Asp His Ile His Arg Val Leu
            530                 535                 540

Asp Lys Ile Thr Asp Thr Leu Ile His Leu Met Ala Lys Ala Gly Leu
545                 550                 555                 560

Thr Leu Gln Gln Gln His Gln Arg Leu Ala Gln Leu Leu Leu Ile Leu
                565                 570                 575

Ser His Ile Arg His Met Ser Asn Lys Arg Met Glu His Leu Tyr Ser
            580                 585                 590

Met Lys Cys Lys Asn Val Val Pro Leu Tyr Asp Leu Leu Leu Glu Met
            595                 600                 605
```

```
Leu Asp Ala His Arg Leu His Ala Pro Thr Ser Arg Gly Gly Ala Ser
    610                 615                 620

Val Glu Glu Thr Asp Gln Ser His Leu Ala Thr Ala Gly Ser Thr Ser
625                 630                 635                 640

Ser His Ser Leu Gln Lys Tyr Tyr Ile Thr Gly Glu Ala Glu Gly Phe
                645                 650                 655

Pro Ala Thr Val
            660

<210> SEQ ID NO 5
<211> LENGTH: 1983
<212> TYPE: DNA
<213> ORGANISM: Artificial sequence
<220> FEATURE:
<221> NAME/KEY: CDS
<222> LOCATION: (1)..(1983)
<223> OTHER INFORMATION: Description of Artificial Sequence: Chimeric
      sequence Homosapiens-Bacteriophage P1

<400> SEQUENCE: 5 atg tcc aat tta ctg acc gta cac caa aat ttg cct gca tta ccg gtc      48
Met Ser Asn Leu Leu Thr Val His Gln Asn Leu Pro Ala Leu Pro Val
1               5                   10                  15 gat gca acg agt gat gag gtt cgc aag aac ctg atg gac atg ttc agg      96
Asp Ala Thr Ser Asp Glu Val Arg Lys Asn Leu Met Asp Met Phe Arg
                20                  25                  30 gat cgc cag gcg ttt tct gag cat acc tgg aaa atg ctt ctg tcc gtt     144
Asp Arg Gln Ala Phe Ser Glu His Thr Trp Lys Met Leu Leu Ser Val
            35                  40                  45 tgc cgg tcg tgg gcg gca tgg tgc aag ttg aat aac cgg aaa tgg ttt     192
Cys Arg Ser Trp Ala Ala Trp Cys Lys Leu Asn Asn Arg Lys Trp Phe
        50                  55                  60 ccc gca gaa cct gaa gat gtt cgc gat tat ctt cta tat ctt cag gcg     240
Pro Ala Glu Pro Glu Asp Val Arg Asp Tyr Leu Leu Tyr Leu Gln Ala
65                  70                  75                  80 cgc ggt ctg gca gta aaa act atc cag caa cat ttg ggc cag cta aac     288
Arg Gly Leu Ala Val Lys Thr Ile Gln Gln His Leu Gly Gln Leu Asn
                85                  90                  95 atg ctt cat cgt cgg tcc ggg ctg cca cga cca agt gac agc aat gct     336
Met Leu His Arg Arg Ser Gly Leu Pro Arg Pro Ser Asp Ser Asn Ala
                100                 105                 110 gtt tca ctg gtt atg cgg cgg atc cga aaa gaa aac gtt gat gcc ggt     384
Val Ser Leu Val Met Arg Arg Ile Arg Lys Glu Asn Val Asp Ala Gly
            115                 120                 125 gaa cgt gca aaa cag gct cta gcg ttc gaa cgc act gat ttc gac cag     432
Glu Arg Ala Lys Gln Ala Leu Ala Phe Glu Arg Thr Asp Phe Asp Gln
130                 135                 140 gtt cgt tca ctc atg gaa aat agc gat cgc tgc cag gat ata cgt aat     480
Val Arg Ser Leu Met Glu Asn Ser Asp Arg Cys Gln Asp Ile Arg Asn
145                 150                 155                 160 ctg gca ttt ctg ggg att gct tat aac acc ctg tta cgt ata gcc gaa     528
Leu Ala Phe Leu Gly Ile Ala Tyr Asn Thr Leu Leu Arg Ile Ala Glu
                165                 170                 175 att gcc agg atc agg gtt aaa gat atc tca cgt act gac ggt ggg aga     576
Ile Ala Arg Ile Arg Val Lys Asp Ile Ser Arg Thr Asp Gly Gly Arg
            180                 185                 190 atg tta atc cat att ggc aga acg aaa acg ctg gtt agc acc gca ggt     624
Met Leu Ile His Ile Gly Arg Thr Lys Thr Leu Val Ser Thr Ala Gly
        195                 200                 205 gta gag aag gca ctt agc ctg ggg gta act aaa ctg gtc gag cga tgg     672
Val Glu Lys Ala Leu Ser Leu Gly Val Thr Lys Leu Val Glu Arg Trp
```

-continued

| | | |
|---|---|---|
| att tcc gtc tct ggt gta gct gat gat ccg aat aac tac ctg ttt tgc<br>Ile Ser Val Ser Gly Val Ala Asp Asp Pro Asn Asn Tyr Leu Phe Cys<br>225                            230                        235                        240 | 720 |

```
                210                 215                 220
att tcc gtc tct ggt gta gct gat gat ccg aat aac tac ctg ttt tgc       720
Ile Ser Val Ser Gly Val Ala Asp Asp Pro Asn Asn Tyr Leu Phe Cys
225                 230                 235                 240 cgg gtc aga aaa aat ggt gtt gcc gcg cca tct gcc acc agc cag cta       768
Arg Val Arg Lys Asn Gly Val Ala Ala Pro Ser Ala Thr Ser Gln Leu
                245                 250                 255 tca act cgc gcc ctg gaa ggg att ttt gaa gca act cat cga ttg att       816
Ser Thr Arg Ala Leu Glu Gly Ile Phe Glu Ala Thr His Arg Leu Ile
            260                 265                 270 tac ggc gct aag gat gac tct ggt cag aga tac ctg gcc tgg tct gga       864
Tyr Gly Ala Lys Asp Asp Ser Gly Gln Arg Tyr Leu Ala Trp Ser Gly
        275                 280                 285 cac agt gcc cgt gtc gga gcc gcg cga gat atg gcc cgc gct gga gtt       912
His Ser Ala Arg Val Gly Ala Ala Arg Asp Met Ala Arg Ala Gly Val
    290                 295                 300 tca ata ccg gag atc atg caa gct ggt ggc tgg acc aat gta aat att       960
Ser Ile Pro Glu Ile Met Gln Ala Gly Gly Trp Thr Asn Val Asn Ile
305                 310                 315                 320 gtc atg aac tat atc cgt aac ctg gat agt gaa aca ggg gca atg gtg      1008
Val Met Asn Tyr Ile Arg Asn Leu Asp Ser Glu Thr Gly Ala Met Val
                325                 330                 335 cgc ctg ctg gaa gat ggc gat ctc gag cca tct gct gga gac atg aga      1056
Arg Leu Leu Glu Asp Gly Asp Leu Glu Pro Ser Ala Gly Asp Met Arg
            340                 345                 350 gct gcc aac ctt tgg cca agc ccg ctc atg atc aaa cgc tct aag aag      1104
Ala Ala Asn Leu Trp Pro Ser Pro Leu Met Ile Lys Arg Ser Lys Lys
        355                 360                 365 aac agc ctg gcc ttg tcc ctg acg gcc gac cag atg gtc agt gcc ttg      1152
Asn Ser Leu Ala Leu Ser Leu Thr Ala Asp Gln Met Val Ser Ala Leu
    370                 375                 380 ttg gat gct gag ccc ccc ata ctc tat tcc gag tat gat cct acc aga      1200
Leu Asp Ala Glu Pro Pro Ile Leu Tyr Ser Glu Tyr Asp Pro Thr Arg
385                 390                 395                 400 ccc ttc agt gaa gct tcg atg atg ggc tta ctg acc aac ctg gca gac      1248
Pro Phe Ser Glu Ala Ser Met Met Gly Leu Leu Thr Asn Leu Ala Asp
                405                 410                 415 agg gag ctg gtt cac atg atc aac tgg gcg aag agg gtg cca ggc ttt      1296
Arg Glu Leu Val His Met Ile Asn Trp Ala Lys Arg Val Pro Gly Phe
            420                 425                 430 gtg gat ttg acc ctc cat gat cag gtc cac ctt cta gaa tgt gcc tgg      1344
Val Asp Leu Thr Leu His Asp Gln Val His Leu Leu Glu Cys Ala Trp
        435                 440                 445 cta gag atc ctg atg att ggt ctc gtc tgg cgc tcc atg gag cac cca      1392
Leu Glu Ile Leu Met Ile Gly Leu Val Trp Arg Ser Met Glu His Pro
    450                 455                 460 gtg aag cta ctg ttt gct cct aac ttg ctc ttg gac agg aac cag gga      1440
Val Lys Leu Leu Phe Ala Pro Asn Leu Leu Leu Asp Arg Asn Gln Gly
465                 470                 475                 480 aaa tgt gta gag ggc atg gtg gag atc ttc gac atg ctg ctg gct aca      1488
Lys Cys Val Glu Gly Met Val Glu Ile Phe Asp Met Leu Leu Ala Thr
                485                 490                 495 tca tct cgg ttc cgc atg atg aat ctg cag gga gag gag ttt gtg tgc      1536
Ser Ser Arg Phe Arg Met Met Asn Leu Gln Gly Glu Glu Phe Val Cys
            500                 505                 510 ctc aaa tct att att ttg ctt aat tct gga gtg tac aca ttt ctg tcc      1584
Leu Lys Ser Ile Ile Leu Leu Asn Ser Gly Val Tyr Thr Phe Leu Ser
        515                 520                 525 agc acc ctg aag tct ctg gaa gag aag gac cat atc cac cga gtc ctg      1632
```

-continued

```
Ser Thr Leu Lys Ser Leu Glu Glu Lys Asp His Ile His Arg Val Leu
    530                 535                 540 gac aag atc aca gac act ttg atc cac ctg atg gcc aag gca ggc ctg      1680
Asp Lys Ile Thr Asp Thr Leu Ile His Leu Met Ala Lys Ala Gly Leu
545                 550                 555                 560 acc ctg cag cag cag cac cag cgg ctg gcc cag ctc ctc ctc atc ctc      1728
Thr Leu Gln Gln Gln His Gln Arg Leu Ala Gln Leu Leu Leu Ile Leu
                565                 570                 575 tcc cac atc agg cac atg agt aac aaa ggc atg gag cat ctg tac agc      1776
Ser His Ile Arg His Met Ser Asn Lys Gly Met Glu His Leu Tyr Ser
            580                 585                 590 atg aag tgc aag aac gtg gtg ccc ctc tat gac ctg ctg ctg gag gcg      1824
Met Lys Cys Lys Asn Val Val Pro Leu Tyr Asp Leu Leu Leu Glu Ala
        595                 600                 605 gcg gac gcc cac cgc cta cat gcg ccc act agc cgt gga ggg gca tcc      1872
Ala Asp Ala His Arg Leu His Ala Pro Thr Ser Arg Gly Gly Ala Ser
    610                 615                 620 gtg gag gag acg gac caa agc cac ttg gcc act gcg ggc tct act tca      1920
Val Glu Glu Thr Asp Gln Ser His Leu Ala Thr Ala Gly Ser Thr Ser
625                 630                 635                 640 tcg cat tcc ttg caa aag tat tac atc acg ggg gag gca gag ggt ttc      1968
Ser His Ser Leu Gln Lys Tyr Tyr Ile Thr Gly Glu Ala Glu Gly Phe
                645                 650                 655 cct gcc aca gct tga                                                   1983
Pro Ala Thr Ala
            660
```

<210> SEQ ID NO 6
<211> LENGTH: 660
<212> TYPE: PRT
<213> ORGANISM: Artificial sequence
<220> FEATURE:
<223> OTHER INFORMATION: Description of Artificial Sequence: Chimeric
      sequence Homosapiens-Bacteriophage P1

<400> SEQUENCE: 6

```
Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175
```

-continued

```
Ile Ala Arg Ile Arg Val Lys Asp Ile Ser Arg Thr Asp Gly Gly Arg
            180                 185                 190
Met Leu Ile His Ile Gly Arg Thr Lys Thr Leu Val Ser Thr Ala Gly
            195                 200                 205
Val Glu Lys Ala Leu Ser Leu Gly Val Thr Lys Leu Val Glu Arg Trp
            210                 215                 220
Ile Ser Val Ser Gly Val Ala Asp Asp Pro Asn Asn Tyr Leu Phe Cys
225                 230                 235                 240
Arg Val Arg Lys Asn Gly Val Ala Ala Pro Ser Ala Thr Ser Gln Leu
                245                 250                 255
Ser Thr Arg Ala Leu Glu Gly Ile Phe Glu Ala Thr His Arg Leu Ile
            260                 265                 270
Tyr Gly Ala Lys Asp Asp Ser Gly Gln Arg Tyr Leu Ala Trp Ser Gly
            275                 280                 285
His Ser Ala Arg Val Gly Ala Ala Arg Asp Met Ala Arg Ala Gly Val
            290                 295                 300
Ser Ile Pro Glu Ile Met Gln Ala Gly Gly Trp Thr Asn Val Asn Ile
305                 310                 315                 320
Val Met Asn Tyr Ile Arg Asn Leu Asp Ser Glu Thr Gly Ala Met Val
                325                 330                 335
Arg Leu Leu Glu Asp Gly Asp Leu Glu Pro Ser Ala Gly Asp Met Arg
            340                 345                 350
Ala Ala Asn Leu Trp Pro Ser Pro Leu Met Ile Lys Arg Ser Lys Lys
            355                 360                 365
Asn Ser Leu Ala Leu Ser Leu Thr Ala Asp Gln Met Val Ser Ala Leu
370                 375                 380
Leu Asp Ala Glu Pro Pro Ile Leu Tyr Ser Glu Tyr Asp Pro Thr Arg
385                 390                 395                 400
Pro Phe Ser Glu Ala Ser Met Met Gly Leu Leu Thr Asn Leu Ala Asp
                405                 410                 415
Arg Glu Leu Val His Met Ile Asn Trp Ala Lys Arg Val Pro Gly Phe
            420                 425                 430
Val Asp Leu Thr Leu His Asp Gln Val His Leu Leu Glu Cys Ala Trp
            435                 440                 445
Leu Glu Ile Leu Met Ile Gly Leu Val Trp Arg Ser Met Glu His Pro
            450                 455                 460
Val Lys Leu Leu Phe Ala Pro Asn Leu Leu Asp Arg Asn Gln Gly
465                 470                 475                 480
Lys Cys Val Glu Gly Met Val Glu Ile Phe Asp Met Leu Leu Ala Thr
                485                 490                 495
Ser Ser Arg Phe Arg Met Met Asn Leu Gln Gly Glu Glu Phe Val Cys
            500                 505                 510
Leu Lys Ser Ile Ile Leu Leu Asn Ser Gly Val Tyr Thr Phe Leu Ser
            515                 520                 525
Ser Thr Leu Lys Ser Leu Glu Glu Lys Asp His Ile His Arg Val Leu
            530                 535                 540
Asp Lys Ile Thr Asp Thr Leu Ile His Leu Met Ala Lys Ala Gly Leu
545                 550                 555                 560
Thr Leu Gln Gln Gln His Gln Arg Leu Ala Gln Leu Leu Leu Ile Leu
                565                 570                 575
Ser His Ile Arg His Met Ser Asn Lys Gly Met Glu His Leu Tyr Ser
            580                 585                 590
Met Lys Cys Lys Asn Val Val Pro Leu Tyr Asp Leu Leu Leu Glu Ala
```

```
                        595                 600                 605
Ala Asp Ala His Arg Leu His Ala Pro Thr Ser Arg Gly Gly Ala Ser
            610                 615                 620

Val Glu Glu Thr Asp Gln Ser His Leu Ala Thr Ala Gly Ser Thr Ser
625                 630                 635                 640

Ser His Ser Leu Gln Lys Tyr Tyr Ile Thr Gly Glu Ala Glu Gly Phe
                645                 650                 655

Pro Ala Thr Ala
            660

<210> SEQ ID NO 7
<211> LENGTH: 1983
<212> TYPE: DNA
<213> ORGANISM: Artificial sequence
<220> FEATURE:
<221> NAME/KEY: CDS
<222> LOCATION: (1)..(1983)
<223> OTHER INFORMATION: Description of Artificial Sequence: Chimeric
      sequence Homosapiens-Bacteriophage P1

<400> SEQUENCE: 7 atg tcc aat tta ctg acc gta cac caa aat ttg cct gca tta ccg gtc      48
Met Ser Asn Leu Leu Thr Val His Gln Asn Leu Pro Ala Leu Pro Val
  1               5                  10                  15 gat gca acg agt gat gag gtt cgc aag aac ctg atg gac atg ttc agg      96
Asp Ala Thr Ser Asp Glu Val Arg Lys Asn Leu Met Asp Met Phe Arg
             20                  25                  30 gat cgc cag gcg ttt tct gag cat acc tgg aaa atg ctt ctg tcc gtt     144
Asp Arg Gln Ala Phe Ser Glu His Thr Trp Lys Met Leu Leu Ser Val
         35                  40                  45 tgc cgg tcg tgg gcg gca tgg tgc aag ttg aat aac cgg aaa tgg ttt     192
Cys Arg Ser Trp Ala Ala Trp Cys Lys Leu Asn Asn Arg Lys Trp Phe
     50                  55                  60 ccc gca gaa cct gaa gat gtt cgc gat tat ctt cta tat ctt cag gcg     240
Pro Ala Glu Pro Glu Asp Val Arg Asp Tyr Leu Leu Tyr Leu Gln Ala
 65                  70                  75                  80 cgc ggt ctg gca gta aaa act atc cag caa cat ttg ggc cag cta aac     288
Arg Gly Leu Ala Val Lys Thr Ile Gln Gln His Leu Gly Gln Leu Asn
                 85                  90                  95 atg ctt cat cgt cgg tcc ggg ctg cca cga cca agt gac agc aat gct     336
Met Leu His Arg Arg Ser Gly Leu Pro Arg Pro Ser Asp Ser Asn Ala
            100                 105                 110 gtt tca ctg gtt atg cgg cgg atc cga aaa gaa aac gtt gat gcc ggt     384
Val Ser Leu Val Met Arg Arg Ile Arg Lys Glu Asn Val Asp Ala Gly
        115                 120                 125 gaa cgt gca aaa cag gct cta gcg ttc gaa cgc act gat ttc gac cag     432
Glu Arg Ala Lys Gln Ala Leu Ala Phe Glu Arg Thr Asp Phe Asp Gln
    130                 135                 140 gtt cgt tca ctc atg gaa aat agc gat cgc tgc cag gat ata cgt aat     480
Val Arg Ser Leu Met Glu Asn Ser Asp Arg Cys Gln Asp Ile Arg Asn
145                 150                 155                 160 ctg gca ttt ctg ggg att gct tat aac acc ctg tta cgt ata gcc gaa     528
Leu Ala Phe Leu Gly Ile Ala Tyr Asn Thr Leu Leu Arg Ile Ala Glu
                165                 170                 175 att gcc agg atc agg gtt aaa gat atc tca cgt act gac ggt ggg aga     576
Ile Ala Arg Ile Arg Val Lys Asp Ile Ser Arg Thr Asp Gly Gly Arg
            180                 185                 190 atg tta atc cat att ggc aga acg aaa acg ctg gtt agc acc gca ggt     624
Met Leu Ile His Ile Gly Arg Thr Lys Thr Leu Val Ser Thr Ala Gly
        195                 200                 205
```

| | | |
|---|---|---|
| gta gag aag gca ctt agc ctg ggg gta act aaa ctg gtc gag cga tgg<br>Val Glu Lys Ala Leu Ser Leu Gly Val Thr Lys Leu Val Glu Arg Trp<br>210                       215                     220 | | 672 |
| att tcc gtc tct ggt gta gct gat gat ccg aat aac tac ctg ttt tgc<br>Ile Ser Val Ser Gly Val Ala Asp Asp Pro Asn Asn Tyr Leu Phe Cys<br>225                     230                    235                  240 | | 720 |
| cgg gtc aga aaa aat ggt gtt gcc gcg cca tct gcc acc agc cag cta<br>Arg Val Arg Lys Asn Gly Val Ala Ala Pro Ser Ala Thr Ser Gln Leu<br>                    245                    250                    255 | | 768 |
| tca act cgc gcc ctg gaa ggg att ttt gaa gca act cat cga ttg att<br>Ser Thr Arg Ala Leu Glu Gly Ile Phe Glu Ala Thr His Arg Leu Ile<br>        260                    265                    270 | | 816 |
| tac ggc gct aag gat gac tct ggt cag aga tac ctg gcc tgg tct gga<br>Tyr Gly Ala Lys Asp Asp Ser Gly Gln Arg Tyr Leu Ala Trp Ser Gly<br>        275                    280                    285 | | 864 |
| cac agt gcc cgt gtc gga gcc gcg cga gat atg gcc cgc gct gga gtt<br>His Ser Ala Arg Val Gly Ala Ala Arg Asp Met Ala Arg Ala Gly Val<br>290                     295                    300 | | 912 |
| tca ata ccg gag atc atg caa gct ggt ggc tgg acc aat gta aat att<br>Ser Ile Pro Glu Ile Met Gln Ala Gly Gly Trp Thr Asn Val Asn Ile<br>305                     310                    315                  320 | | 960 |
| gtc atg aac tat atc cgt aac ctg gat agt gaa aca ggg gca atg gtg<br>Val Met Asn Tyr Ile Arg Asn Leu Asp Ser Glu Thr Gly Ala Met Val<br>                    325                    330                    335 | | 1008 |
| cgc ctg ctg gaa gat ggc gat ctc gag cca tct gct gga gac atg aga<br>Arg Leu Leu Glu Asp Gly Asp Leu Glu Pro Ser Ala Gly Asp Met Arg<br>        340                    345                    350 | | 1056 |
| gct gcc aac ctt tgg cca agc ccg ctc atg atc aaa cgc tct aag aag<br>Ala Ala Asn Leu Trp Pro Ser Pro Leu Met Ile Lys Arg Ser Lys Lys<br>                  355                    360                    365 | | 1104 |
| aac agc ctg gcc ttg tcc ctg acg gcc gac cag atg gtc agt gcc ttg<br>Asn Ser Leu Ala Leu Ser Leu Thr Ala Asp Gln Met Val Ser Ala Leu<br>370                     375                    380 | | 1152 |
| ttg gat gct gag ccc ccc ata ctc tat tcc gag tat gat cct acc aga<br>Leu Asp Ala Glu Pro Pro Ile Leu Tyr Ser Glu Tyr Asp Pro Thr Arg<br>385                     390                    395                  400 | | 1200 |
| ccc ttc agt gaa gct tcg atg atg ggc tta ctg acc aac ctg gca gac<br>Pro Phe Ser Glu Ala Ser Met Met Gly Leu Leu Thr Asn Leu Ala Asp<br>                    405                    410                    415 | | 1248 |
| agg gag ctg gtt cac atg atc aac tgg gcg aag agg gtg cca ggc ttt<br>Arg Glu Leu Val His Met Ile Asn Trp Ala Lys Arg Val Pro Gly Phe<br>        420                    425                    430 | | 1296 |
| gtg gat ttg acc ctc cat gat cag gtc cac ctt cta gaa tgt gcc tgg<br>Val Asp Leu Thr Leu His Asp Gln Val His Leu Leu Glu Cys Ala Trp<br>        435                    440                    445 | | 1344 |
| cta gag atc ctg atg att ggt ctc gtc tgg cgc tcc atg gag cac cca<br>Leu Glu Ile Leu Met Ile Gly Leu Val Trp Arg Ser Met Glu His Pro<br>450                     455                    460 | | 1392 |
| ggg aag cta ctg ttt gct cct aac ttg ctc ttg gac agg aac cag gga<br>Gly Lys Leu Leu Phe Ala Pro Asn Leu Leu Leu Asp Arg Asn Gln Gly<br>465                     470                    475                  480 | | 1440 |
| aaa tgt gta gag ggc atg gtg gag atc ttc gac atg ctg ctg gct aca<br>Lys Cys Val Glu Gly Met Val Glu Ile Phe Asp Met Leu Leu Ala Thr<br>                    485                    490                    495 | | 1488 |
| tca tct cgg ttc cgc atg atg aat ctg cag gga gag gag ttt gtg tgc<br>Ser Ser Arg Phe Arg Met Met Asn Leu Gln Gly Glu Glu Phe Val Cys<br>        500                    505                    510 | | 1536 |
| ctc aaa tct att att ttg ctt aat tct gga gtg tac aca ttt ctg tcc<br>Leu Lys Ser Ile Ile Leu Leu Asn Ser Gly Val Tyr Thr Phe Leu Ser<br>        515                    520                    525 | | 1584 |

-continued

```
agc acc ctg aag tct ctg gaa gag aag gac cat atc cac cga gtc ctg    1632
Ser Thr Leu Lys Ser Leu Glu Glu Lys Asp His Ile His Arg Val Leu
    530                 535                 540 gac aag atc aca gac act ttg atc cac ctg atg gcc aag gca ggc ctg    1680
Asp Lys Ile Thr Asp Thr Leu Ile His Leu Met Ala Lys Ala Gly Leu
545                 550                 555                 560 acc ctg cag cag cag cac cag cgg ctg gcc cag ctc ctc ctc atc ctc    1728
Thr Leu Gln Gln Gln His Gln Arg Leu Ala Gln Leu Leu Leu Ile Leu
                565                 570                 575 tcc cac atc agg cac atg agt aac aaa ggc atg gag cat ctg tac agc    1776
Ser His Ile Arg His Met Ser Asn Lys Gly Met Glu His Leu Tyr Ser
            580                 585                 590 atg aag tgc aag aac gtg gtg ccc ctc tat gac ctg ctg ctg gag gcg    1824
Met Lys Cys Lys Asn Val Val Pro Leu Tyr Asp Leu Leu Leu Glu Ala
        595                 600                 605 gcg gac gcc cac cgc cta cat gcg ccc act agc cgt gga ggg gca tcc    1872
Ala Asp Ala His Arg Leu His Ala Pro Thr Ser Arg Gly Gly Ala Ser
    610                 615                 620 gtg gag gag acg gac caa agc cac ttg gcc act gcg ggc tct act tca    1920
Val Glu Glu Thr Asp Gln Ser His Leu Ala Thr Ala Gly Ser Thr Ser
625                 630                 635                 640 tcg cat tcc ttg caa aag tat tac atc acg ggg gag gca gag ggt ttc    1968
Ser His Ser Leu Gln Lys Tyr Tyr Ile Thr Gly Glu Ala Glu Gly Phe
                645                 650                 655 cct gcc aca gct tga                                                 1983
Pro Ala Thr Ala
            660

<210> SEQ ID NO 8
<211> LENGTH: 660
<212> TYPE: PRT
<213> ORGANISM: Artificial sequence
<220> FEATURE:
<223> OTHER INFORMATION: Description of Artificial Sequence: Chimeric
      sequence Homosapiens-Bacteriophage P1

<400> SEQUENCE: 8

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
```

```
                165                 170                 175
Ile Ala Arg Ile Arg Val Lys Asp Ile Ser Arg Thr Asp Gly Gly Arg
            180                 185                 190
Met Leu Ile His Ile Gly Arg Thr Lys Thr Leu Val Ser Thr Ala Gly
            195                 200                 205
Val Glu Lys Ala Leu Ser Leu Gly Val Thr Lys Leu Val Glu Arg Trp
            210                 215                 220
Ile Ser Val Ser Gly Val Ala Asp Asp Pro Asn Asn Tyr Leu Phe Cys
225                 230                 235                 240
Arg Val Arg Lys Asn Gly Val Ala Ala Pro Ser Ala Thr Ser Gln Leu
            245                 250                 255
Ser Thr Arg Ala Leu Glu Gly Ile Phe Glu Ala Thr His Arg Leu Ile
            260                 265                 270
Tyr Gly Ala Lys Asp Asp Ser Gly Gln Arg Tyr Leu Ala Trp Ser Gly
            275                 280                 285
His Ser Ala Arg Val Gly Ala Ala Arg Asp Met Ala Arg Ala Gly Val
            290                 295                 300
Ser Ile Pro Glu Ile Met Gln Ala Gly Gly Trp Thr Asn Val Asn Ile
305                 310                 315                 320
Val Met Asn Tyr Ile Arg Asn Leu Asp Ser Glu Thr Gly Ala Met Val
            325                 330                 335
Arg Leu Leu Glu Asp Gly Asp Leu Glu Pro Ser Ala Gly Asp Met Arg
            340                 345                 350
Ala Ala Asn Leu Trp Pro Ser Pro Leu Met Ile Lys Arg Ser Lys Lys
            355                 360                 365
Asn Ser Leu Ala Leu Ser Leu Thr Ala Asp Gln Met Val Ser Ala Leu
            370                 375                 380
Leu Asp Ala Glu Pro Pro Ile Leu Tyr Ser Glu Tyr Asp Pro Thr Arg
385                 390                 395                 400
Pro Phe Ser Glu Ala Ser Met Met Gly Leu Leu Thr Asn Leu Ala Asp
            405                 410                 415
Arg Glu Leu Val His Met Ile Asn Trp Ala Lys Arg Val Pro Gly Phe
            420                 425                 430
Val Asp Leu Thr Leu His Asp Gln Val His Leu Leu Glu Cys Ala Trp
            435                 440                 445
Leu Glu Ile Leu Met Ile Gly Leu Val Trp Arg Ser Met Glu His Pro
            450                 455                 460
Gly Lys Leu Leu Phe Ala Pro Asn Leu Leu Leu Asp Arg Asn Gln Gly
465                 470                 475                 480
Lys Cys Val Glu Gly Met Val Glu Ile Phe Asp Met Leu Leu Ala Thr
            485                 490                 495
Ser Ser Arg Phe Arg Met Met Asn Leu Gln Gly Glu Glu Phe Val Cys
            500                 505                 510
Leu Lys Ser Ile Ile Leu Leu Asn Ser Gly Val Tyr Thr Phe Leu Ser
            515                 520                 525
Ser Thr Leu Lys Ser Leu Glu Glu Lys Asp His Ile His Arg Val Leu
            530                 535                 540
Asp Lys Ile Thr Asp Thr Leu Ile His Leu Met Ala Lys Ala Gly Leu
545                 550                 555                 560
Thr Leu Gln Gln Gln His Gln Arg Leu Ala Gln Leu Leu Leu Ile Leu
            565                 570                 575
Ser His Ile Arg His Met Ser Asn Lys Gly Met Glu His Leu Tyr Ser
            580                 585                 590
```

```
Met Lys Cys Lys Asn Val Val Pro Leu Tyr Asp Leu Leu Leu Glu Ala
            595                 600                 605

Ala Asp Ala His Arg Leu His Ala Pro Thr Ser Arg Gly Gly Ala Ser
610                 615                 620

Val Glu Glu Thr Asp Gln Ser His Leu Ala Thr Ala Gly Ser Thr Ser
625                 630                 635                 640

Ser His Ser Leu Gln Lys Tyr Tyr Ile Thr Gly Glu Ala Glu Gly Phe
            645                 650                 655

Pro Ala Thr Ala
            660

<210> SEQ ID NO 9
<211> LENGTH: 20
<212> TYPE: DNA
<213> ORGANISM: Homo sapiens

<400> SEQUENCE: 9
tccttcacca agcacatctg                                            20

<210> SEQ ID NO 10
<211> LENGTH: 20
<212> TYPE: DNA
<213> ORGANISM: Homo sapiens

<400> SEQUENCE: 10
tgcagccctc acaactgtat                                            20

<210> SEQ ID NO 11
<211> LENGTH: 21
<212> TYPE: DNA
<213> ORGANISM: Homo sapiens

<400> SEQUENCE: 11
caacctgcac ttgtcactta g                                          21

<210> SEQ ID NO 12
<211> LENGTH: 20
<212> TYPE: DNA
<213> ORGANISM: Homo sapiens

<400> SEQUENCE: 12
atgtttcata gttggatatc                                            20

<210> SEQ ID NO 13
<211> LENGTH: 37
<212> TYPE: DNA
<213> ORGANISM: Mus musculus

<400> SEQUENCE: 13
atacgcggcc gcgaattcca gcaggaatca ggtagct                         37

<210> SEQ ID NO 14
<211> LENGTH: 37
<212> TYPE: DNA
<213> ORGANISM: Mus musculus

<400> SEQUENCE: 14
atagcgccgg cgctgcagca caggagggtg ctatgag                         37
```

TRANSGENIC MOUSE FOR TARGETED RECOMBINATION MEDIATED BY MODIFIED CRE-ER

The present invention relates to a metazoan organism, with the exception or humans, and in particular a mouse, characterized in that at least one cell of this organism comprises at least one fusion protein between a recombinase Cre and a modified nuclear estrogen receptor allowing it to respond to synthetic antiestrogens but not to natural estrogens, and one or more DNA sequences of interest belonging to the genome of said organism into which one or more sites of recognition of said recombinase protein are inserted. The invention also cover the methods using said organism for the mutagenesis and the analysis of the biological function of the DNA sequence(s) of interest, in particular of the gene(s) of interest, such as $RXR_\alpha$.

The ability to modify the genome of animals, more particularly of mice, by integrating transgenes randomly or at preselected sites, by homologous recombination, in embryonic stem cells (ES cells) has made it possible to greatly improve our understanding of the biological function of mammalian genes under normal and/or pathological conditions (Jaenisch, 1988; Capecchi, 1989). However, these techniques have proved not to be very informative in a large number of cases, in particular because the hereditary mutations thus generated were lethal during development and/or because their effects were pleiotropic.

To remedy these defects, strategies for conditional somatic mutagenesis have been developed, particularly in mice; they make it possible to selectively induce mutations in a given cell type (spatial control) or at a given time (temporal control) during the life of the animal.

A first strategy consists in combining the targeted homologous recombination with the site-specific recombination systems based on the use of recombinases which catalyze the recombination reaction between two short recognition DNA sequences. It has been shown that these site-specific recombination systems, although of microbial origin for the majority, could function in higher eukaryotes, such as plants, insects and mice (Sauer, 1994; Rajewsky et al., 1996; Sauer, 1998). Among the site-specific recombination systems commonly used, there may be mentioned the Cre/Lox (Sauer, 1998) and FLP/FRT (Kilby et al., 1993) systems. The strategy normally used consists in inserting the loxP (or FRT) sites into the chromosomes of ES cells by homologous recombination, or by conventional transgenesis, and then in delivering Cre (or FLP) for the latter to catalyze the recombination reaction. The recombination between the two loxP (or FRT) sites may be obtained in ES cells (Gu et al., 1993) or in fertilized eggs (Araki et al., 1995) by transient expression of Cre or using a Cre transgenic mouse (Lakso et al., 1992; Orban et al., 1992). Such a strategy of somatic mutagenesis allows a spatial control of the recombination, because the expression of the recombinase is controlled by a promoter specific for a given tissue or for a given cell. However, this strategy also has limitations because some somatic alterations can lead to a lethal phenotype at an early stage of development, thus preventing any subsequent biological or physiological study. Also, an insufficiently specific expression of the recombinase can lead to recombination events in a non-desired cell type (Betz et al., 1996) which, if they occur early during embryogenesis, can cause recombination of the DNA in the majority of the adult tissues, and thereby complicate the analysis of the mutant phenotype.

A second strategy has consisted in controlling the expression of recombinases over time so as to allow temporal control of somatic recombination. To do this, the expression of the recombinases is controlled by inducible promoters (Kühn et al., 1995; Saint-Onge et al, 1996), such as the interferon-inducible promoter, for example. This system also has limitations because it does not make it possible to obtain spatial control of the recombination.

The coupling of the tetracycline-inducible expression system developed by H. Bujard (Gossen et al., 1992; WO 94 04672; EP 804 546) with the site-specific recombinase system has made it possible to develop a system for somatic modification of the genome which is controlled spatiotemporally. Such a system is based on the activation or repression, by tetracycline, of the promoter controlling the expression of the recombinase gene. Such a method, although making it possible to obtain a spatiotemporal control of the somatic recombination, has the disadvantage of being cumbersome to carry out because it requires the creation of a doubly transgenic animal.

It has been possible to envisage a new strategy following the development of chimeric recombinases selectively activated by the natural ligand for the estrogen receptor. Indeed, the observation that the activity of numerous proteins, including at least two enzymes (the tyrosine kinases c-abl and src) is controlled by estrogens, when the latter is linked to the ligand-binding domain (LBD) of the estrogen receptor α (ERα) (Jackson et al., 1993; Picard et al., 1994) has made it possible to develop strategies for spatiotemporally controlled site-specific recombination (Logie et al., 1995; Metzger at al., 1995). However, to use such chimeric recombinases to successfully carry out conditional somatic mutagenesis in vertebrates (in particular mice) which produce estrogens, it was necessary to create recombinases which are not activated by the estrogens present in the animal, otherwise the temporal control of the recombination of the target genes would not be obtained. Thus, mutations were introduced into the ERα LBD, and it has been shown, in cells in culture, that the chimeric recombinase Cre-ER$^T$ no longer responds to the natural estrogens, despite being efficiently activated by antiestrogens such as 4-hydroxytamoxifen (OHT) (Feil et al., 1996).

The feasibility of the site-specific somatic recombination activated by an antiestrogenic ligand has thus been demonstrated for "reporter" DNA sequences, in mice, and in particular in various transgenic mouse lines which express the fusion protein Cre-ER$^T$ activated by Tamoxifen (Tam) (Fail et al., 1996; Brocard et al., 1997; Indra et al., 1999). The feasibility of the site-specific recombination activated by a ligand for a gene present in its natural chromatin environment has been demonstrated in mice by Schwenk et al. (1998). Schwenk et al. have thus carried out the deletion, inducible by injection of Tamoxifen, of a polβ gene in B cell: using a mouse expressing, specifically in the B lymphocytes, a fusion protein between the recombinase Cre and the ligand-binding domain of the mutated human nuclear estrogen receptor. However, the technology developed by Schwenk et al. does not make it possible to obtain a satisfactory efficiency of spatiotemporally controlled site-specific recombination in cells expressing the fusion protein because the efficiency varies between a few percents and 80%, in spite of the use of high doses of OHT (five infections of 8 mg). Moreover, the results presented by Schwenk et al. show that in the absence of synthetic ligand, the activity of the fusion protein used may be induced by natural ligands generating a non negligible residual "background noise" which may be detected by PCR.

Up until now, the possibility of carrying out the ligand-activated, site-specific somatic recombination of chromosomal DNA sequence(s), in their natural chromatin environment, has therefore never been able to be satisfactorily demonstrated in animals, in particular mice, that is to say with a very high efficiency in the presence of synthetic ligand and with a negligible or even zero "background noise" in its absence.

As highlighted by Schwenk et al. in the discussion in their article, there is a real need to develop transgenic animals in whose cells site-specific recombination could be spatiotemporally induced with an efficiency of close to 100% in the presence of synthetic ligand, and which could not occur in any cell in the absence of synthetic ligand and/or in the presence of a natural ligand.

Moreover, a need also exists to develop chimeric recombinases with increased sensitivity to the synthetic ligand, so as to avoid injecting into the animals massive doses of synthetic ligand which can cause in these animals not only unjustified suffering, but can also affect the general metabolism of the animal, which would distort subsequent physiological and behavioral studies.

Unexpectedly, the inventors have solved the problems mentioned earlier, which had not been resolved up until now, by combining the selection of novel mutations in the ligand-binding domain of the human nuclear estrogen receptor, the selection of a suitable hinge region between the two domains of the chimeric recombinase, and the selection of promoters suitable for directing the expression of the chimeric recombinase in a given tissue.

The present invention therefore relates to a metazoan organism, with the exception of humans, characterized in that at least one cell of said organism comprises at least;
(i) one fusion protein comprising sequentially:
  a recombinase protein;
  a hinge region of at least 15 amino acids;
  a polypeptide comprising the ligand-binding domain of the human nuclear estrogen receptor, or of a vertebrate nuclear estrogen receptor, and their natural variants or one of their fragments, said polypeptide exhibiting at least one mutation relative to the wild-type form of said ligand-binding domains, or of their natural variants, or of their fragments, and said fusion protein having a negligible, or even zero, recombinase activity in the presence of a natural ligand, such as for example estradiol, and a recombinase activity induced by a small quantity of synthetic ligand endowed with anti-estrogenic activity, such as for example Tam and OHT;
(ii) one or more gene or intergenic DNA sequences of interest naturally belonging to said genome of said organism into which one or more recognition sites of said recombinase protein are inserted, said DNA sequence (s) of interest being located in one or more of the chromosomes of the genome of said cell.

The expression "metazoan organism" is understood to mean any animal organism, with the exception of humans, consisting of several cells. According to a preferred embodiment, it is a vertebrate such as for example a mammal, a bird, a fish. Preferably, it is a mammal such as for example a bovine, a porcine, a caprine, an ovine, an equine, a rodent. According to a more preferred embodiment, it as a rodent such as mice or rats.

The expression "recombinase protein" is understood to designate recombinases of the family of integrases which catalyze the excision, insertion, inversion or translocation of DNA fragments at the level of specific sites of recognition said recombinases (Sternberg et al., 1986, Sauer, et al., 1990; Barbonis et al., 1993; Kilby et al., 1993; Sauer, 1994; Denisen et al., 1995). These recombinases are active in animal cells (Sauer, 1994).

The recombinase protein of the invention is preferably selected from the group of site-specific recombinases composed of the Cre recombinase of bacteriophage P1, the FLP recombinase of *Saccharomyces cerevisiae*, the R recombinase of *Zygosaccharomyces rouxii* pSR1, the A recombinase of *Kluyveromyces drosophilarium* pKD1, the A recombinase of *Kluyveromyces waltii* pKW1, the integrase λInt, the recombinase of the GIN Recombination system of the Mu phage, of the bacterial β recombinase (Diaz et al., 1999) or a variant thereof.

The Cre ("cyclization recombination") recombinase which is a 38 KDa integrase of bacteriophage P1 catalyzes, in the absence of cofactors, recombination between two DNA sequences of 34 basepairs called "loxP site" (Sauer et al., 1990). The position on one or more DNA molecules and the orientation of the loxP sites relative to each other determine the-type of function of the Cre recombinase: excision, insertion, inversion or translocation. Thus, the recombinase activity of Cre is an inversion when two loxP sites are inverted on the same DNA fragment, and an excision when the loxP sites are in the form of a direct repeat on the same DNA fragment. The activity of the recombinase is an insertion when the loxP site is present on a DNA fragment, it being possible for a DNA molecule such as a plasmid containing a loxP site to be inserted at the level of said loxP site. The Cre recombinase can also induce translocation between two chromosomes provided that a loxP site is present on each of them (Babinet, 1995). More generally, the Cre recombinase is therefore capable of catalyzing recombination between one or more different DNA molecules provided that they carry loxP sites.

The FLP recombinase of the FLP/FRT system is a recombinase of 43 KDa from *Saccharomyces cerevisiae* which is capable of the same type of action as the Cre recombinase on DNA fragments containing FRT recognition sites (Kilby et al., 1993).

Preferably, the recombinase according to the invention is the Ore recombinase of bacteriophage P1 and its natural or synthetic variants, and said sites of recognition specific for said Cre recombinase are preferably chosen from the group composed of the sequences Lox P, Lox 66, Lox 71, Lox 511, Lox 512, Lox 514.

The expression "variant of the recombinase protein"is understood to mean all the wild-type recombinases or fragments thereof which may exist naturally and which correspond in particular to truncations, substitutions, deletions and/or additions of amino acid residues. These recombinases and fragments thereof are preferably derived from the genetic polymorphism in the population. The expression "recombinase fragment" is understood to mean any recombinase portion exhibiting at least one recombinase activity. The expression variant of the recombinase protein is also understood to mean the synthetic variants for which the above modifications are not naturally present, but were introduced artificially, by genetic engineering for example. Thus, the recombinases derived from chimeric fusion constitute synthetic variants according to the invention. Such recombinases have been described for example in Shaikh and Sadowski (2000).

Said hinge region according to the invention comprises the D hinge region of the nuclear estrogen receptor, preferably the human nuclear estrogen receptor α, or one of its fragments.

The D hinge region (region 263 to 301 of the sequence SEQ ID No. 2) is a region situated between the ER C region which contains the DNA-binding domain (region 180–262 of the sequence SEQ ID No. 2) and the ligand-binding domain (region 302 to 552 of the sequence SEQ ID No. 2).

Preferably, this hinge region sequentially comprises at least (i) two amino acids corresponds to the introduction of a restriction site, of a "linker", or of an adapter, which are necessary for the cloning of the fusion gene, and (ii) one fragment of the D hinge region of the human nuclear estrogen receptor α, corresponding to amino acids 282 to 301 of the sequence SEQ ID No. 2. Preferably, said restriction site is an XhoI site and the two corresponding amino acids are leucine and glutamine.

The hinge region according to the invention has a size of at least 15, 17, 19, 21, 23, 25, 27, 29, 31, 33, 35, 40, 45, 50, 55, 60, 65, 70, 100, 150, 200, 250, 292 amino acids. According to a preferred embodiment, said hinge region comprises at least 15 amino acids and at most 54 amino acids. More preferably still, the hinge region comprises 23 amino acids. The width of the hinge region influences the regulation of the recombinase activity by the ligand.

The hinge region according to the invention may consist of a peptide which is functionally equivalent to said D hinge region.

The estrogen receptors (ER) are proteins regulating the transcription of genes which mediate the action of estrogens in the target cells. The ERs belong to the superfamily of nuclear receptors which have a common modular structure: (i) a variable N-terminal A/B region containing the constitutive transactivation activity AF-1, (ii) a DNA-binding central domain C (DBD) which is highly conserved between various species and allowing binding of the receptor to its specific DNA response element, (iii) and a ligand-binding domain (LBD), located in the C-terminal region of ER (for review articles and references see Evans, 1988; Beato et al., 1989; Gronemeyer, 1991; Green and Chambon, 1988; Parker, 1993; Simons, 1994).

The nuclear estrogen receptors according to the invention are chosen from the human nuclear estrogen receptors, and from the nuclear estrogen receptors of vertebrates such as for example the various species of primates, bovines, porcines, ovines, caprines, felines, canines, equines, birds, fish, rodents, in particular rats and mice.

According to a preferred embodiment, the source organism for the estrogen receptor according to the invention is characterized in that said ligand-binding domain (LBD) of the nuclear estrogen receptor, or its natural variants, or one of their fragments, is human and is chosen from the LBDs of the human nuclear α and β estrogen receptors (ERα and ERβ). According to a further preferred mode, this includes the LBD of the human nuclear estrogen receptor α corresponding to amino acids 302 to 552, or its natural variants, or one of their fragments.

The expression "natural variant" is understood to mean all the LBDs of the nuclear estrogen receptors or their fragments which may exist naturally, in particular in human beings, and corresponding in particular to truncations, substitutions, deletions and/or additions of amino acid residues. These natural variants are derived in general from the genetic polymorphism in the population, and have an activity which is not substantially modified compared with the wild-type receptor.

There are also included in the scope of the invention the polypeptides homologous to the LBDs of the wild-type nuclear estrogen receptors, or to their variants, or to one of their fragments, and which exhibit certain modifications, in particular a deletion, addition, substitution of at least one amino acid, a truncation, an extension and/or a chimeric fusion.

The expression "nuclear receptor fragment" is understood to mean any portion of the nuclear estrogen receptor LBDs exhibiting at least the LBD activity.

Said fusion protein according to the invention is therefore preferably Cre-ER and comprises the Cre recombinase protein to which is fused a portion of the D hinge region and the LBD (amino acids 282 to 595 of the sequence SEQ ID No. 2) of the mutated human nuclear estrogen receptor α (SEQ ID No. 2). The fusion protein according to the invention comprises at least the portion of the nuclear estrogen receptor having a ligand binding activity.

Said LBD of the nuclear receptor, or one of its fragments, has at least one mutation. This mutation is preferably chosen from the group:

mutation (G521R) glycine to arginine at position 521 of the sequence SEQ ID No. 2 or of a natural variant of this sequence;

mutation (G400V) glycine to valine at position 400 of the sequence SEQ ID No. 2 or of a natural variant of this sequence;

mutation (methionine-leucine) to (alanine-alanine) situated at position 543–544 (M543A/L544A mutation) of the sequence SEQ ID No. 2 or of a natural variant of this sequence.

The term "mutation" is understood to mean any changes occurring in the sequence of the nuclear estrogen receptor, and in particular of the human nuclear estrogen receptor α, other than those present in its natural variants, and/or in its human or vertebrate homologous, and which substantially modify the activity of the recombinase protein fused to said receptor or to said ligand-binding domain, in response to the binding of a synthetic ligand endowed with antiestrogenic activity.

Among the mutations capable of being introduced into the LBD of the nuclear estrogen receptor, there may be mentioned point mutations, deletions, insertions, substitutions However, it is advisable to select only the mutations introduced into the LBD of the nuclear estrogen receptors which allow induction of the activity of the Cre recombinase fused to said receptor by a synthetic ligand in low concentration, while avoiding as far as possible the inducing of a basal activity by the natural ligands for this receptor which are naturally present in the metazoan organism. Likewise, it will be advisable to select the mutations which do not confer activity on the Cre recombinase fused to said receptor in the absence of a ligand.

The G521R mutation constitutes an LBD mutation of the ER according to the invention. This mutation is similar to the G525R mutation introduced into the mouse ER LBD (mER) which reduces the affinity for the natural ligand, estradiol, by about 1000 fold, without adversely affecting the binding of the synthetic ligand, 4-hydroxyTamoxifen (OHT) (Danielan et al., 1993). Thus, the inventors have shown that the recombinase activity of the Cre-ER$^T$ (T=for inducible by Tamaoxifen) fusion protein which carries the G521R mutation, and the amino acid glycine at position 400, called Cre-ER(GR) in the article by Feil et al. 1997, is dependent on the addition of OHT or of Tam to the medium for culturing transfected cells. On the other hand, no recombinase activity is observed in the presence of OHT when the fusion protein carries the G521R mutation and the G400V mutation (mutant called Cre-ER(VR) in Feil et al., (1997)).

The inventors have also created the fusion protein corresponding to the triple mutant G400V/MS43A/L544A called Cre-ER$^{T2}$ (Feil et al., 1997). This fusion protein exhibits a recombinase activity in cultured cells which is induced by the antiestrogen Tam or OHT, but not by the natural ligand estradiol; moreover, the maximum activity of Cre-ER$^{T2}$ is induced for Tam or OHT doses less than those necessary to activate Cre-ER$^T$. This increased sensitivity to Tam or OHT of Cre-ER$^{T2}$ compared with Cre-ER$^T$ has been verified in transgenic mice selectively expressing the chimeric recombinases in the basal layer of the epidermis, under the control or the cytokeratin 5 promoter (Indra et al., 1999), The Inventors have observed that the translocation of Cre-ER$^{T2}$ from the cytoplasm into the nucleus, as well as the excision of the DNA sequences flanked by loxP sites from a "reporter" gene are induced at doses of about ten times less than those necessary for Cre-ER$^T$.

With the aim of further increasing the sensitivity of the chimeric recombinase Cre-ER$^{T2}$ to Tamoxifen, the inventors replaced the valine at position 400 in Cre-ER$^{T2}$ with a glycine. This novel fusion protein which corresponds to the double mutant M543A/LS44A called Cre-ER$^{T3}$ exhibits increased sensitivity to the synthetic antiestrogenic ligand such as Tam and OHT, without the recombinase activity of this protein being induced by the natural ligand estradiol.

The inventors have thus shown that for 10 times lower injected Tam doses, the recombinase activity in the cells of a transgenic Cre-ER$^{T3}$ mouse is greater than that of a Cre-ER$^{T2}$ mouse (see Example 5).

According to a preferred embodiment, the fusion protein according to the invention is Cre-ER$^{T2}$ whose ER LBD exhibits the mutation G400V/M543A/L544A According to another preferred embodiment, the fusion protein is Cre-ER$^{T3}$, whose ER LBD exhibits the mutation M543A/L544A.

One of the objects of the present invention is therefore to provide a Cre-ER fusion protein which exhibits mutations in the human ERα LED which are preferably chosen from the mutations G521R, G400V, M543A and L544A, whose recombinase activity is not induced by the natural ligands, and is highly induced by a small quantity of synthetic antiestrogenic ligand. Preferably, this fusion protein is Cre-ER$^T$, Cre-ER$^{T2}$, Cre-ER$^{T3}$. The present invention also relates to said fusion gene encoding said protein, said vector for expressing said protein, as well as the corresponding host cell, and the corresponding transgenic animal, which expresses said fusion protein in a particular cell type, preferably the epidermis, the liver or the adipose tissue.

The Cre-ER fusion protein of the present invention therefore comprises all or part of a nuclear estrogen receptor and a recombinase protein whose activity is inducible more strongly by the binding of said receptor or of said ligand-binding domain (LBD) of said receptor with a said antiestrogen than with a natural ligand. Said Cre-ER fusion protein makes it possible to carry out a recombination between loxP sites, in a cell of the organism of the invention, following treatment with an antiestrogen. In the absence of treatment, or in the presence of concentrations of ligands such as the natural estrogens of up to $10^{-6}$ M, no excision is observed. This system therefore makes it possible to release the recombinase activity of the chimeric protein at a given and chosen moment. Said Cre-ER fusion protein may be expressed in cells containing loxP sites, without modifying the locus containing the loxP sites. The recombination at the level of the loxP sites takes place only after treatment with an antiestrogen such as Tam or OHT. Furthermore, by expressing said Cre-ER fusion protein in an organism according to the invention, preferably an animal, under the control of a promoter with cellular specificity, it is possible to obtain recombination between loxP sites, specifically in these cells.

The expression "synthetic ligand" is understood to mean any type of compound capable of binding to the nuclear estrogen receptor, and exhibiting agonist and/or antagonist activities, according to the species, the tissue or the cell type. Preferably, and with no limitation being implied, the synthetic ligand according to the invention is endowed with antiestrogenic activity, it is preferably the antiestrogenic therapeutic agent Tamoxifen (Tam), but also its metabolite 4-hydroxyTamoxifen (OHT). The antiestrogens ICI 164 384 and ICI 182 780 are also synthetic ligands according to the invention.

The present invention therefore provides a transgenic metazoan organism and more particularly a transgenic animal, and in particular a transgenic mouse: (i) in which at least one cell contains one or more chromosomal DNA sequences which are present in their natural chromatin context and are flanked (floxed) by loxP sites; (ii) which preferably expresses a chimeric Cre recombinase in a tissue-specific manner in one or more cell types of the organism (iii) whose chimeric Cre recombinase activity is negligible, or even zero, in the presence of estrogen; (iv) whose chimeric recombinase activity is activated by low concentrations of an antiestrogen (from 0.001 to 1 mg of Tamoxifen/mouse/day, for five days); (v) and finally whose Cre recombinase is capable of catalyzing, with an efficiency close to 100%, the site-specific targeted somatic recombination in the nucleus, in a natural chromatin environment of the floxed DNA sequence(s).

The doses of synthetic ligand injected into the metazoan organism according to the invention are low. The term low is understood to mean quantities of less than or equal to 4 mg/adult mouse/day, preferably less than or equal to 2 mg/adult mouse/day, in a preferred manner less than or equal to 1 mg/adult mouse/day. According to an even more preferred mode, this quantity may be less than or equal to 0.5 mg, 0.25 mg, 0.10 mg, 0.075 mg, 0.05 mg, 0.025 mg, 0.001 mg per adult mouse and per day.

It is clearly understood that persons skilled in the art will be able to adjust these quantities, according to the organism, its weight and its age.

The efficiency of the targeted somatic recombination is estimated by techniques known to persons skilled in the art. This efficiency is estimated by the frequency of recombination events catalyzed by said recombinase. These events may be revealed by PCR or Southern Blotting; the recombination frequency being estimated by taking the ratio of the representation of the various alleles in the cells of a tissue. The frequencies of the various alleles may be estimated by assaying the intensity of the corresponding bands on an electrophoresis gel of a product of PCR amplification or of genomic DNA (Southern blotting).

The use of the PCR makes this method of estimation extremely sensitive and makes it possible to detect the presence of cells of the organism whose genome has not undergone targeted site-specific recombination.

Another way of estimating the efficiency of the recombination may be carried our indirectly by immunohistochemistry, by analyzing the expression of the gene sequence to be inactivated for example.

According to a preferred embodiment, said fusion protein is encoded by a fusion gene integrated into one or more of the chromosomes of said cell of said organism. According to another embodiment, the fusion protein is encoded by a fusion gene integrated into an expression vector. The fusion gene according to the invention is introduced into the cell in the form of an expression vector or of one of its fragments. A "vector" is a replicon in which another polynucleotide segment (i.e. the fusion gene) is attached, so as to bring the replication and/or expression to the attached segment. The vector may be in particular a bacterial plasmid DNA, a cosmid, a phage DNA, a viral DNA or a minichromosome (BAC, YAC and the like). Such a vector may be integrative, that is to say can integrate into the genome of the host cell or can exist in the form of an extrachromosomal replicon. When it exists in the form of an extrachromosomal replicon, the expression vector is capable of replicating autonomously. When it is a fragment of an expression vector, preferably this fragment integrates into the cellular genome. The expression vector or one of its fragments comprises at least the fusion gene and a promoter or expression elements which make it possible to direct and control the expression of said fusion protein in at least one cell of said organism.

The expression vector comprises, in addition, signals for initiation and termination of the transcription, as well as appropriate regions for regulation of the transcription. These various control signals are chosen according to the cellular host used.

The expression elements controlling expression is understood to mean all the DNA sequences involved in the regulation of the gene expression, that is to say the minimal promoter sequence, the upstream sequences, the activating sequences ("enhancers"), optionally the inhibitory sequences ("silencers"), the "insulator" sequences, and any other required sequence.

Preferably, the fusion gene is placed under the control of tissue-specific or cell-specific or ubiquitous expression elements.

The tissue-specific expression elements or tissue-specific promoter regions are chosen from the promoters which make it possible to obtain a specific, and preferably high, expression in one or more cells, tissues, cell types or organs of the organism according to the invention. These promoter regions may be heterologous or nonheterologous to the organism and may be naturally present or otherwise in the genome of the organism. By way of nonlimiting example of tissue-specific promoter regions, there may be mentioned the promoter regions of the genes:

for cytokeratin, and more particular for cytokeratin 5 (K5) and cytokeratin 14 (K14), which directs the expression of the gene in the basal keratinocytes of the epidermis;

for α-1-antitrypsin which directs the expression of the gene in the hepatocytes;

for the adipocyte fatty acid binding protein 2 (aP2) which directs the expression of the gene in the adipocytes.

According to a preferred embodiment, said organism is characterized in that said promoter region is the cytokeratin 5 (K5) promoter region and said fusion gene Cre-ER$^T$.

According to a second preferred embodiment, said organism is characterized in that said promoter region is the cytokeratin 5 (K5) promoter region and said fusion gene Cre-ER$^{T2}$.

According to a third preferred embodiment, said organism is characterized in that said promoter region is the cytokeratin 5 (K5) promoter region and said fusion gene Cre-ER$^{T3}$.

According to a fourth preferred embodiment, said organism is characterized in that said promoter region is the cytokeretin 14 (K14) promoter region and said fusion gene Cre-ER$^T$.

According to a fifth preferred embodiment, said organism is characterized in that said promoter region is the cytokeratin 14 (K14) promoter region and said fusion gene Cre-ER$^{T2}$.

According to a sixth preferred embodiment, said organist is characterized in that said promoter region is the cytokeratin 14 (K14) promoter region and said fusion gene Cre-ER$^{T3}$.

According to a seventh preferred embodiment, said organism is characterized in that said promoter region is the α-1-antitrypsin promoter region and said fusion gene Cre-ER$^T$.

According to an eighth preferred embodiment, said organism is characterized in that said promoter region is the α-1-antitrypsin promoter region and said fusion gene Cre-ER$^{T2}$.

According to a ninth preferred embodiment, said organism is characterized in that said promoter region is the α-1-antitrypsin promoter region and said fusion gene Cre-ER$^{T3}$.

According to a tenth preferred embodiment, said organism is characterized in that said promoter region is the adipocyte fatty acid binding protein 2 (aP2) promoter region and said fusion gene Cre-ER$^T$.

According to an eleventh preferred embodiment, said organism is characterized in that said promoter region is the adipocyte fatty acid binding protein 2 (aP2) promoter region and said fusion gene Cre-ER$^{T2}$.

According to a twelfth preferred embodiment, said organism is characterized in that said promoter region is the adipocyte fatty acid binding protein 2 (aP2) promoter region and said fusion gene Cre-ER$^{T3}$.

According to a first embodiment, the organism according to the invention is characterized in that said fusion gene has the sequence SEQ ID No. 3 and encodes the Cre-ER$^T$ protein having the sequence SEQ ID No. 4.

According to a second embodiment, the organism according to the invention is characterized in that said fusion gene encodes, of sequence SEQ ID No. 5 the fusion protein Cre-ER$^{T2}$ having the sequence SEQ ID No. 6.

According to a third embodiment, the organism according to the invention is characterized in that said fusion gene encodes, of sequence SEQ ID No. 7 the fusion protein Cre-ER$^{T3}$ having the sequence SEQ ID No. 8.

The article by Metzger and Feil (1999) gives by way of nonlimiting example (cf. table page 471) a list of tissue-specific promoter regions which are capable of being used to direct the expression of the Cre protein in various tissues.

The tissue-specific promoter regions are mare generally chosen from those which direct the expression of the fusion protein in a physiological system, an organ, a tissue, a cell type or a particular cell, among which there may be nonexhaustively mentioned the nervous system in general, and in particular the brain, the cerebellum, the neurons, the motoneurons, the glial cells, the Schwann cells, the hypophysis, the hypothalamus, the pituitary gland, the hippocampus and the cortex, the heart, the ventricular cardiomyocytes and the auricular cardiomyocytes, the lungs, the bones, the eyes, and more particularly the retina and the crystalline lens, the skin and more particularly the dermis and the epidermis, the muscles, and tore particularly the skeletal muscles, the cardiac muscle, the smooth muscles, the mammary gland, the gonads and more particularly the testes, the ovaries, the germ cells, the oocytes, the oogonias, the spermatozoa, the spermatogonias and the spermatocytes, the kidney, the liver and in particular the hepatocytes, the spleen, the pancreas and in particular the Langerhans' cells and the β cells, the tongue, the esophagus, the adipocytes, the vascular endothelial cells.

The ubiquitous expression elements or ubiquitous promoter regions are chosen from the promoter regions which make it possible to obtain expression, preferably high expression, in all, or at least in a high proportion, of organs, or of tissues of the organism according to the invention. These promoter regions may be heterologous or nonheterologous to the organism according to the invention. By way of nonlimiting example of "so called" ubiquitous promoter regions, there may be mentioned the cytomegalovirus (CMV) promoter (Schmidt et al., 1990) and the interferon-inducible promoter (M×1) (Hug et al., 1998; Arnheiter et al., 1990). In addition, the expression elements, or promoter regions according to the invention, can ensure a constitutive or inducible Control of the expression of the fusion gene, Among the elements ensuring inducible expression, there may be mentioned the eukaryotic promoter regions which are inducible by heavy metals (Mayo et al., 1982; Brinster et al., 1982; Seark et al., 1985), by heat shock (Nover et al., 1991), by hormones (Lee et al., 1981; Hynes et al., 1981; Klock et al., 1987; Israel et al., 1989), by interferon (Hug et al., 1998; Arnheiter et al., 1990). There may also be mentioned the inducible prokaryotic expression elements such as the *E. coli* Lac repressor system (LacR/operator/inducer) (Hu et al., 1987; Brown et al., 1987; Figge et al., 1988; Deuschle et al., 1990; Labow et al., 1990), the *E. coli* tetracycline resistance system (Gossen et al., 1992) (WO 94 04 672, EP 804 565).

In the case where the integration of the fusion gene is targeted by homologous recombination into the genome of the organism ("knock-in"), the fusion gene may be free of promoter regions or of expression elements and may be placed under the control of a promoter region or of endogenous expression elements.

The recombinant DNA technologies used for the construction of the expression vector according to the invention are those known and commonly used by persons skilled in the art. Standard techniques are used for cloning, isolation of DNA, amplification and purification; the enzymatic reactions involving DNA ligase, DNA polymerase, restriction endonucleases are carried out according to the manufacturer's recommendations. These techniques and others are generally carried out according to Sambrook et al. (1989).

The vector according to the invention or the vector fragments may be introduced into the host cell by standard methods such as for example microinjection into a pronucleus, transfection by calcium phosphate precipitation, lipofection, electroporation, heat shock.

The fusion gene according to the invention preferably comprises in the 5'→3' direction:
  a DNA fragment encoding the Cre recombinase of bacteriophage P1 or one of its variants;
  a DNA fragment of at least 45 nucleotides encoding at least either all or part of the D hinge region of a nuclear estrogen receptor, a region situated between the DNA-binding domain and the ligand-binding domain, or a peptide which is functionally equivalent to said D hinge region; and
  a DNA fragment encoding the ligand-binding domain (LBD) of a nuclear estrogen receptor or variants thereof, said fragment having at least one mutation conferring on LBD the capacity to respond to synthetic antiestrogens, but not to natural estrogenic agonists.

According to another embodiment of the invention, the fusion protein is directly introduced into the organism, or into a cell of the organism, it being possible for this introduction to be carried out by injection into a tissue or an organ in the case of an organism, or by microinjection in the case of a cell.

The DNA sequence of interest according to the invention is a gene or an intergenic sequence. According to a preferred embodiment of the invention, the DNA sequence of interest is a gene, it being possible for the function of the gene to be known or unknown. The study of an organism according to the invention exhibiting modification of a gene or of any other genomic region of unknown function makes it possible to contribute to the definition of the function of this gene or of this intergenic region. All the genes and intergenic regions of a metazoan organism are capable of being used in the context of the present invention; more particularly, there may be mentioned the $RXR_\alpha$, $RXR_\beta$, $RXR_\gamma$, $RAR_\alpha$, $RAR_\beta$, $RAR_\gamma$, $SNF2_\beta$ genes. The expression "DNA sequence of interest" naturally belonging to the genome of said organism, or DNA sequence of interest in its natural chromatin environment, is understood to mean an endogenous DNA sequence, such as an endogenous gene, present in the genome at its natural locus (loci).

According to a preferred embodiment of the invention, the organism according to the invention is an animal, in particular a mouse, characterized in that at least one of the cells of said mouse comprises:
  a fusion gene encoding the fusion protein Cre-$ER^T$ having the sequence SEQ ID No. 4, or Cre-$ER^{T2}$ having the sequence ID No. 6, or Cre-$ER^{T3}$ having the sequence ID No. 8, said fusion gene being under the control of the cytokeratin K5 promoter;
  one or more chromosomal DNA sequences of interest in their natural chromatin context and flanked ("floxed") by a lox site.

According to a second preferred embodiment of the invention, the organism according to the invention is characterized in that at least one of the cells of said mouse comprises:
  a fusion gene encoding the fusion protein Cre-$ER^T$ having the sequence SEQ ID No. 4, or Cre-$ER^{T2}$ having the sequence ID No. 6, or Cre-$ER^{T3}$ having the sequence ID No. 8, said fusion gene being under the control of the cytokeratin K14 promoter;
  one or more chromosomal DNA sequences of interest in their natural chromatin context and flanked ("floxed") by a lox site.

According to a third preferred embodiment of the invention, the organism according to the invention is characterized in that at least one of the cells of said mouse comprises:
  a fusion gene encoding the fusion protein Cre-$ER^T$ having the sequence SEQ ID No. 4, or Cre-$ER^{T2}$ having the sequence ID No. 6, or Cre-$ER^{T3}$ having the sequence ID No. 8, said fusion gene being under the control of the adipocyte fatty acid binding protein 2 (aP2) promoter;
  one or more chromosomal DNA sequences of interest in their natural chromatin context and flanked ("floxed") by a lox site.

According to a fourth preferred embodiment of the invention, the organism according to the invention is characterized in that at least one of the cells of said mouse comprises:
  a fusion gene encoding the fusion protein Cre-$ER^T$ having the sequence SEQ ID No. 4, or Cre-$ER^{T2}$ having the sequence ID No. 6, or Cre-$E^{T3}$ having the sequence ID No. 8, said fusion gene being under the control of the α-1-antitrypsin promoter;

one or more chromosomal DNA sequences of interest in their natural chromatin context and flanked ("floxed") by a lox site.

The present invention also relates to methods of preparing a metazoan organism according to the invention.

A first method of preparation consists in the steps of:
a) obtaining an embyronic stem (ES) cell modified by insertion of site(s) of recognition for said recombinase protein into said DNA sequencers) of interest, located in one or more chromosomes, by homologous recombination;
b) introducing said modified embryonic stem cell into an embryo of said organism;
c) developing said embryo up to the stage of a fertile adult organism;
d) crossing said fertile adult organism with a transgenic organism in which at least one of the cells expresses said fusion protein and obtaining the progeny derived from said crossing; and
e) optionally, selecting, among said progeny, said metazoan organism.

A second method of preparation consists in the steps of:
a) obtaining a somatic cell modified by insertion of site(s) of recognition for said recombinase protein into said DNA sequence(s) of interest, located in one or more chromosomes, by homologous recombination;
b) transferring the nucleus of said modified somatic cell into the cytoplasm of an enucleated recipient oocyte;
c) developing the embryo obtained in step b) up to the stage of a fertile adult organism;
d) crossing said fertile adult organism with a transgenic organism in which at least one of the cells expresses said fusion protein and obtaining the progeny derived from said crossing; and
e) optionally, selecting, among said progeny, said metazoan organism.

The expression transfer of the nucleus or nuclear transfer, for the purposes of the present invention, is understood to mean the transfer of nucleus of a vertebrate live donor cell, of an adult organism or at the fetal stage, into the cytoplasm of an enucleated recipient cell of the same species or of a different species. The transferred nucleus is reprogrammed to direct the development of the cloned embryos which may then be transferred into carrier females to produce the fetuses and the neonates, or used to produce cells of the internal cellular mass in culture. Various nuclear cloning techniques are capable of being used; among these, there may be mentioned those which have been the subject of patent applications WO 95 17500, WO 97 07668, WO 97 07669, WO 98 30683, WO 99 01163, WO 99 37143.

A third method of preparation consists in the steps of:
a) obtaining an embyronic stem (ES) cell modified by insertion of site(s) of recognition for said recombinase protein into said DNA sequence(s) of interest, located in one or more chromosomes, by homologous recombination;
b) introducing said modified embryonic stem cell into an embryo of said organism;
c) developing said embryo; and
d) introducing said fusion protein into at least one cell of said embryo or of the organism obtained from the development of said embryo.

A fourth method of preparation consists in the steps of:
a) obtaining a somatic cell modified by insertion of site(s) of recognition for said recombinase protein into said DNA sequence(s) of interest, located in one or more chromosomes, by homologous recombination;
b) transferring the nucleus of said modified somatic cell into the cytoplasm of an enucleated recipient oocyte;
c) developing said embryo; and
d) introducing said fusion protein into at least one cell of said embryo or of said organism obtained from the development of said embryo.

The insertion of the sites of recognition specific for the recombinase protein, in particular of the loxP site(s) for the Cre recombinase, into the DNA sequence of interest is preferably carried out by homologous recombination of the gene comprising said DNA fragment to be excised or inverted (two loxP sites) or respectively inserted or translocated (one loxP site) with a said modified gene comprising said DNA fragment to be excised flanked in 5' and/or 3' by said recombinase recognition site(s) according to the desired application, in particular the loxP sites.

To do this, the modified DNA fragment of interest may be integrated by homologous recombination into the genome of the cells of said organism before, at the same time, or after the step of introducing the fusion protein or of a transfer vector, or of a vector for expressing the fusion protein. Preferably, the DNA fragment of interest is introduced into pluripotent embryonic cells (ES cells) by the appropriate technique, such as for example electroporation, or the use of retrovitral vectors, calcium phosphate precipitation, lipofection.

The DNA constructs intended for homologous recombination will comprise at least a portion of the DNA sequence of interest, in particular of the gene or of the intergenic sequence of interest into which will be introduced the desired genetic modifications), such as the introduction of at least one recombinase recognition site, and which will include regions of homology with the target locus. For facilitated use, positive and/or negative selectable markers (for example the neo gene conferring resistance to the antibiotic G418) may be introduced. The selectable marker used to make it possible to identify the homologous recombination events may be disruptive, and may be eliminated, if necessary, if it is itself flanked by recombinase recognition sites such as the loxP (or FRT) sites. This makes it possible to obtain mice in which the sole modification at the level of the modified locus is the insertion of recognition sites such as loxP.

The metazoan organisms obtained by the methods of preparation presented above can then be treated with a synthetic ligand endowed with antiestrogenic activity such as Tam and OHT. In the various methods and uses of the invention, the bringing of said cells of said organism into contact with said synthetic ligand is carried out by administration by the oral or topical route, or by injection and in particular, by intravenous, intramuscular, intraspinal, intracerebral, intraperitoneal injection. In the case of an embryo, a fetus or a neonate before weaning, the treatment with the synthetic ligand may be carried out by administration to the mother. When this involves cells in culture derived from said organism, said synthetic ligand is preferably added to the culture medium, or injected into said cell. This treatment or this bringing into contact makes it possible to inactivate or to modify a gene or an intergenic sequence of interest at a determined moment (temporal control) in a given tissue (spatial control), and thus to make it possible to study the function of this gene or of this sequence at various periods during development or postnatally. This is particularly advantageous for studying at the adult stage genes which are essential for the normal progress of embryonic development and whose inactivation is lethal in utero or perinatally.

Another object of the present invention is therefore to provide a method of conditional recombination, in particular excision, insertion, inversion, translocation, at the level of the DNA sequence of interest into which there is (are) inserted one or more sites of recognition for said recombinase protein, said DNA sequence of interest being located in one or more of the chromosomes of said genome of said cell of said organism according to the invention, characterized in that it comprises the steps of:
(i) bringing at least one cell of said organism into contact with a synthetic ligand endowed with antiestrogenic activity;
(ii) inducing the activity of the recombinase of said fusion protein by said synthetic ligand endowed with antiestrogenic activity.

The present invention therefore provides a method of conditional deletion of a DNA fragment in which a method of excision according to the invention is used and in which said DNA fragment(s) to be excised is (are) flanked by two recombinase protein recognition sites oriented as a direct repeat. In particular, said DNA fragment may be chosen such that the excision of said DNA fragment has the effect of inactivating said gene.

The present invention also provides a method of obtaining a metazoan organism, with the exception of humans, in which at least one cell possesses an allele of a gene of interest inactivated by a method of conditional deletion and in which the other allele of said gene of interest possesses a mutation, said method being characterized in that it comprises the steps of:
a) obtaining a metazoan organism in which at least one cell of the germ line comprises said mutation in one of the alleles of said gene of interest;
b) crossing said organism obtained in step a) with an organism according to the invention;
c) selecting a progeny whose genome comprises a gene of interest in which one of the alleles possesses a mutation and the other allele possesses at least two recombinase protein recognition sites oriented as a direct repeat; and
d) using the method of conditional deletion, according to the invention, of the DNA fragment of said allele of said gene of interest which is flanked by at least two recombinase protein recognition sites oriented as a direct repeat; and
e) obtaining said metazoan organism in which the genome of at least one cell comprises said gene of interest in which one allele is inactivated, the other allele possesses a somatic, preferably limited, mutation and preferably in exon and/or regulatory sequences.

Such a method makes it possible to study and analyze the biological function of mutations other than deletions, and more particularly of the mutations observed in genes whose dysfunction causes a recessive genetic pathological condition. This method is therefore particularly suited to the obtaining of transgenic animal models of recessively transmitted human genetic pathological conditions, the animal model being preferably a murine model.

The mutations are preferably point or limited mutations in exons or regulatory sequences such as insertions, deletions, substitutions.

According to a preferred embodiment of the method of recombination, and of the method of conditional deletion or of the method of obtaining a metazoan organism according to the invention, the recombinase protein specific recognition sites are loxP sites and said recombinase protein is the Cre protein of the bacteriophage P1, or one of its variants.

The organisms capable of being obtained using the various methods above are also included in the scope of the invention. These organisms are preferably animals, and in a preferred manner rodents such as rats and mice, preferably mice.

Preferably, the subject of the invention is a transgenic mouse K5-Cre-ER$^T$/RXR$_\alpha^{L2/L2}$ whose RXR$_\alpha$ gene may be selectively inactivated in the basal keratinocytes of the epidermis using a conditional deletion method following treatment with a synthetic ligand endowed with antiestrogenic activity, causing in said mouse alopecia and/or hyperproliferation of the basal keratinocytes and/or an inflammatory reaction of the skin.

Preferably, the subject of the invention is a transgenic mouse K5-Cre-ER$^{T2}$/RXR$_\alpha^{L2/L2}$ whose RXR$_\alpha$ gene may be selectively inactivated in the basal keratinocytes of the epidermis using a conditional deletion method following treatment with a synthetic ligand endowed with antiestrogenic activity, causing in said mouse alopecia and/or hyperproliferation of the keratinocytes and/or an inflammatory reaction of the skin.

Preferably, the subject of the invention is a transgenic mouse K5-Cre-ER$^{T3}$/RXR$_\alpha^{L2/L2}$ whose RXR$_\alpha$ gene may be selectively inactivated in the basal keratinocytes of the epidermis using a conditional deletion method following treatment with a synthetic ligand endowed with antiestrogenic activity, causing in said mouse alopecia and/or hyperproliferation of the basal keratinocytes and/or an inflammatory reaction of the skin.

Preferably, the subject-of the invention is a transgenic mouse K14-Cre-ER$^T$/RXR$_\alpha^{L2/L2}$ whose RXR$_\alpha$ gene may be selectively inactivated in the basal keratinocytes of the epidermis using a conditional deletion method following treatment with a synthetic ligand endowed with antiestrogenic activity, causing in said mouse alopecia and/or hyperproliferation of the keratinocytes and/or an inflammatory reaction of the skin.

Preferably, the subject of the invention is a transgenic mouse K14-Cre-ER$^{T2}$/RXR$_\alpha^{L2/L2}$ whose RXR$_\alpha$ gene may be selectively inactivated in the basal keratinocytes of the epidermis using a conditional deletion method following treatment with a synthetic ligand endowed with antiestrogenic activity, causing in said mouse alopecia and/or hyperproliferation of the keratinocytes and/or an inflammatory reaction of the skin.

Preferably, the subject of the invention is a transgenic mouse K14-Cre-ER$^{T3}$/RXR$_\alpha^{L2/L2}$ whose RXR$_\alpha$ gene may be selectively inactivated in the basal keratinocytes of the epidermis using a conditional deletion method following treatment with a synthetic ligand endowed with antiestrogenic activity, causing in said mouse alopecia and/or hyperproliferation of the keratinocytes and/or an inflammatory reaction of the skin.

Preferably, the subject of the invention is a transgenic mouse $\alpha$AT-Cre-ER$^T$/RXR$_\alpha^{L2/L2}$ whose RXR$_\alpha$ gene may be selectively inactivated in the hepatocytes using a conditional deletion method following treatment with a synthetic ligand endowed with antiestrogenic activity, causing in said mouse in particular alteration of the proliferation of the hepatocytes.

Preferably, the subject of the invention is a transgenic mouse $\alpha$AT-Cre-ER$^{T2}$/RXR$_\alpha^{L2/L2}$ whose RXR$_\alpha$ gene may be selectively inactivated in the hepatocytes using a conditional deletion method following treatment with a synthetic ligand endowed with antiestrogenic activity, causing in said mouse in particular alteration of the proliferation of the hepatocytes.

Preferably, the subject of the invention is a transgenic mouse $\alpha$AT-Cre-ER$^{T3}$/RXR$_\alpha^{L2/L2}$ whose RXR$_\alpha$ gene may be selectively inactivated in the hepatocytes using a conditional deletion method following treatment with a synthetic ligand endowed with antiestrogenic activity, causing in said mouse in particular alteration of the proliferation of the hepatocytes.

Preferably, the subject of the invention is a transgenic mouse aP2-Cre-ER$^T$/RXR$_\alpha^{L2/L2}$ whose RXR$_\alpha$ gene may be selectively inactivated in the adipocytes using a conditional deletion method following treatment with a synthetic ligand endowed with antiestrogenic activity, causing in said mouse alteration of the metabolism of the lipids in the adipocytes and/or diabetes.

Preferably, the subject of the invention is a transgenic mouse aP2-Cre-ER$^{T2}$/RXR$_\alpha^{L2/L2}$ whose RXR$_\alpha$ gene may be selectively inactivated in the adipocytes using a conditional deletion method following treatment with a synthetic ligand endowed with antiestrogenic activity, causing in said mouse alteration of the metabolism of the lipids in the adipocytes and/or diabetes.

Preferably, the subject of the invention is a transgenic mouse aP2-Cre-ER$^{T3}$/RXR$_\alpha^{L2/L2}$ whose RXR$_\alpha$ gene may be selectively inactivated in the adipocytes using a conditional deletion method following treatment with a synthetic ligand endowed with antiestrogenic activity, causing in said mouse alteration of the metabolism of the lipids in the adipocytes and/or diabetes.

Preferably, said RXR$_\alpha$ gene of said mouse is inactivated using a method according to the invention.

The present invention and in particular the metazoan organism and the cells derived therefrom are particularly useful for analyzing and studying the biological function of a DNA sequence of interest, whether it is a gene or an intergenic sequence in its natural chromatin environment. That is the reason why it is also within the scope of the present invention to provide a method of analyzing or studying the biological function of a DNA sequence of interest, in particular of a gene or an intergenic sequence, characterized in that it comprises the steps of:
(i) bringing an organism according to the invention or cells isolated from said organism into contact with a synthetic ligand endowed with antiestrogenic activity;
(ii) optionally inducing the expression of said fusion protein;
(iii) revealing the recombination event catalyzed by the recombinase activity of said fusion protein;
(iv) biochemical and/or physiological and/or phenotypic and/or behavioral study or analysis of said cell or of said organism.

The phenotypic and behavioral analyses of the organism according to the invention before or after induction of the somatic recombination are carried out using techniques known to persons skilled in the art.

The subject of the present invention is also the use of an organism according to the invention or of cells derived from said organism for carrying out a spatiotemporally controlled site-specific recombination of said DNA sequence of interest in its natural chromatin environment, with an efficiency of at least 85%, 90%, 92%, 94%, 95%, 96%, 97%, 98%, 99%, 100%, in the presence of synthetic ligand in the cells of said organism expressing said fusion protein and with an efficiency at least less than 5%, 4%, 3%, 2%, 1%, 0.5%, 0.1%, 0.01%, or zero in the absence of synthetic ligand or in the presence of a natural ligand in the cells of said organism expressing said fusion protein.

According to a preferred mode, said recombination is carried out in the epidermis, and more precisely in keratinocytes, in the adipocytes, in the malanocytes or in the hepatocytes.

The subject of the present invention is also its method of screening compounds capable of being used as a medicament for the preventive and/or curative treatment of pathological conditions associated with alteration of the expression (in the case, in particular, of an intergenic DNA sequence) and/or of the function (in the case of a gene DNA sequence) of said DNA sequence of interest, characterized in that it comprises the step of administering said compound to an organism according to the invention.

This organism may thus be used for the screening of compounds capable of constituting an active ingredient of a medicament intended for the treatment of pathological conditions associated with alteration of the expression and/or of the function of said DNA sequence of interest.

Thus, the object of the present invention is to provide a method of screening compounds capable of being used as a medicament for the preventive and/or curative treatment of alopecia and/or of hyperproliferation of the keratinocytes and/or of inflammatory reactions of the skin, characterized in that it comprises the step of administering said compound to a mouse according to the invention.

The object of the present invention is also to provide a method of screening compounds capable of being used as a medicament for promoting, in particular, hepatic regeneration, characterized in that it comprises the step of administering said compound to a mouse according to the invention.

The object of the present invention is also to provide a method of screening compounds capable of being used as a medicament for the preventive and/or curative treatment of diabetes and/or for the treatment of the alteration of the metabolism of lipids, in particular of obesity, characterized in that it comprises the step of administering said compound to a mouse according to the invention.

The object of the present invention is also to provide a method of screening compound capable of being used as a medicament for the preventive and/or curative treatment of skin cancers, more specifically papillomas and melanomas at various stages of development, characterized in that it comprises the step of administering said compound to a mouse according to the invention.

Other characteristics and advantages of the present invention will emerge in the light of the examples which follow.

FIG. 1: Inactivation of the RXRα gene in the epidermis of adult mice mediated by Cre-ER$^T$ and Cre-ER$^{T2}$, and induced by Tamoxifen.

FIG. 1A: Schematic representation of the wild-type genomic locus of RXR$_\alpha$ (+), of the floxed L2 RXR$_\alpha$ allele, of the L$^-$ RXR$_\alpha$ allele obtained after Cre-mediated excision of exon 4 (encoding the DNA-binding domain), and of the RXR$_\alpha$ (−)null allele (Kastner et al., 1994). The black boxes indicate the exons (E2–E4). The enzymatic restriction sites and the position of the probe X4 are indicated. The sizes of the BamHI fragments are indicated in kilobases (kb); BamHI; C, ClaI; E, EcoRI H, HindIII; S, SpeI; X, XbaI. The arrow tips in the L2 and L$^-$ alleles indicate the Lox P sites.

FIG. 1B: The obtaining of RXR$_\alpha^{L-}$ alleles mediated by K5-Cre-ER$^T$ induced by Tamoxifen is illustrated by Southern blot analysis of the DNA isolated from the epidermis, six weeks (lanes 1 to 3) or twelve weeks (lanes 4 to 6) after the first injection of Tamoxifen (1 mg) (AFT: "after first Tamoxifen treatment"). The genotype of the mice is as indicated, and the fragments digested with BamHI corresponding to the RXR$_\alpha$(+), L2, L$^-$, (−) alleles are described.

FIG. 1C: Tissue selectivity of the inactivation of RXR$_\alpha$ mediated by Cre-ER$^T$. The wild-type alleles (+), L2, L$^-$ are identified by PCR from DNA extracted from various K5-Cre-ER$^{T(tg/0)}$/RXR$_\alpha$$^{L2/+}$ mouse organs, twelve weeks after the first Tamoxifen treatment.

FIG. 1D: The obtaining of L⁻ RXR$_\alpha$ alleles mediated by K14-Cre-ER$^{T2}$ induced by Tamoxifen in the epidermis of adult mice is illustrated by PCR analysis of the genomic DNA extract from the epidermis (E) and from the dermis (D) isolated two weeks after the first injection of Tamoxifen (0.1 mg) (+) or of the vehicle (oil) (−). The genotype of the mice is indicated and the PCR fragments corresponding to the RXR$_\alpha$(+), L2 and L− alleles are indicated.

FIG. 2: Abnormalities generated by the inactivation of RXR$_\alpha$ mediated by K5-Cre-ER$^T$ and K14-Cre-ER$^{T2}$ induced by Tamoxifen, in the skin of adult mice.

Figure 2A:
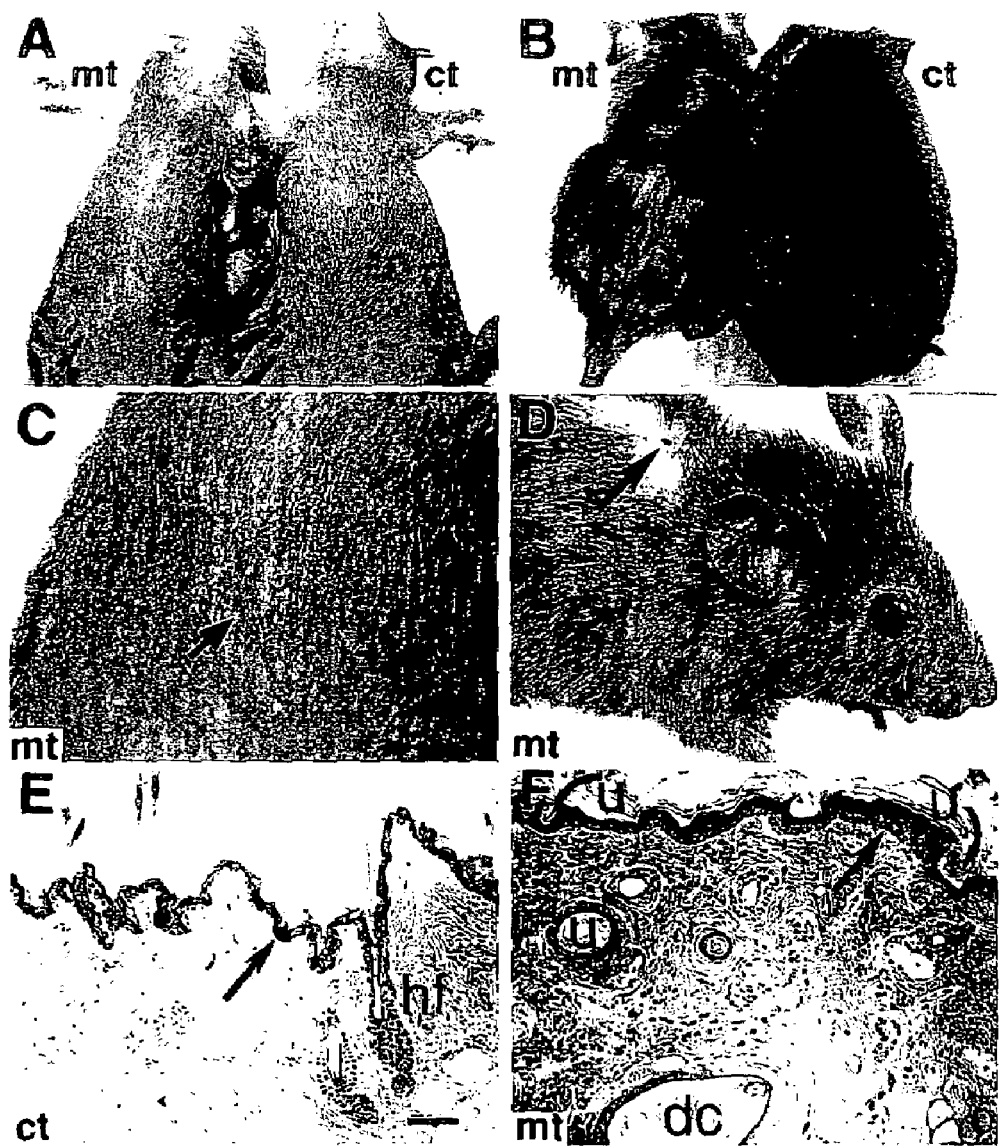

FIG. 2A: Ventral view of a "mutant" (mt) female mouse K5-Cre-ER$^{T(tg/0)}$/RXR$_\alpha$$^{L2/−}$ (on the left) and of a "control" (ct) female mouse K5-Cre-ER$^{T(tg/0)}$/RXR$_\alpha$$^{L2/+}$ (on the right), sixteen weeks after the first Tamoxifen injection (1 mg of Tamoxifen/injection).

Figure 2B:
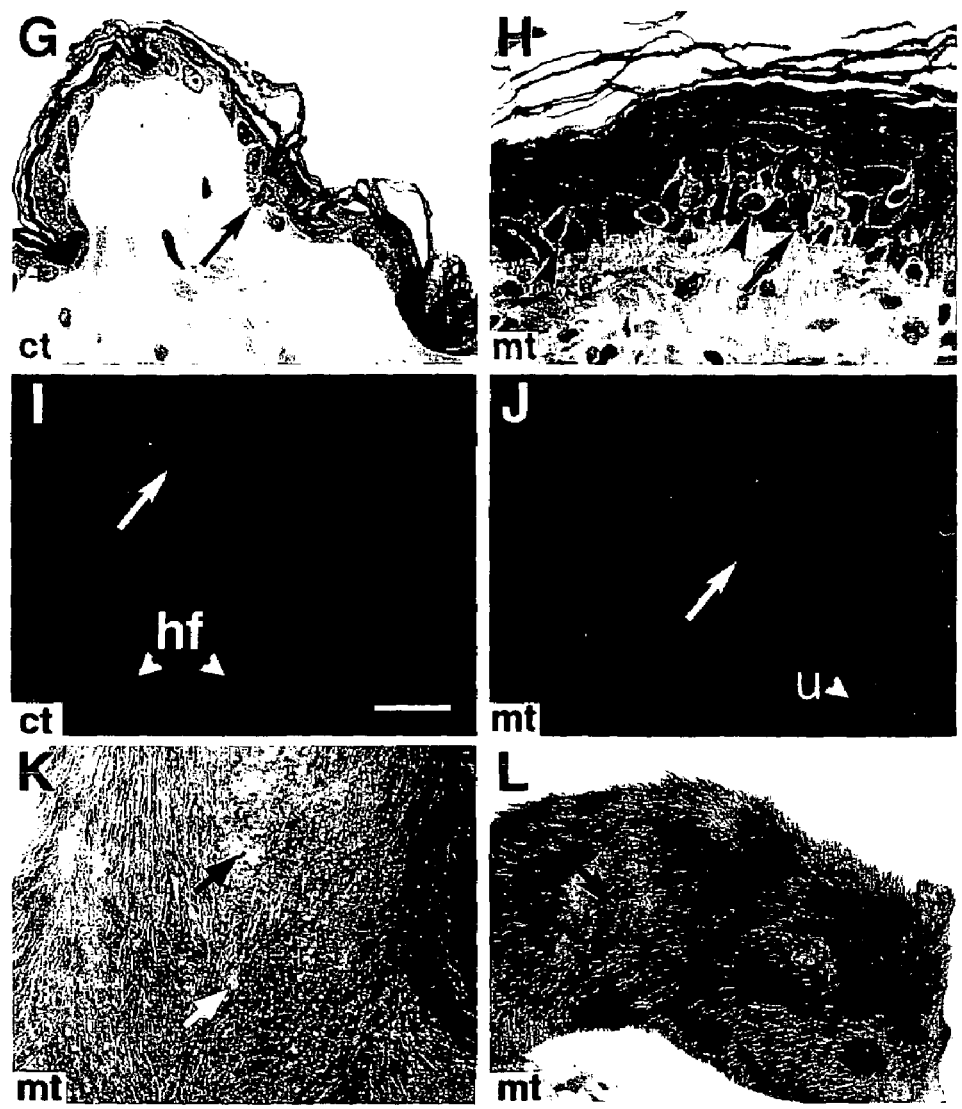

FIG. 2B: Dorsal view of the same animals.

FIG. 2C: Magnification of the ventral region of the "mutant" (mt) female mouse K5-Cre-ER$^{T(tg/0)}$/RXR$_\alpha$$^{L2/−}$, with the arrow indicating one of the cysts visible under the surface of the skin.

FIG. 2D: Dorsal view of the "mutant" (mt) female mouse K5Cre-ER$^{T(tg/0)}$/RXR$_\alpha$$^{L2/−}$, twenty-eight weeks after the start of Tamoxifen treatment. The arrow indicates a minor skin lesion.

FIGS. 2E–H: Histological analysis. Histological sections 2 μm thick of the ventral skin of "control" (E and G) and "mutant" (F and H) mice, sixteen weeks after the start of the treatment. Hair follicles (hf), utriculi (u) and dermal cysts (dc) are indicated. The arrow tips in (H) indicate the Langerhan's cells, whose number is increased several fold in the epidermis of the mutant mice. Increased cellularity can be noted in (F) and in (H) in the dermis under the hyperproliferated interfollicular epidermis. Scale (in E) E and F=60 μm; G and H=12 μm.

FIGS. 2I, J: Immunohistochemistry of keratin 6 (K6) on sections of skin of "control" mice (I) and of "mutant" mice (J), sixteen weeks after the first Tamoxifen treatment. The red color corresponds to the labeling with the antibody directed against K6, and the Cyan color corresponds to staining with DAPI. K6 is normally expressed in the outer root sheath of the hair follicle (hf) but not in the epidermis (T) and is abnormally expressed in the hyperproliferative epidermis of "mutant" mice (J). Scale (in I) I=25 μm. The arrows in E to J indicate the dermis-epidermis junction.

FIGS. 2K, L: Appearance of the skin of a mutant female mouse K14-Cre-ER$^{T2(tg/0)}$/RXR$_\alpha$$^{L2/L2}$. (K) magnification on the ventral region, sixteen weeks after the start of Tamoxifen treatment (0.1 mg per injection); the white arrow indicates a cyst and the black arrow indicates a utriculus containing melanosomes. (L) dorsal view of the same mutant. The arrow indicates one of the skin lesions associated with a hairless region.

Figure 3:
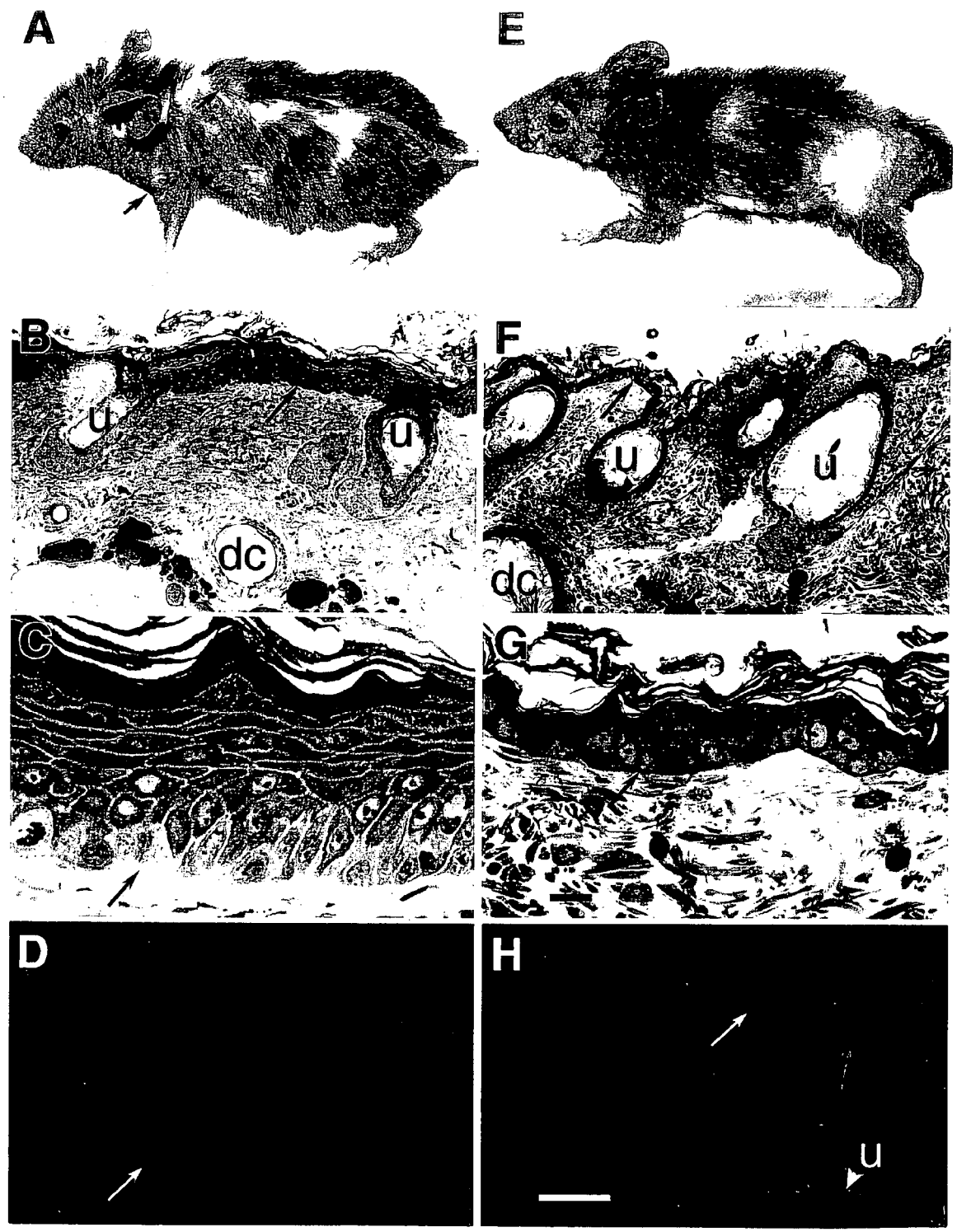

FIG. 3: Similarities and differences between the skin abnormalities present in a double "mutant" mouse K5-Cre-ER$^{T(tg/0)}$/RXR$_\alpha$$^{L2/L2}$/RXR$_\beta$$^{−/−}$ induced with Tamoxifen and a "null" VDR mouse.

FIGS. 3A, E: K5-Cre-ER$^{T(tg/0)}$/RXR$_\alpha$$^{L2/L2}$/RXR$_\beta$$^{−/−}$ mouse eighteen weeks after the first treatment with Tamoxifen (1 mg of Tamoxifen per injection) (A) and fourteen-week old VDR$^{−/−}$ mouse (E). The arrows in (A) indicate the skin lesions. (B, C) and (F, G): histological analysis of 2 μm thick sections of dorsal skin of the animals presented in (A) and (E) respectively. Scale (in G): B and F=60 μm; C and G=12 μm.

FIGS. 3D, H; Immunohistochemistry of keratin 6 (K6) on mouse skin sections removed from the animals presented in (A) and (E) respectively. It should be noted that K6 is expressed in the utriculus, but not in the epidermis of the skin of the VDR$^{−/−}$ mice, whereas K6 is expressed in the entire hyperproliferative epidermis of the "double mutant" mice RXR$_\alpha$/RXR$_\beta$ (D). Utriculus (U), dermal cyst (dc). The arrows in (B-H) indicate the dermis-epidermis junction. Scale (in H): D and H=25 μm.

FIG. 4: Selected targeted inactivation of the SNF2β gene in the epidermis of adult mice.

Figure 4A:
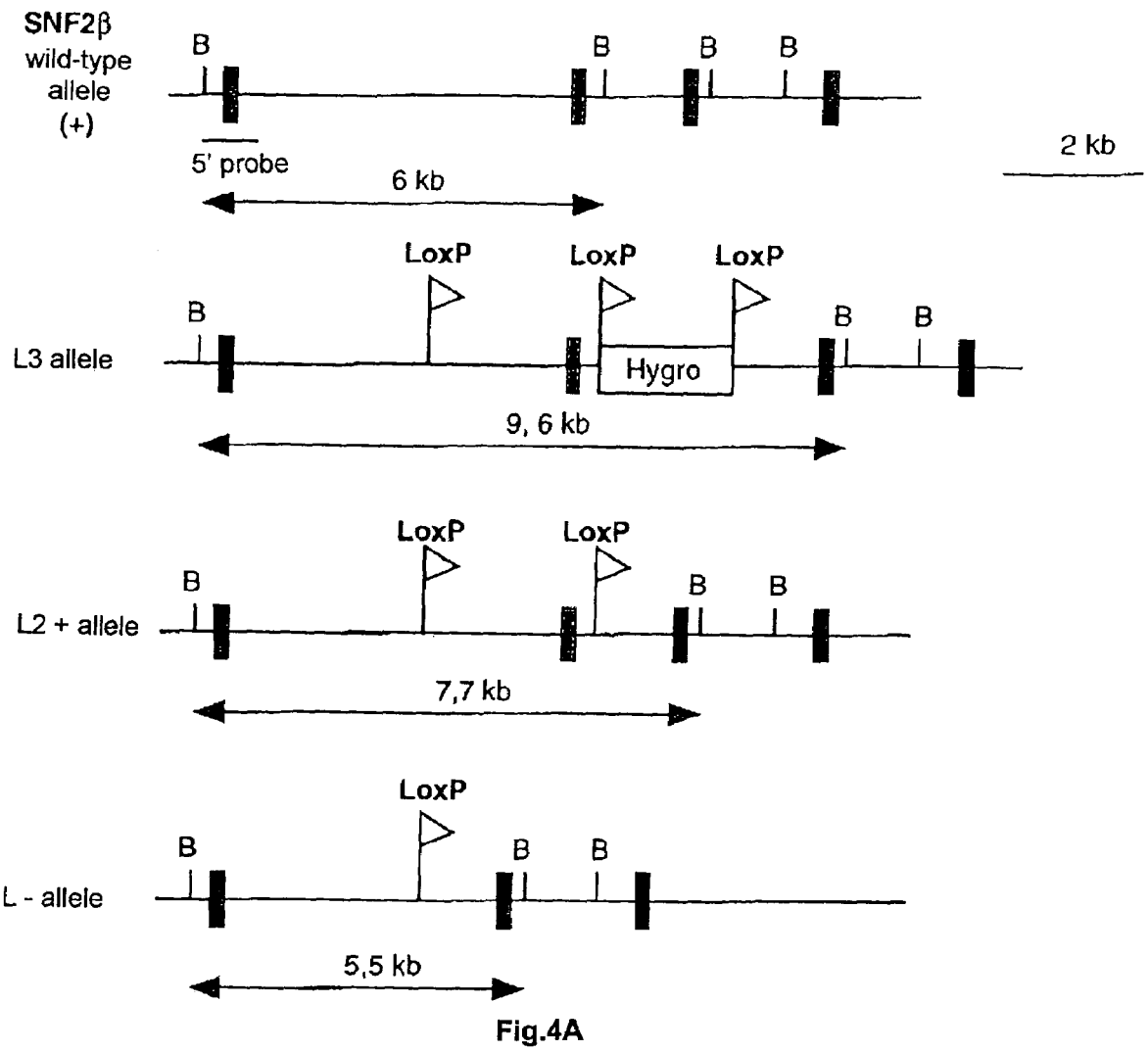
Figure 4B:
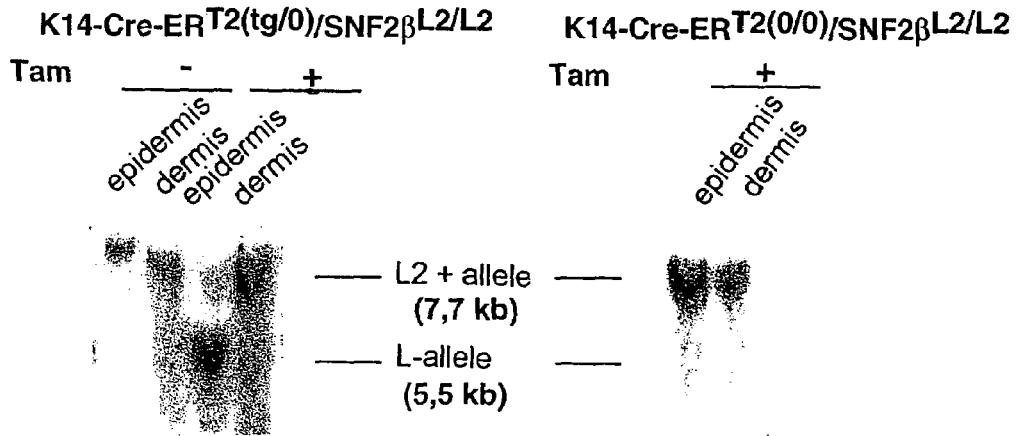

FIG. 4A: Schematic representation of the wild-type SNF2β alleles (+), L3, L2+ and L−.

The size of the DNA segments revealed by the 5' probe, after enzymatic digestion of the genomic DNA by BamHI is indicated. The L3 allele in the ES cells was obtained by homologous recombination using a strategy similar to that described for the F9 cells in Sumi-Chinose et al., 1997.

FIG. 4B

Eight-week old K14-Cre-ER$^{T2(tg/0)}$/SNF2β$^{L2/L2}$ and K14-Cre-ER$^{T2(0/0)}$/SNF2β$^{L2/L2}$ were treated with Tamoxifen (Tam) for five days at the rate of 0.1 mg/day or with oil (−). Tail biopsis were taken, the dermis and the epidermis separated, the genomic DNA prepared, digested with BamHI, separated by agarose gel electrophoresis, and transferred onto nylon membranes, which were hybridized with the radiolabeled 5' probe. Autoradiographs are presented.

Figure 5:
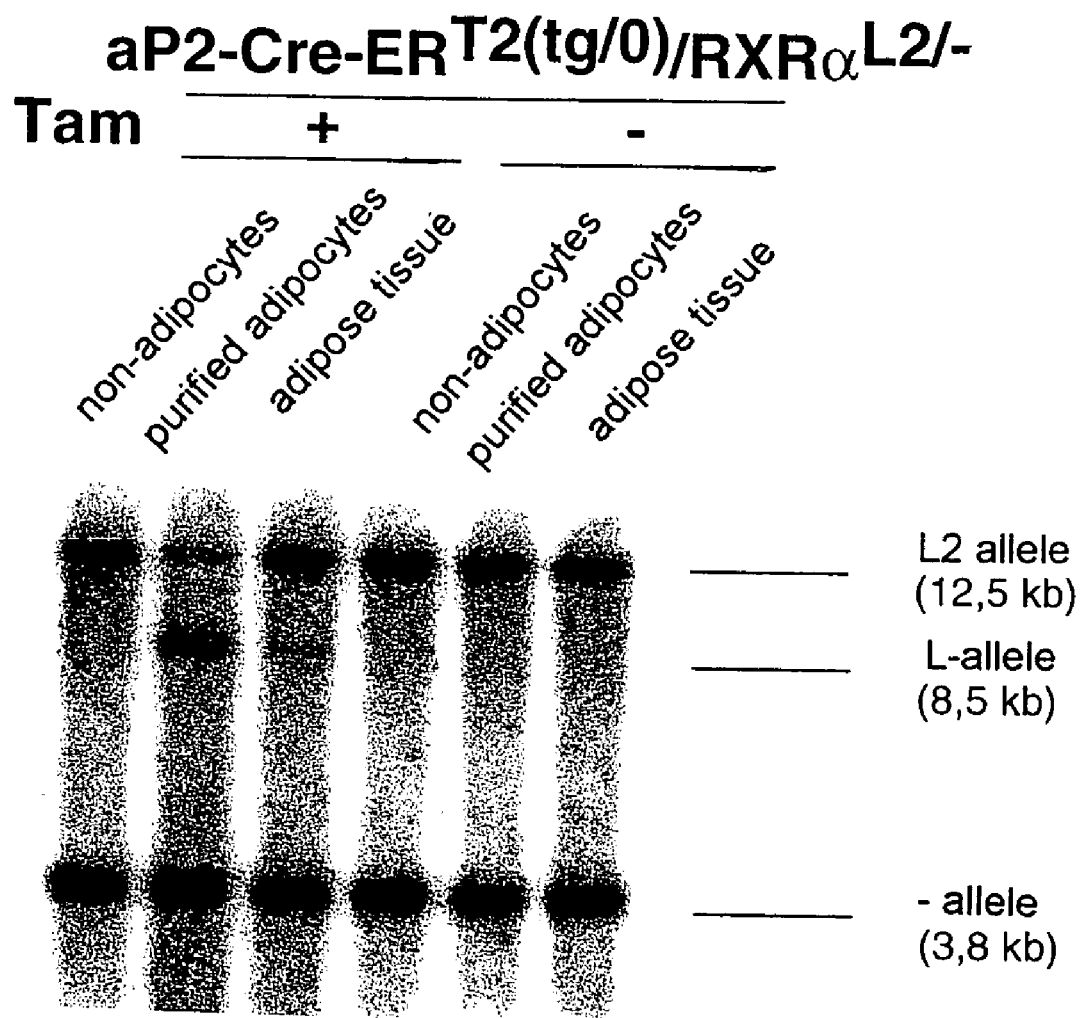

FIG. 5: Selective targeted inactivation of the RXR$_\alpha$ gene in the adipocytes.

Transgenic aP2-Cre-ER$^{T2/(tg/0)}$ mice expressing Cre-ER$^{T2}$ under the control of the laurine aP2 promoter, which is selectively active in the adipocytes (Ross et al., 1990), were crossed with RXR$_\alpha$$^{L2/+}$ mice so as to produce aP2-Cre-ER$^{T2(tg/0)}$/RXR$_\alpha$$^{L2/L2}$ mice.

These mice were then crossed with RXR$_\alpha$$^{+/−}$ mice (Kastner et al., 1994) so as to produce aP2-Cre-ER$^{T2(tg/0)}$/RXR$_\alpha$$^{L2/−}$ mice. Such four week old mice, were treated (+) or not (−) with Tamoxifen (1 mg/day) for five days, and the adipose tissue collected one month after the last injection of Tamoxifen. The DNA was extracted from the adipose tissue, or after separation of the adipocytes (80% purified adipocytes) from the connective tissue and blood vessels (nonadipocytes). After digestion with BamHI, the alleles of RXR$_\alpha$ were analyzed by Southern blotting. An autoradiogram is presented. No excision is observed in the purified adipocytes or the adipose tissue of mice not treated with Tamoxifen (Tam). On the other hand, in the adipose tissue and the adipocytes of mice treated with Tamoxifen, excision is observed which is characterized by the appearance of a band at 8.5 kb corresponding to the L⁻ allele.

FIG. 6: Phenotypic analysis of mice after conditional somatic mutagenesis of RXR$_\alpha$ in the adipocytes.

The weight of the control mice aP2-Cre-ER$^{T2(tg/0)}$RXR$_\alpha$$^{L2/+}$ (CT) and aP2-Cre-ER$^{T2(tg/0)}$/RXR$_\alpha$$^{L2/−}$ (mutants; KO) was determined once per week. (A) each group of animals was composed of 10 to 15 males. The animals were-red either with the normal food (AN) or food enriched with fat and with glucose (AR). (B) The weight of the subcutaneous adipose tissue of 6-month old CT and KO mice, fed with AN or AR. (C) 10 μm cryosections of subcutaneous adipose tissue of 6-month old CT (a and c) and KO (b and d) mice, fed with AN (a and b) or AR (c and d). Scale; 160 μm. The levels of triglycerides (D), glucose (E) and insulin (F) were determined on the serum of 4- to 5-month old CT and KO animals, fed with AN or AR. The glucose assay was carried out after starving the animals for 12 hours, p<0.05.

Figure 7:
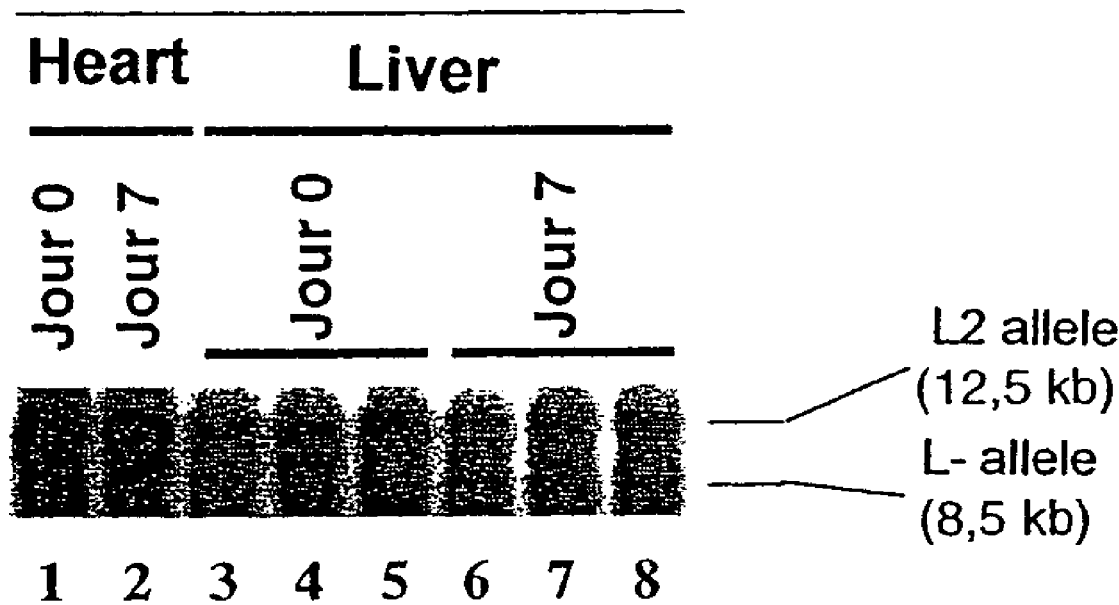

FIG. 7: Selective targeted inactivation of the RXR$_\alpha$ gone in the murine hepatocytes.

To invalidate the RXR$_\alpha$ gene selectively in the hepatocytes, $\alpha$AT-Cre-ER$^{T(tg/0)}$ mice which express Cre-ER$^T$ under the control of the promoter of the $\alpha$-1-antitrypsin ($\alpha$AT) gene in about 50% of the hepatocytes (Imaï et al., 2000) were crossed with RXR$_\alpha^{L2/L2}$ mice so as to produce $\alpha$AT-Cre-ER$^{T(tg/0)}$/RXR$_\alpha^{L2/L2}$ mice. Such three month old mice were treated with Tamoxifen (1 mg/day) for five days, and the heart and liver removed seven days after the first injection of Tamoxifen (day 7), from one and three animals respectively. The heart and the liver were also removed from one and three animals respectively of the same genotype without treatment with Tamoxifen (Day 0). The DNA was extracted from these tissues, and after digestion with BamHI, the alleles of RXR$_\alpha$ were analyzed by Southern blotting. An autoradiogram is presented No excision is observed in the heart at day 0 or 7, or in the liver at day 0. Conversely, excision is observed in the liver of mice seven days after the treatment with Tamoxifen; this excision is materialized by the appearance of a band at 8.5 kb on the autoradiogram, corresponding to the L$^-$ allele.

Figure 8:
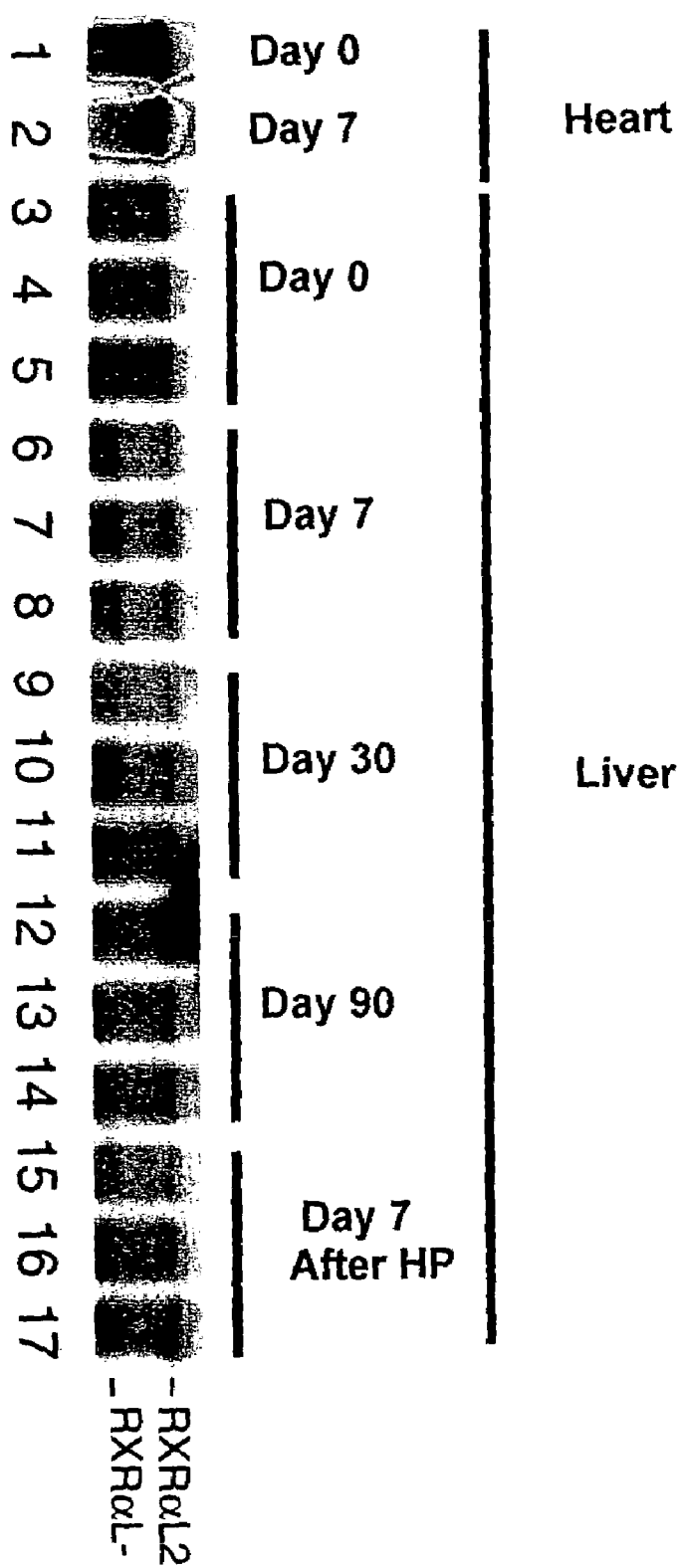

FIG. 8: Site-specific recombination of RXR$_\alpha$ in the liver.

The excision of DNA segments mediated by Cre-ER$^T$ was determined by "Southern blotting", carried out with DNA extract from the heart and the liver of $\alpha$At-Cre-ER$^{T(tg/0)}$/RXR$_\alpha^{L2/L2}$ mice, removed from various animals before the injections of tamoxifen (day 0) or 7, 30 or 90 days after the last injection of Tamoxifen.

Lanes 15–17 correspond to the DNA isolated from the livers of animals 7 days after partial hepatectomy (HP), carried out after the injection of Tamoxifen. The position of the RXR$_\alpha$L2 and L- alleles is indicated.

Figure 9:
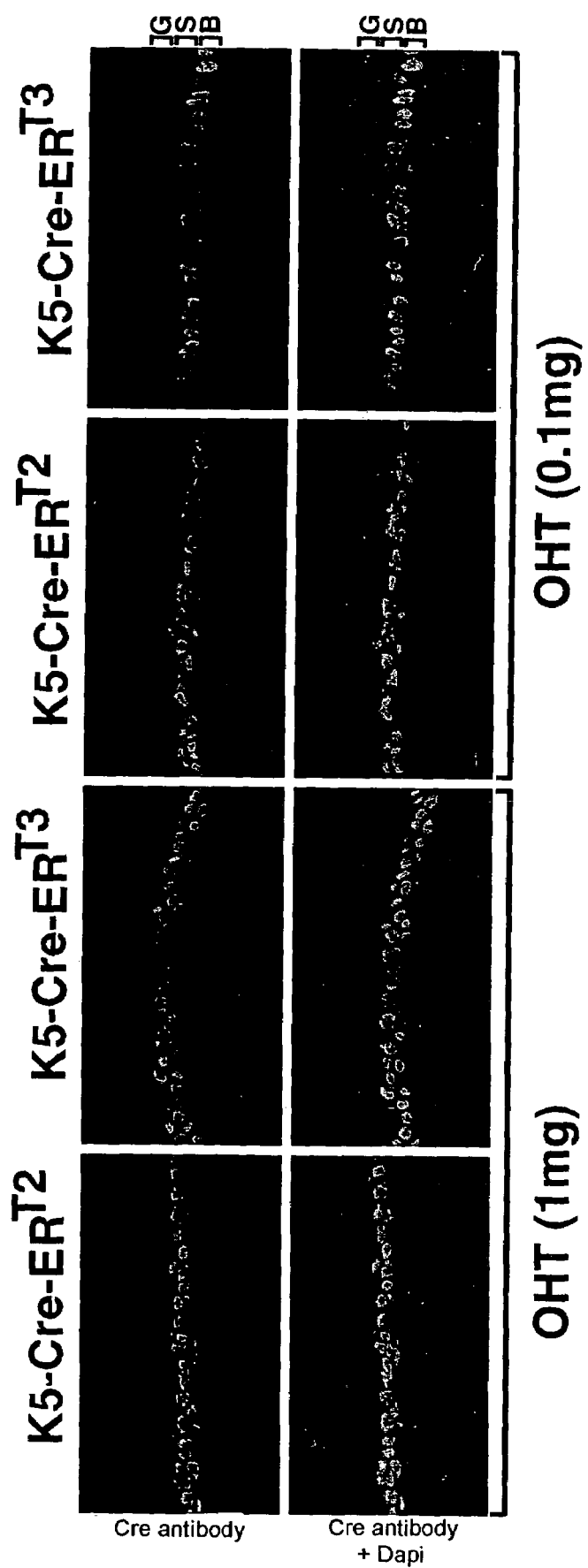

FIG. 9: Expression of the Cre-ER$^{T2}$ and Cre-ER$^{T3}$ recombinases in the basal layer of the epidermis.

Immunohistochemistry of the chimeric Cre recombinase on sections of the epidermis of K5-Cre-ER$^{T2}$ and K5-Cre-ER$^{T3}$ mice, treated either with 1 mg or 0.1 mg of OHT (4-hydroxyTamoxifen). The red color corresponds to labeling with the anti-Cre antibody directed against the Cre recombinase protein, and the Cyan color corresponds to DAPI staining the cellular nuclei. Cre-ER$^{T2}$ and Cre-ER$^{T3}$ are located in the cellular nuclei of the basal layer. (It should be noted that the superpositon of the red and cyan colors results in a violet coloration).

Figure 10:
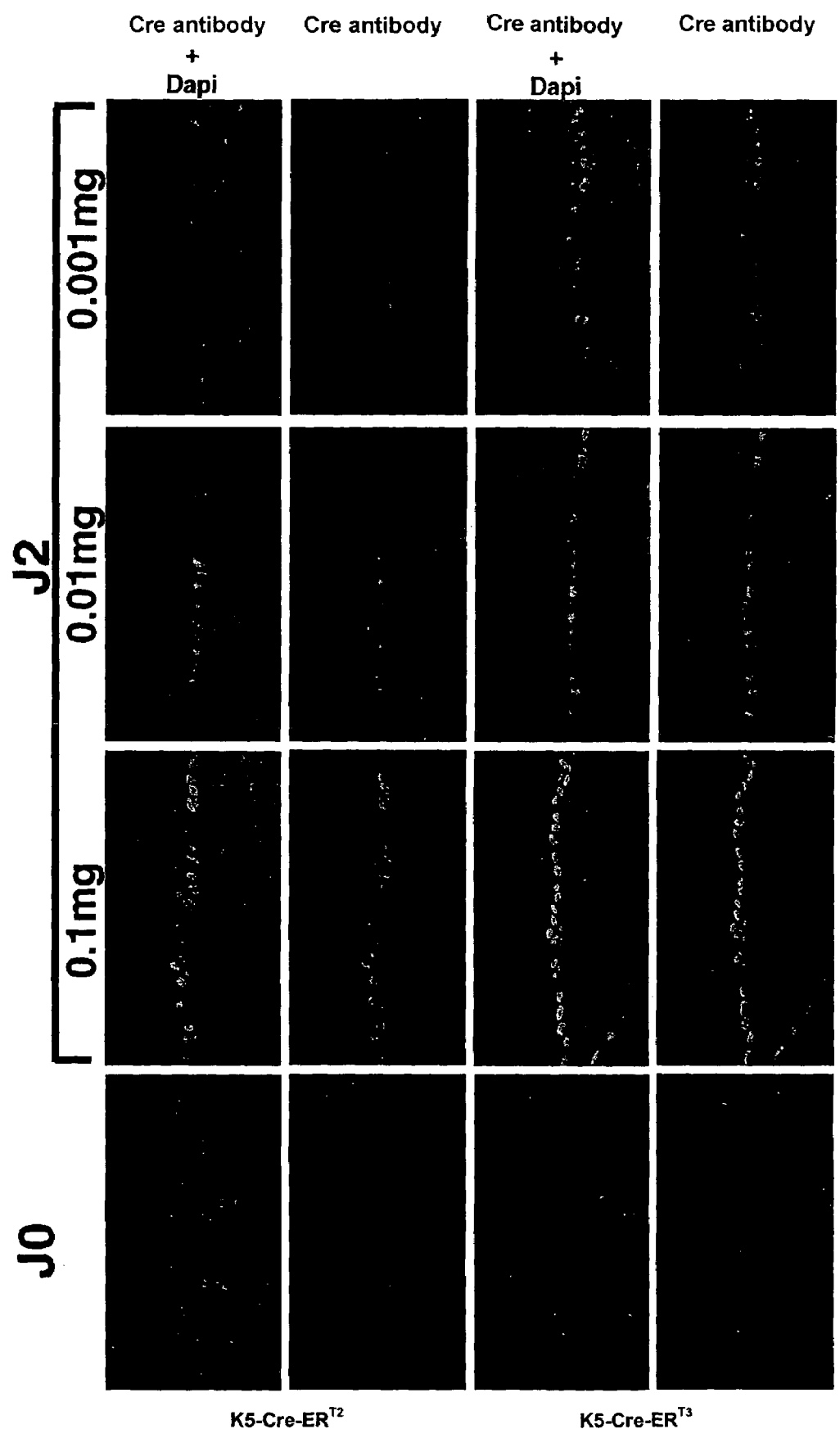

FIG. 10: Nuclear translocation of Cre-ER$^{T2}$ and Cre-ER$^{T3}$ following a two-day treatment at various OHT doses.

Immunohistochemistry of the chimeric Cre recombinase on sections of the epidermis of K5-Cre-ER$^{T2}$ and K5-Cre-ER$^{T3}$ mice treated either with 0.1 mg, 0.01 mg or 0.001 mg of OHT and analyzed two days (D 2) after the start of the treatment (D 0). The red color corresponds to labeling with the anti-Cre antibody directed against the Cre protein, and the Cyan color corresponds to DAPI. Cre-ER$^{T2}$ and Cre-ER$^{T3}$ are located in the cellular nuclei of the basal layer, Cre-ER$^{T3}$ is present in a larger fraction thereof than Cre-ER$^{T2}$, at the various OHT doses. At the dose of 0.001 mg, about ⅓ of the nuclei are strongly labeled with anti-Cre antibodies in the basal layer of the epidermis of K5-Cre-ER$^{T3}$ mice, whereas no positive nucleus is observed in the skin of K5-Cre-ER$^{T2}$ mice. (It should be noted that this superposition of the red and cyan colors results in a violet coloration).

Figure 11:
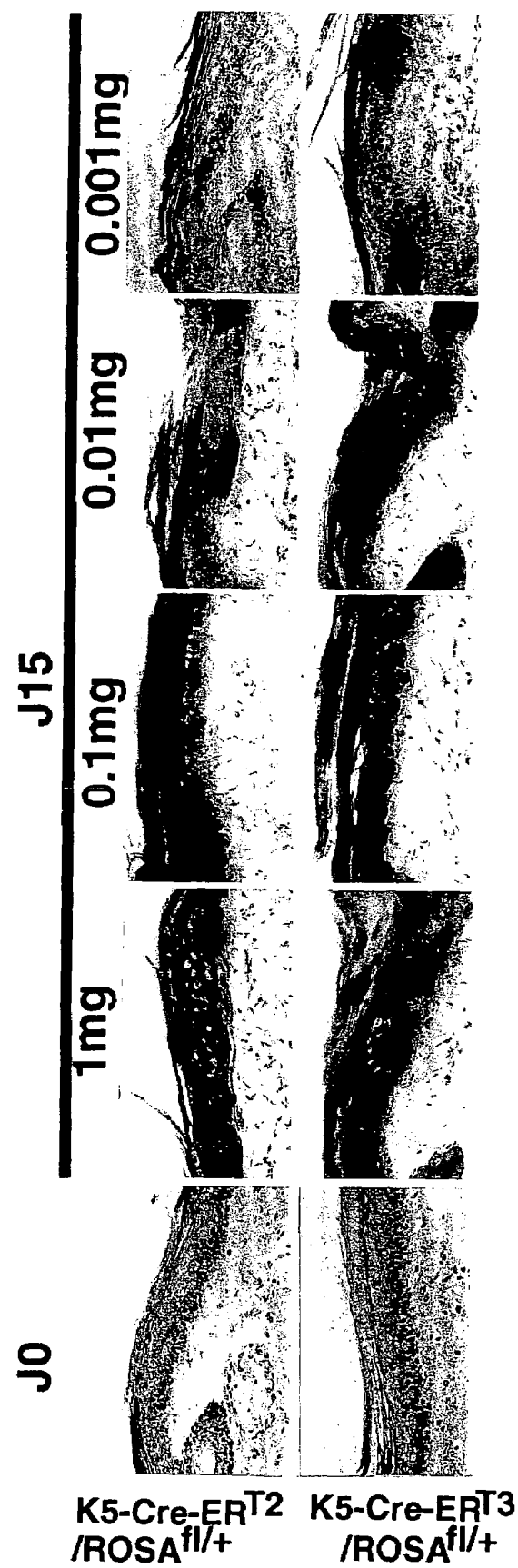

FIG. 11: Comparison of the expression of $\beta$-galactosidase in the epidermis of the tail of K5-Cre-ER$^{T2(tg/0)}$/Rosa$^{fl/+}$ and K5-Cre-ER$^{T3(tg/0)}$/Rosa$^{fl/+}$ induced by various OHT doses.

Activity of $\beta$-galactosidase on sections of the epidermis of the tail of K5-Cre-ER$^{T2(tg/0)}$/Rosa$^{fl/1}$ and K5-Cre-ER$^{T3(tg/0)}$/Rosa$^{fl/+}$ mice treated with 1 mg, 0.1 mg, 0.01 mg and 0.001 mg of QHT. The analyses are carried out on the fifteenth day after the start of the treatment (D0).

The excision levels induced by 1 and 0.1 mg of OHT are similar for the two lines; on the other hand, the excision is more efficient in the K5-Cre-ER$^{T3}$ than in the K5-Cre-ER$^{T2}$ mice at the doses of 0.01 and 0.001 mg of OHT.

FIG. 12: Rate of papilloma formation in RXR$\alpha^{ep-/-}$ mice.

A. Timing of Tam-induced RXR$\alpha$ ablation in epidermal keratinocytes, and DMBA/TPA tumorigenesis. Tam-treatment (0.1 mg for 5 consecutive days) was performed either 16 days before (bar a) or 7 weeks after (bar b) topical DMBA application. TPA was topically applied twice a week (arrows) for up to 30 weeks. B. Papillomas in DMBA/TPA-treated RXR$\alpha^{ep-/-}$ mice. The number of papillomas induced by the DMBA/TPA treatment was determined macroscopically in 6 CT and 6 RXR$\alpha^{ep-/-}$ mice, and plotted versus the number of weeks after the start of the carcinogenic treatment. Values are expressed as mean +/–SEM C. Dorsal view of CT (K14-Cre-ER$^{T2(0/0)}$/RXR$\alpha^{L2/L2}$) (left) and RXR$\alpha^{ep-/-}$ (right) mice 25 weeks after the start of the DMBA/TPA treatment. D. Length distribution of papillomas in CT and RXR$\alpha^{ep-/-}$ mice. The number of tutors of a given length was determined on 6 CT and 6 RXR$\alpha^{ep-/-}$ mice, 30 weeks after the start of the DMBA/TPA treatment. Values are expressed as mean +/–SEM.

FIG. 13: Histological analysis of skin tumors induced by DMBA/TPA treatment.

A. Representative hematoxylin and eosin stained 5 µm-thick paraffin sections from CT biopsies taken 25 (a-b) and 30 (c) weeks after the start of the DMBA/TPA treatment, B. Representative hematoxylin and eosin stained 5 µm-thick paraffin sections from RXR$\alpha^{ep-/-}$ biopsies taken 25 (a-c) and 30 (d-i) weeks after the start of the DMBA/TPA treatment. (a), atypical hyperplasia; (b), in situ carcinoma; (c), focal carcinoma; (d), (e), (f) and (g), advanced grade I, II, III and IV SCC, respectively; (h), spindle cell carcinoma; (i), basal cell carcinoma. Scale bar 33 µm. C. Table of histological analysis of paraffin sections (5 µm-thick) of biopsies of 8–16 mm tumors from CT and RXR$\alpha^{ep-/-}$ mice, 25 and 30 weeks after the start of the DMBA/TPA treatment.

FIG. 14: Melanocytic growths induced by DMBA treatment of CT and RXR$\alpha^{ep-/-}$ mice.

A. Dorsal view of CT (K14-Cre-ER$^{T2(0/0)}$/RXR$\alpha^{L2/L2}$) (left) and RXR$\alpha^{ep-/-}$ (right) mice 25 weeks after DMBA treatment. Arrows point to some or the melanocytic growths. B. Number of melanocytic growths in skin of CT and RXR$\alpha^{ep-/-}$ mice 30 weeks after DMBA and DMBA/TPA treatments, as indicated. Values are expressed as mean +/–SEM (n=6). *, p<0.05; ***, p<0.001, C. Size distribution of melanocytic growths in CT and RXR$\alpha^{ep-/-}$ mice. The number of 1–2 and 2–4 mm melanocytic growths was determined on CT and RXR$\alpha^{ep-/-}$ mice, 30 weeks after DMBA and DMBA/TPA treatments, as indicated. Values are expressed as mean +/–SEM (m=6).

Figure 15:
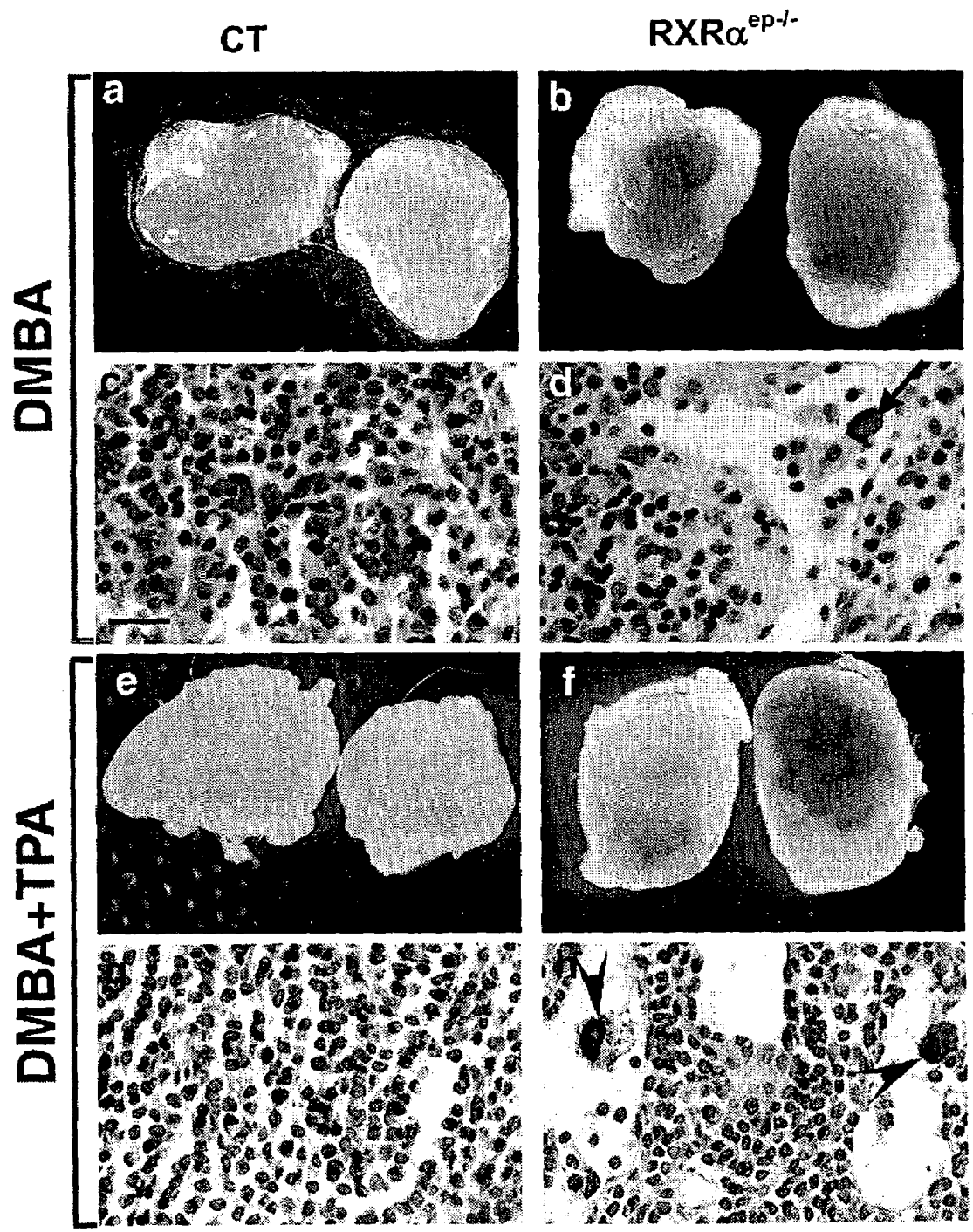

FIG. 15: Malignant melanomas in lymph nodes of DMBA-treated RXR$\alpha^{ep-/-}$ mice.

Photograph of subiliac lymph nodes from CT (a and e) and RXR$\alpha^{ep-/-}$ (b and f) mice taken 30 weeks after DMBA and DMBA/TPA treatment, respectively. Hematoxylin and eosin stained 5 µm paraffin sections of CT (c and g) and RXR$\alpha^{ep-/-}$ (d and h) mice after DMBA and DMBA/TPA treatments, respectively. Scale bar, 33 µm.

EXAMPLES

1) Materials and Methods

1.1—Transgenic lines

The mouse lines $RXR_\alpha^{+/+}$, $VDR^{-/-}$ and K5-Cre-$ER^T$ have been previously described in Yoshizawa et al. (1997), Kastner et al. (1994) and Indra et al. (1999).

The transgene K14-Cre-$ER^{T2}$ was constructed by replacing the K5 promoter region of the vector pK5-Cre-$ER^{T2}$ (Indra et al., 1999) with the SalI DNA fragment of the promoter/enhancer region of 2 kb of the K14 human keratin gene, isolated from Phr2 (gift from S. Werner). The transgenic mice were generated in accordance with the article by Indra et al. (1999)

The transgene aP2-Cre-$ER^{T2}$ was constructed as follows, a 5.4 kb fragment containing the aP2 promoter was amplified by PCR from mouse genomic DNA with the aid of the LA-PCR kit (Perkin-Elmer, New Jersey), with the oligonucleotides

```
5'-ATACGCGGCCGCGAATTCCAGCAGGAATCAGGTAGCT-3'  (Sequence ID No. 13) and

5'-ATAGCGCCGGCGCTGCAGCACAGGAGGGTGCTATGAG-3'  (Sequence ID No. 14).
```

After having made the ends of this fragment blunt following the action of T4 polymeraze, it was cloned at the level of the SalI site of pGS-Cre-$R^{T2}$ (Indra et al., 1999), whose ends have also been made blunt following the action of T4 polymerase. The 8.3 kb NotI fragment was isolated from this plasmid, purified and injected into the F1 zygotes (C57BL/6×SJL) at the concentration of 4 ng/ml, and the mice carrying the transgene aP2-Cre-$ER^{T2}$ were identified according to Feil et al., (1996) and Imai et al., (2000).

1.2—Genotyping of the $RXR_\alpha$ alleles

The genomic DNA is isolated from tissues according to the protocol described in the article by Indra et al. (1999).

The epidermis is separated from the dermis after treating the skin of the tail with the enzyme dispase (4 mg/ml in PBS, GIBCO-BRL) for 1 to 2 hours at room temperature. The genotyping of the $RXR_\alpha$ cells is carried out by PCR (polymerase chain reaction) using the primers ZO 243 (5'-TCC TTC ACC AAG CAC ATC TG-3') (SEQ ID No. 9) (located in exon 3) and ZO 244 (5'-TGC AGC CCT CAC AAC TGT AT-3') (SEQ ID No. 10) (located in exon 4) for the L2 and wild-type (+) alleles; these amplification reactions generate, for the L2 allele, a fragment of 700 bp and for the wild-type (+) allele a fragment of 650 bp.

The primers ZO 243 and UD 196 (5'-CAA CCT GCA CTT GTC ACT TAG-3') (SEQ ID No. 11) (located in the intron between exons 4 and 5) were used in the polymerase chain reaction to reveal the $L^-$ allele; this amplification reaction generates a fragment of 400 bp.

The primers ZO 243 and RU 178 (5'-ATG TTT CAT AGT TGG ATA TC-3') (SEQ ID No. 12) (located in the neo cassette) are used in the polymerase chain reaction to reveal the (−) allele; this PCR reaction generates a fragment of 500 bp.

For the analyses using DNA transfer (Southern blotting), the genomic DNA is digested with BamHI and the probe used is the probe X4 (3 kb BamHI-XbaI fragment of the $RXR_\alpha$ gene) (Metzger et al., 1995).

1.3—Treatment with Tamoxifen

Tamoxifen (Sigma) solutions are prepared according to the protocol described by Metzger and Chambon (2001). 1 mg of Tamoxifen dissolved in 100 µl of sunflower oil is intraperitoneally injected into a transgenic mouse K5-Cre-$ER^T$ for five consecutive days, and then again for three consecutive days, two, four and six weeks later. The K14-Cre-$ER^{T2}$ transgenic mice are intraperitoneally injected with 0.1 mg of Tam dissolved in 100 µl of sunflower oil for five consecutive days, while the aP2-Cre-$ER^{T2}$ and αAT-Cre-$ER^T$ mice are treated with 1 mg of Tam.

1.4—Histological analyses

The skin biopsies from animals of the same age and of the same sex were prepared at the level of the same sites of the body.

The skin samples are fixed in glutaraldehyde (2.5% in 0.1 M cacodylate buffer pH 7.2) overnight at 4° C. and then post-fixed with 1% osmium tetroxide in a cacodylate buffer for 1 hour at 4° C. the tissues are dehydrated with increasing concentrations of alcohol and then covered with EPON 812. Semithin sections of 2 µm are then stained with toluidine blue.

1.5—Immunochemistry

After fixing in 2% paraformaldehyde, frozen sections of 10 µm are blocked in 5% normal goat serum (Vector Laboratories) incubated with the rabbit polyclonal antibody anti-MK6 (Babco). After washing in PBS/0.1% Tween 20, the sections are incubated with the donkey anti-rabbit IgG antibody conjugated with CY3 (Jackson Immuno Research) and then mounted in the Vectashield medium (Vector Laboratories) containing DAPI (4',6-diamidino-2-phenylindole dihydrochloride; Boehringer Mannheim) (Brocard et al., 1997). The anti-Cre antibodies are used according to Indra et al. (1999).

1.6—Immunohistochemistry

Tumors (6–16 mm) were excised 22 weeks after DMBA application and immediately embedded in OCT and frozen on dry ice. 10 µm-thick frozen sections from CT and $RXR_\alpha^{ep-/-}$ tumors were reacted with primary antibodies [mouse monoclonal anti-X10, rabbit polyclonal anti-K5 (gifts from Prof. Brigitte Lane, Cell Structure research group, University of Dundee), rabbit polyclonal anti-X1 (Babco), rabbit polyclonal anti-K13 (gift from Prof. S. Yuspa, NIH), rabbit polyclonal α6-integrin, biotin-conjugated rat monoclonal anti-CD31 (Pharmingen)], and revealed with either CY3-conjugated donkey anti-rabbit, CY3-conjugated goat anti mouse IgG antibodies or CY3-streptavidine (Jackson Immunoresearch). Counterstaining was performed with DAPI (4',6-diamidino-2-phenylindole dihydrochloride, Boehringer Mannheim).

1.7—Histology

The adipose tissue samples are removed from animals perfused with PFA, fixed with the aid of formaldehyde (20% in PBS) and then frozen in OCT (Tissue-Tek compound, Sakura). Cryosections of 10 µm are stained with hematoxylin and eosin.

The liver is removed from animals, rinsed in PBS, fixed in a Boin solution and then embedded in paraffin, Sections of 6 µm are stained with hematoxylin and eosin.

Tumors from 25 animals were excised at 25 or 30 weeks after DMBA application, fixed in Bouin's fixative and embedded in paraffin. 5 µm sections were stained with hematoxylin and eosin. Electron microscopy was performed as described (Li et al., 2001).

Subiliac lymph nodes were isolated 30 weeks after DMBA application, fixed in 4% paraformaldehyde, photographed and embedded in paraffin. 5 µm-thick sections were stained with hematoxylin and eosin.

1.8—Assay of blood parameters

The assay of the triglycerides and of cholesterol is carried out according to Peters et al. (1997), with Boehringer Mannheim reagents. The assays of insulin and of glucose are carried out with the Crystal Chem Inc. and glucofilms kit (Bayer Corp, USA) respectively.

1.9—Treatments with carcinogenic agents

Skin papillomas and carcinomas were chemically induced by the two-stage carcinogenesis schedule. A single dose of 7,12-dimethylbenz(a)anthracene (DMBA) (5 µg in 100 µl acetone) was applied on the dorsal skin of 10–14 week old mice, 7 weeks before or 16 days after the first Tam or oil (vehicle) treatments. 12-0-tetradecanoylphorbol-13-acetate (TPA) (5 µg in 200 µl acetone) was applied twice a week for 25 to 30 weeks, starting one week after DMBA application. CT and $RXR\alpha^{ep-/-}$ mice were shaved 7 and 2 days before DMBA treatment, and every second week for 30 and 15 weeks, respectively. 8 weeks after DMBA treatment, all-trans retinoic acid (t-RA, 20 nmoles in ethanol) or vehicle was topically applied 15 min before each TPA application.

1.10—Determination of the number and size of the tumors

The length of the papillomas and the diameter of the melanocytic were measured with a Vernier calliper on isofluorane anesthesised mice.

1.11—Statistical analyses

Values are reported as mean ±SEM. Statistical significance (p<0.05) was determined by unpaired Student's test (Statview, Abacus Concepts, CA).

2) First Example

Targeted Inactivation of the $RXR_\alpha$ Gene in the Epidermis of Adult Mice.

To inactivate $RXR_\alpha$ in the epidermis, the inventors constructed a mouse carrying floxed $RXR_\alpha^{L2}$ alleles (FIG. 1A) and used the transgenic mouse line K5-Cre-$ER^T$ in which Tamoxifen (Tam) efficiently induces Cre-mediated recombination in the keratinocytes of the basal layer (Indra et al., 1999). The crossing of the K5-Cre-$ER^{T(tg/0)}$/$RXR_\alpha^{L2/L2}$ mouse with an $RXR_\alpha^{+/-}$ mouse (FIG. 1A) (Kastner et al., 1994) or with an $RXR_\alpha^{L2/+}$ mouse makes it possible to obtain "promutant" (PM) hemizygous (tg/0) mice for the K5-Cre-$ER^T$ transgene which carries either an $RXR_\alpha^{L2}$ allele and a null $RXR_\alpha$ allele (genotype: K5-Cre $ER^{T(tg/0)}$/$RXR_\alpha^{L2/-}$), or two L2 alleles (genotype K5-Cre-$ER^{T(tg/0)}$/$RXR_\alpha^{L2/L2}$). Fourteen-week-old PM mice were treated with Tamoxifen (five days, 1 mg/day), and then treated again two, four and six weeks later. Six to twelve weeks after the first Tamoxifen treatment ("AFT: After First Tamoxifen Treatment"), nearly all the $RXR_\alpha^{L2}$ alleles (>80%) were converted to an $RXR_\alpha^{L-}$ allele in the epidermis isolated from mice carrying a floxed allele (FIG. 1B, lanes 2, 3, 5 and 6) or two floxed alles (FIG. 1B, lanes 1 and 4).

As expected (Indra et al. (1999)), no excision is observed in the mice treated only with the oil which served as a vehicle for Tamixofen; the Cre-mediated excision of exon 4 of $RXR_\alpha$ is in addition restricted to the skin and to the other organs which possess epithelia in which the K5 promoter is active (that is to say: the tongue, the salivary gland, the esophagus, FIG. 1C).

Interestingly, hair loss (alopecia) was observed six to seven weeks after the first treatment with Tamoxifen in the ventral region of the mice; this was not observed in the mice treated with oil alone without Tamoxifen, or in the "control" mice of the same litter treated with Tamoxifen (K5-Cre-$ER^{T(tg/0)}$/$RXR_\alpha^{L2/+}$).

Twelve to sixteen weeks after the first injection, large ventral regions and smaller dorsal regions of the skin of the mice had lost their hair (FIGS. 2A and B) and cysts which grow bigger and which appear over the whole body with time are also visible under the surface of the skin (FIG. 2C).

As the age increases (>twenty weeks after the first injection of Tamoxifen), minor lesions, which are not caused by fights, appear in hairless regions of the skin of the back, of the cheeks and of the posterior face of the ears (FIG. 2D).

Sixteen weeks after the first treatment with Tamoxifen, histology of the hairless ventral and dorsal regions showed degeneration of the hair follicles resulting in the appearance of utriculi and of dermal cysts (Sundberg and King, 1996) (FIG. 2—compare E and F). The interfollicular epidermis is hyperplastic with an increase in the incorporation of BrdU and an increased expression of the proliferation marker Ki67.

Dermal cellularity is increased and the capillaries are dilated (compare FIGS. 2E and 2G with 2F and 2H) below the thickened epidermis, thus reflecting an inflammatory reaction. The keratin 6 (K6), normally expressed selectively in the hair follicle outer root sheath (ORS) is also expressed in the hyperproliferative interfollicular epidermis (FIGS. 2I and J) indicating an abnormality in the terminal differentiation of the keratinocytes (Porter et al., 1998). All these abnormalities are less severe and/or appear much later in the males than in the females.

To increase the efficiency of the recombination mediated by Cre and induced by Tamoxifen, the inventors have constructed transgenic mouse lines K14-Cre-$ER^{T2}$ in which the K14 promoter selective for the basal layer (Vassar et al., 1989) directs the expression of Cre-$ER^{T2}$ whose activity may be induced by a gentler treatment with Tamoxifen (0.1 mg for five days) (Indra et al., 1999).

K14-Cre-$ER^{T2(tg/0)}$/$RXR_\alpha^{L2/L2}$ mice were treated simultaneously with "control", K14-Cre-$ER^{T2(tg/0)}$/$RXR_\alpha^{L2/+}$; K14-Cre-$ER^{T2(0/0)}$/$RXR_\alpha^{L2/+}$ and K14-Cre-$ER^{T2(0/0)}$/$RXR_\alpha^{L2/L2}$ mice obtained from the same litter.

Within two weeks, the $RXR_\alpha^{L2}$ alleles were completely converted to an $RXR_{\alpha L}^-$ alleles in the epidermis (FIG. 1D, lanes 1 and 7), but not in the dermis (FIG. 1D, lanes 2 and 8) of transgenic mice expressing K14-Cre-$ER^{T2}$, thus demonstrating the increased efficiency of Cre-$ER^{T2}$ for mediating, after a Tamoxifen treatment, the selective somatic mutation of floxed $RXR_\alpha$ in the epidermis.

No conversion of L2 to L– appeared in the controls lacking the transgene K14-Cre-$ER^{T2}$ (FIG. 1D, lanes 5, 6, 11 and 12) or not treated with Tamoxifen (FIG. 1D, lanes 3, 4, 9 and 10). Furthermore, 8 weeks after the treatment with Tamoxifen, only the $RXR_\alpha^{L-}$ allele was detected in the epidermis of K14-Cre-$ER^{T2(tg/0)}$/$RXR_\alpha^{L2/L2}$ mice, indicating that $RXR_\alpha$ was excised in the majority, if not all of the stem cells of the epidermis. The inactivation of $RXR_\alpha$ also appears in the other epithelia of other organs in which the K14 promoter is active (Wang et al., 1997) (that is to say the tongue, esophagus, stomach).

From 6 weeks after the start of Tamoxifen treatment, the K14-Cre-$ER^{T2(tg/0)}$/$RXR_\alpha^{L2/L2}$ mice exhibited abnormalities similar to those observed in the K5-Cre-$ER^{T(tg/0)}$/$RXR_\alpha^{L2/L2}$ mice treated with Tamoxifen, that is to say a marked hair loss with visible cysts, while visible focal lesions appear at subsequent stages (FIGS. 2K and L).

The underlying dermal and epidermal histological abnormalities are also similar to those observed above for the K5-Cre-ER$^{T(tg/0)}$/RXR$_\alpha^{L2/L2}$ mice treated with Tamoxifen.

The inactivation of floxed RXR$_\alpha$ in the adult epidermis is obtained more rapidly and with lower doses of Tamoxifen with the K14-Cre-ER$^{T2}$ mice than with the K5-Cre-ER$^T$ mice, but the resulting skin abnormalities are finally similar, in both cases, more severe in the females than in the males.

Interestingly, these abnormalities are also similar to those observed in the K14-Cre$^{(tg/0)}$/RXR$_\alpha^{L2/L2}$ or K14-Cre$^{(tg/0)}$/RXR$_\alpha^{L2/-}$ mice in which the flexed RXR$_\alpha$ alleles are selectively excised in the epidermis during fetal development, thus leading to inactivation of RXR$_\alpha$ in the keratinocytes of the epidermis and in the hair follicle root sheaths. In fact, after three weeks of age, these "constitutive" and epidermis-specific RXR$_\alpha$ mutants develop progressive alopecia with typical characteristics of degenerated hair follicles, utriculi is and dermal cysts, which may all be attributed to defects in the hair cycle. Furthermore, these mutants also exhibit interfollicular hyperproliferation of the keratinocytes, as well as abnormal terminal differentiation (with expression of K6), and an Increase in the dermal cellularity associated with an inflammatory reaction of the skin.

Although RXR$_\beta$ is expressed in the epidermis of mice, the skin of adult RXR$_\beta^{-/-}$ mutants appears normal (Kastner et al., 1996), thus suggesting functional redundancies between the various RXR$_S$. As expected, K5-Cre-ER$^{T(tg/0)}$/RXR$_\alpha^{L2/L-}$/RXR$_\beta^{-/-}$ and K5-Cre-ER$^{T(Tg/0)}$/RXR$_\alpha^{L2/L2}$/RXR$_\beta^{-/-}$ mice treated with oil (without Tamoxifen) do not exhibit skin abnormalities, whereas after treatment with Tamoxifen, these mice begin to lose their hair 4 weeks after the first treatment with Tamoxifen while large regions of the skin are hairless 16 to 18 weeks after the start of the treatment (compare FIG. 3A with FIG. 2D), Focal lesions of the skin which were not observed in the single RXR$_\alpha$ mutants are also frequently observed in the double RXR$_{\alpha/\beta}$ mutants fourteen to sixteen weeks after the first treatment with Tamoxifen, in particular on the hairless skin of the trunk, behind the ears and behind the mouth (FIG. 3A).

Histology of the hairless skin shows disappearance of the hair follicles and the presence of utriculi and of dermal cysts (FIG. 3B). The epidermis is highly hyperplastic and hyperkeratinized (compare FIGS. 3B and 3C with FIGS. 2E and 2G, and FIGS. 2F and 2H). Abnormal expression of K6 is observed through the whole epidermis (FIG. 3D) and an inflammatory reaction with an increase in cellularity is also observed (FIG. 38B). In the lesioned skin, the epidermis is covered with a crust and is more hyperplastic and hyperkeratinized. The triple mutants K5-Cre-ER$^{T(tg/0)}$/RXR$_\alpha^{L2/L2}$/RXR$_\beta^{-/-}$/RXR$_\gamma^{-/-}$ do not reveal an additional role of RXR$_\gamma$ in the adult skin. Thus, RXR$_\beta$ may partially compensate for the loss of RXR$_\alpha$ function.

Interestingly, the functional redundance is more pronounced in the males than in the females, since the male and female double mutants RXR$_\alpha$/RXR$_\beta$ are affected in a similar manner unlike the single mutants.

Taken together, the preceding results show the efficiency of the Cre-ER$^T$, Cre-ER$^{T2}$ and Cre-ER$^{T3}$ recombinases (see Example 5 and FIGS. 9, 10 and 11) for generating somatic mutations which are targeted, specific for a cell type and temporally controlled, in adult mouse tissues.

The preceding results also make it possible to demonstrate the use of Cre-ER$^T$-RXRfloxed mice for analyzing and studying the complex biological function of the various RXR sub-types (RXR$_\alpha$, RXR$_\beta$, RXR$_\gamma$) in a particular tissue, that is to say the epidermis.

This study has thus made it possible to reveal the existence of functional redundancies between RXR$_\alpha$ and RXR$_\beta$, although the role of RXR$_\alpha$ is clearly predominant.

The mechanism of action of the various RXR in the molecular events which lead to alopecia and to abnormalities in the keratinocytes of the epidermis which are deficient in nuclear RXR receptors remains unknown.

Nevertheless, their role as heterodimeric partners of a certain number of nuclear receptors (for example RARs, TRs, VDR, PPARs) which act as signal transducers in various signaling pathways has been suggested in numerous studies in vitro using cells in culture, and confirmed in vivo in some cases using targeted mutagenesis (Chambon, 1996; Mascrez et al., 1998; Wendling et al., 1999). Interestingly, like RXR$_\alpha$, VDR is expressed in the ORS of the hair follicle (Reichrath et al., 1994), and mice in which the two alleles of the VDR gene are inactive (VDR "knock-out" mice) develop progressive secondary alopecia, suggesting that VDR is involved in the hair cycle rather than in primary hair growth (Yoshizawa et al., 1997; Li et al., 1997; Li et al., 1998).

Interestingly, the alopecia developed by fourteen-week-old VDR$^{-/-}$ mice and K5-Cre-ER$^{T(tg/0)}$/RXR$_\alpha^{L2/L2}$/RXR$_\beta^{-/-}$ mice eighteen weeks after their treatment with Tamoxifen appear very similar, although the skin of the VDR$^{-/-}$ mice does hot exhibit the lesions observed on the epidermis of the mice deficient in RXR (compare FIGS. 3A and 3E).

At the histological level, similar utriculi and dermal cysts are observed (compare FIGS. 3B and 3F) but no hyperproliferation of the keratinocytes, or abnormal differenciation revealed by the expression of K6 is observed in the epidermis of the VDR$^{-/-}$ mice (compare FIGS. 3C and 3D with FIGS. 3G and 3H). Thus, the alopecia generated by the selective inactivation of RXR in the keratinocytes of adult mice is thought to reveal a major role of the RXR/VDR heterodimers in the hair follicle cycle.

3) Second Example

Targeted Inactivation of the SNF2β Gene in the Epidermis of Adult Mice

To inactivate the SNF2β gene in the epidermis of adult mice, the inventors constructed a mouse carrying floxed SNF2β alleles (L2+; FIG. 4A) and used the transgenic mouse line K14-Cre-ER$^{T2}$ in which Tamoxifen effectively induces Cre-mediated recombination in the keratinocytes of the basal layer of the epidermis. Eight-week-old K14-Cre-ER$^{T2(tg/0)}$/SNF2β$^{L2/L2}$ and K14-Cre-ER$^{T2(0/0)}$/SNF2β$^{L2/L2}$ mice were treated with Tamoxifen for five days at the rate of 0.1 mg/day or with oil (−). Skin biopsies were taken, the dermis and the epidermis separated, the genomic DNA prepared, digested with BamHI, separated by agarose gel electrophoresis and transferred onto nylon membranes which were hybridized with the radiolabeled 5' probe (FIG. 4A). The corresponding autoradiographs are presented in FIG. 4B. In the absence of Tamoxifen, no excision in the SNF2β gene is observed whether in the dermis or the epidermis of K14-Cre-ER$^{T2(tg/0)}$/SNF2β$^{L2/L2}$ mice. On the other hand, the injection of Tamoxifen into these same mice induces the exicision of the floxed fragment of the SNF2β gene only in the epidermis, because the K14 promoter is active only in this tissue and not in the dermis. As expected, Tamoxifen induces no excision in K14-Cre-ER$^{T2(0/0)}$/SNF2β$^{L2/L2}$ "control" mice whose cells do not contain a Cre-ER$^{T2}$ transgene.

4) Third Example

Targeted Inactivation of the RXR$_\alpha$ Gene in Murine Adipocytes

To carry out the spatiotemporally controlled site-specific mutagenesis in the adipocytes, the inventors created transgenic mice called aP2-Cre-ER$^{T2}$ expressing the Cre-ER$^{T2}$ fusion protein under the control of the promoter of the gene encoding adipose protein 2 (aP2) which is specifically active in the adipocytes (Ross et al., 1990).

To invalidate the RXR$_\alpha$ gene selectively in the adipocytes, the aP2-Cre-ER$^{T2(tg/0)}$ mice were first crossed with RXR$_\alpha^{L2/+}$ mice so as to produce aP2-Cre-ER$^{T2(tg/0)}$/RXR$_\alpha^{L2/L2}$ mice. These mice were then crossed with RXR$_\alpha^{+/-}$ mice (Kastner et al., 1994) so as to produce aP2-Cre-ER$^{T2(tg/0)}$/RXR$_\alpha^{L2/-}$ mice. Such four week old mice were treated (+) or not (−) with Tamoxifen (1 mg/day) for five days, and the adipose tissue collected one month after the last injection of Tamoxifen. The DNA was extracted from the adipose tissue, or after separation of the adipocytes (80%-purified adipocytes) from the connective tissue and blood vessels (non-adipocytes). The DNA is then digested with BamHI and then separated by agarose gel electrophoresis, transferred onto nylon membranes and then hybridized with the radiolabeled X4 probe. The corresponding radiographs are presented in FIG. 5.

In the absence of Tamoxifen, no excision in the RXR$_\alpha$ gene is observed whether in the adipose tissue, the adipocytes or other non-adipocyte cells of the epidermis of aP2-Cre-ER$^{T2(tg/0)}$/RXR$_\alpha^{L2/-}$ mice. On the other hand, the injection of Tamoxifen into such mice induces the excision of the floxed fragment of the RXR$_\alpha$ gene only in the purified adipocytes and the adipose tissue.

Figure 6A:
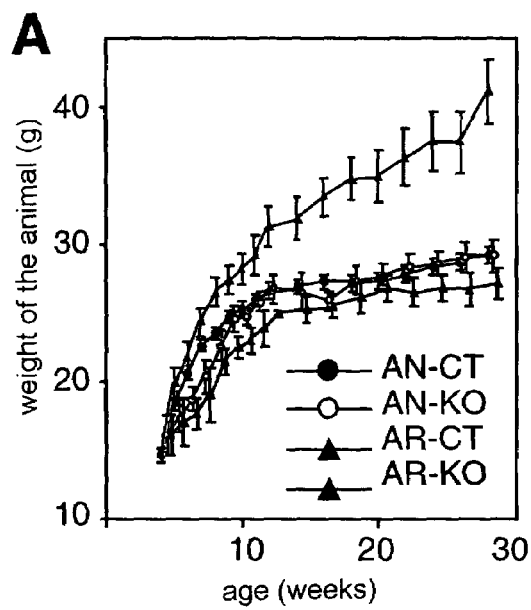
Figure 6B:
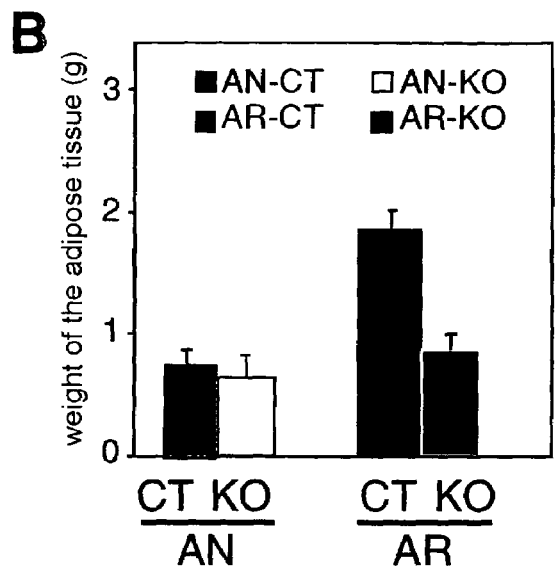
Figure 6C:
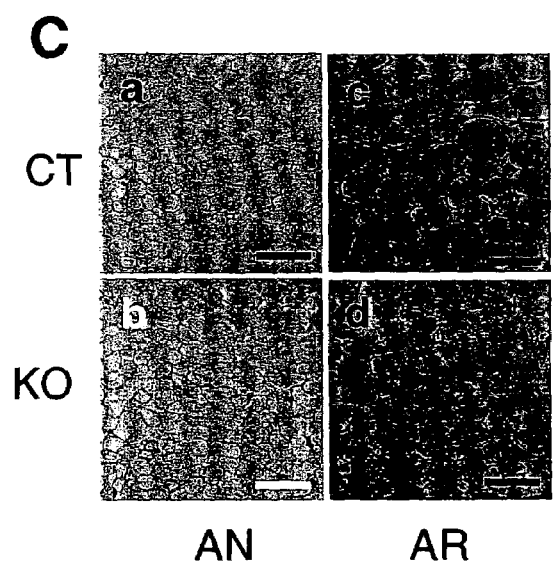
Figure 6D:
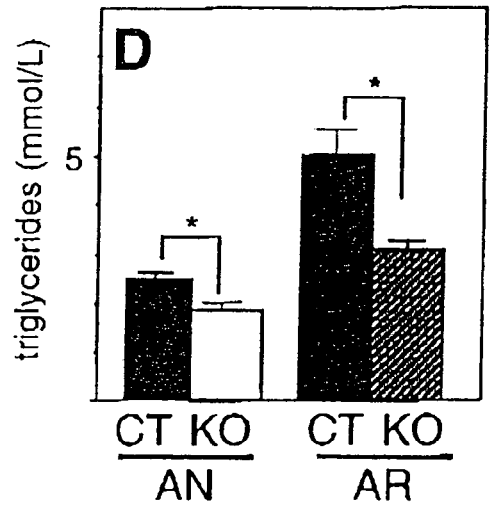
Figure 6E:
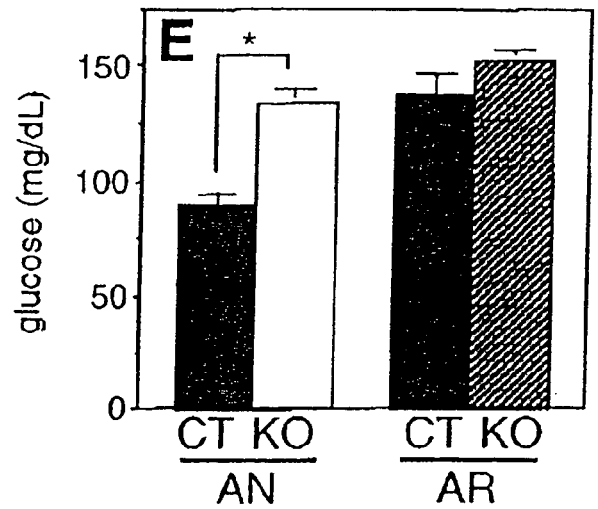
Figure 6F:
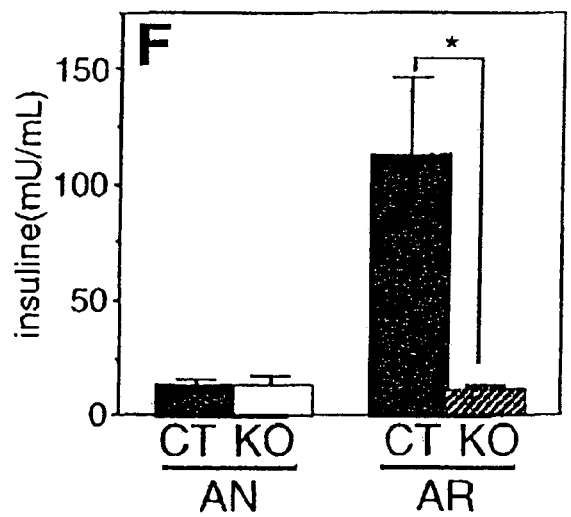

Analysis of the weight of the aP2-Cre-ER$^{T2(tg/0)}$/RXR$_\alpha^{L2/-}$ and aP2-Cre-ER$^{T2(tg/0)}$/RXR$_\alpha^{L2/+}$ animals treated with Tam (mutants; KO, and controls; CT, respectively) and fed with a normal diet (AN), determined for 30 weeks, revealed no significant difference between the two groups of animals (FIG. 6A). Furthermore, the weight of the adipose tissue and the morphology of the adipocytes were similar (FIGS. 6B and 6C). On the other hand, the glucose level was abnormally high and the triglyceride levels were lower in the mutant animals (FIG. 6D). By feeding the Tamoxifen-treated control animals with food rich in fat and in glucose (AR), they became obese (increase in the weight, the mass of adipose tissue and hypertrophy of the adipocytes) (FIGS. 6A–C). The triglyceride and insulin levels are also much higher than in the animals fed with AN. On the other hand, no increase in the weight of the animals and in the mass of the adipose tissue is observed in the mutated animals fed with AR. Furthermore, the adipocytes are not hypertrophic, and the triglyceride and insulin levels are similar to those observed with an AN.

These mutant animals therefore constitute advantageous models for studying obesity and diabetes, as well as for testing treatments of these diseases.

5) Fourth Example

Targeted Inactivation of the RXR$_\alpha$ Gene in Murine Hepatocytes

To carry out the spatiotemporally controlled site-specific mutagenesis in the liver, the inventors created transgenic mice called "αAT-Cre-ER$^T$" expressing the Cre-ER$^T$ fusion protein under the control of the promoter of the gene for human α-1-antitrypsin which is specifically active in the hepatocytes (Imaï et al.; 2000).

To inactivate RXR$_\alpha$ in the murine hepatocytes, the inventors constructed a mouse carrying floxed RXR$_\alpha^{L2}$ alleles (FIG. 1A) and used the transgenic mouse line αAT-Cre-ER$^T$ in which Tamoxifen (Tam) efficiently induces Cre-mediated recombination in the hepatocytes (FIG. 7). δAT-Cre-ER$^{T(tg/0)}$ mice which express Cre-ER$^T$ in about 50% of the hepatocytes (Imaï et al., 2000) were crossed with RXR$_\alpha^{L2/L2}$ mice so as to produce αAT-Cre-ER$^{T(tg/0)}$/RXR$_\alpha^{L2/L2}$ mice. Such three month old mice were treated with Tam (1 mg/day) five days, and the heart and the liver collected 7 days after the first injection of Tam (day 7), from one and three animals respectively. The heart and the liver were also collected from one and three animals, respectively, of the same genotype without treatment with Tam (day 0). The DNA was extracted from these tissues, and after digestion with BamHI, the RXR$_\alpha$ alleles were analyzed by southern blotting.

As expected, no excision is observed in the cells of the heart of mice treated with Tamoxifen (FIG. 7) or the liver of mice not treated with Tamoxifen (day 0). On the other hand, on day 7, the mice treated with Tamoxifen exhibit excision in the RXR$_\alpha$ gene in about 50% of the liver cells, which indeed corresponds to the expression, in the form of a mosaic, of the Cre-ER$^T$ protein in the hepatocytes of the αAT-Cre-ER$^T$ mouse.

On the other hand, 30 and 90 days after the treatment with Tamoxifen, practically no null RXR$_\alpha$ cells are again observed (FIG. 8). Furthermore, the RXR$_\alpha^{L-/L-}$ cells proliferate much less than the RXR$_\alpha^{L2/L2}$ cells after partial hepatectomy (HP) carried out on mutant animals treated with Tamoxifen (FIG. 8, compare lanes 68 and lanes 15–17). Thus, RXR$_\alpha$ is involved in the proliferation of the hepatocytes.

6) Fifth Example

The Chimeric Cre Recombinase Cre-ER$^{T3}$ is Ten Times more Sensitive to Tamoxifen than Cre-ER$^{T2}$ With the aim of increasing the sensitivity of the chimeric recombinase Cre-ER$^{T2}$ to Tam or OHT, the inventors replaced, in Cre-ER$^{T2}$, V400 with G (Cre-ER mutant M543A/L544A, called "Cre-ER$^{T3}$"). Transgenic mice expressing Cre-ER$^{T3}$ under the control of the K5-promoter were obtained, and a line expressing the chimeric recombinase at similar levels to those detected in the K5-Cre-ER$^T$ and K5-Cre-ER$^{T2}$ lines was generated (see FIG. 9, and results not presented).

The sensitivity to OHT was tested in a first instance by analyzing the intracellular location of the chimeric proteins. Whereas after treatment with 0.1 mg of OHT, Cre-ER$^{T2}$ and Cre-ER$^{T3}$ are both located in the cellular nuclei, Cre-ER$^{T3}$ is present in a larger fraction thereof at lower doses of Tam or OHT. At the dose of 0.001 mg, about ⅓ of the nuclei are strongly labeled with anti-Cre antibodies in the basal layer of the epidermis of K5-Cre-ER$^{T3}$ mice, whereas no positive nucleus is observed in the skin of K5-Cre-ER$^{T2}$ mice (FIG.

10). It was also possible to visualize this difference in sensitivity using the reporter mice RosaR26R (Rosa$^{fl/+}$) (Soriano, 1999). Indeed, although the excision levels induced with 1 and 0.1 mg of OHT are similar in both lines, the excision is markedly more efficient in the K5-Cre-R$^{T3}$ mice following treatments with 0.01 and 0.001 mg of OHT (FIG. 11). It should be noted that in the absence of treatment, no recombinase activity is detected in the K5-Cre-ER$^{T3}$ line.

7) Sixth Example

Role of RXRα in Skin Carcinogenesis

The stages of initiation, promotion, progression and tumor conversion in the skin carcinogenesis model are well characterised. In WT mice, initiation using 7,12-dimethylbenz (a) anthracene (DMBA) and promotion with 12-O-tetradecanoylphorbol 13-acetate (TPA) provokes papillomas that are hyperplastic, well-differentiated skin lesions. After a latency period of about 25 weeks, a percentage of papillomas progress to carcinoma (Ghadially and Ghadially, 1996; Hennings et al., 1993; klein-Szanto et al., 1989).

8–12 week-old K14-Cre-ER$^{T2(tg/0)}$/RXRα$^{L2/L2}$ mice were Tam-treated (0.1 mg per day for 5 days), which resulted in RXRα$^{ep-/-}$ mice (for epidermal keratinocyte-selective RXR$_α$ null genotype) fully lacking RXR$_α$ in keratinocytes of the epidermis and outer root sheath of the hair follicles 2 weeks after the first Tam injection. Similar Tam treatments applied to K14-Cre-ER$^{T2(tg/0)}$/RXRα$^{L2/+}$ and K14-Cre-ER$^{T2(0/0)}$/RXRα$^{L2/L2}$ littermates, resulted in control (CT) mice which carried, in epidermal keratinocytes, one WT (+) and one RXRα L– allele, and two RXRα L2 alleles, respectively.

To induce papilloma formation, CT and RXRα$^{ep-/-}$ female mice were topically-treated 16 days after the first Tam injection with a single dose of DMBA (50 µg), and then twice a week with TPA (5 µg) for 25–30 weeks (FIG. 12A). Seven to eight weeks after DMBA application, small papilloma were observed in all CT and RXRα$^{ep-/-}$ mice, and their number and size increased with time (FIG. 12B and data not shown). Interestingly, RXRα$^{ep-/-}$ mice developed approximately twice as many tumors as CT mice, and 30 weeks after the start of DMBA/TPA treatment, an average of 12 and 28 papillomas were present in CT and RXRα$^{ep-/-}$ mice, respectively (FIG. 12B). Although CT males were less sensitive to the DMBA/TPA treatment than CT females (the number of papillomas was two-fold lower), RXRα$^{ep-/-}$ males also exhibited about twice as many papilloma as CT males (data not shown). In both males and females, the size and growth rate of the tumors were increased in RXRα$^{ep-/-}$ mice (FIGS. 12C and 12D; and data not shown). After 30 weeks of TPA treatment, the papillomas of CT females were never longer than 12 mm, whereas ~10% of the papillomas of RXRα$^{ep-/-}$ females had a length between 12 and 16 mm, and 3% reached a length of 30–40 mm. Note that in the absence of either DMBA or TPA treatment no papilloma appeared in CT and RXRα$^{ep-/-}$ mice, even after 30 weeks of treatment (data not shown).

To characterize the tumors induced by DMBA/TPA treatment, ~50 tumors from 6 CT and 6 RXRα$^{ep-/-}$ mice were histologically examined. In agreement with previous reports, almost all tumors analysed 25 weeks after the start of DMBA/TPA treatment of CT mice were benign papillomas characterised by skin folds integrated by a core of connective tissue and lined by an acanthotic, hyperkeratotic, stratified squamous epithelium (FIGS. 13Aa and 13C (table)). 35% of the papillomas exhibited an atypical hyperplasia, 5% displayed an in situ carcinoma, but no focal carcinoma could be detected (FIGS. 13Ab and 13C (table), and data not shown). It was only 30 weeks after tumor initiation that some focal carcinoma were observed in ~16% of the tumors (FIGS. 13Ac and 13C (table), and data not shown). In contrast, 25 weeks after tumor initiation, almost all of the RXRα$^{ep-/-}$ papilloma exhibited an atypical hyperplasia, 10% displayed in situ carcinoma, and focal carcinoma were observed in 40% of the tumors (FIGS. 13Ba–c and 13C (table) and data not shown). Moreover, 5 weeks later, 27% of the tumors had progressed to differentiated and undifferentiated squamous cell carcinomas (SCC) with extensive local invasion of cancer cells in the dermis (FIGS. 13Bd–g and 13C (table)). Advanced grade I SCC (FIG. 13Bd, note the pearls with keratin in the center), grade II SCC (FIG. 13Be, note the fused keratin pearls, with only very reduced remaining regions of keratinization) and grade III and IV SCC (FIGS. 13Bf and g; note the spindle shape cytoplasm and, nucleus of the cancer cells that are found along with the muscle cells, indicating a complete conversion into malignant cancer) were observed in 3 to 9% of the tumors (FIG. 13C (table )). Highly aggressive spindle cell carcinoma (~6%) and basal cell carcinoma (~9%) were also found in RXRα$^{ep-/-}$, but not in CT animals (FIGS. 13Bh and i and 13C (table)).

Taken together, these above data show that higher incidence of malignant conversion occurred in papillomas of RXRα$^{ep-/-}$ than of CT mice.

Figure 14C:
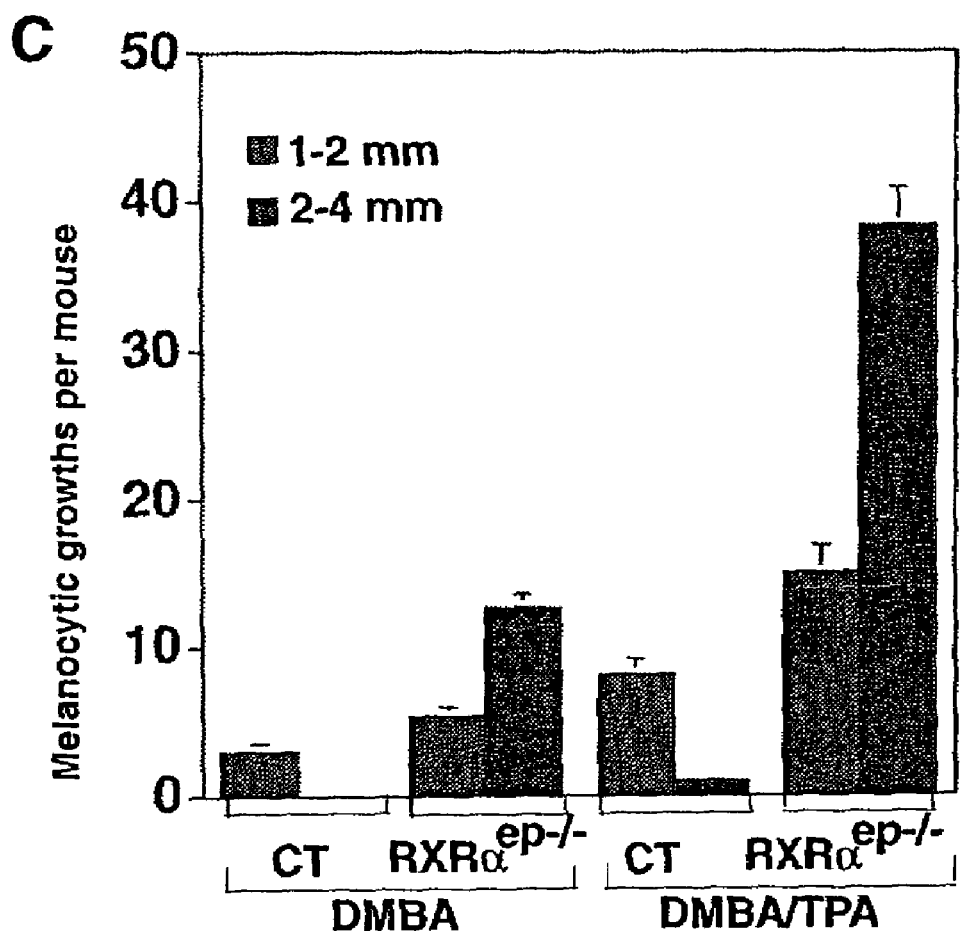

In agreement with previous reports (Epstein, 1992; Epstein et al., 1967 Husain et al., 1991), DMBA application to skin of CT mice induced on its own the formation of benign melanocytic growths (nevi) (FIG. 14A and data not shown), histologically characterized by subepidermal accumulation of melanocytes (Epstein et al., 1967). Interestingly, melanocytic growths were ~7-fold more efficiently induced by DMBA treatment of RXRα$^{ep-/-}$ mice (FIGS. 14A and B). Furthermore, these RXRα$^{ep-/-}$ melanocytic growths were generally larger (FIG. 14C) and contained a larger number of densely melanin-laden melanocytes in both the dermis and the hypodermis, and invasion or the underlying musculature was observed in 5–10% of them (data not shown), thus, indicating a higher potential of metastasis (Broome Powell et al., 1999; Epstein, 1967; Goding, 2000; Hirobe, 1995; Klein-Sozanto, 1989).

Electron microscopy revealed that melanocytes from CT nevi contained Mainly Stage III and IV melanosomes in agreement with previous reports. Most of the melanocytes present in melanocytic growths front RXRα$^{ep-/-}$ mice contained ~10-fold more melanosomes than CT melanocytes (data not shown). Moreover, in about 40% of the melanocytes, more than 30% of the granules had the appearance of vesicles of variable electron opacity with a distinct substructure (data not shown). The membrane of a number of melanosomes was disrupted and smaller melanin granules were scattered in the cellular matrix (data not shown). Taken together, these results indicate that DMBA induced melanoma formation in the skin of RXRα$^{ep-/-}$ mice.

Most interestingly, autopsies performed 30 weeks after DMBA treatment revealed that subiliac lymph nodes were enlarged and pigmented in two out of 4 RXRα$^{ep-/-}$ mice, but not in CT mice (0/4) (FIG. 15A a and b, and data not shown). Histological analysis revealed the presence in RXRα$^{ep-/-}$ mice, but not in CT mice, of few melanin-laden melanocytes in the lymphosinus of RXRα$^{ep-/-}$ mice, which were slightly enlarged (FIG. 14A). compare panel c and d, and data not shown). Multiple TPA applications after DMBA treatment increased the number of melanocytic growths in CT mice and RXRα$^{ep-/-}$ mice (FIG. 14B, and compare FIG. 12C and FIG. 14A). Whereas after 30 weeks of DMBA/TPA treatment, only about 10 nevi were observed per CT mouse (most of them having a diameter below 2 mm), more than 50 melanocytic growths were found per RXRα$^{ep-/-}$ mouse (more than 50% of them having a diameter over 2 mm) (FIG. 14 C). Melanocytes were found in 5/6 subiliac lymph nodes from RXRα$^{ep-/-}$ mice, and in 1/6 from CT mice (FIG. 15A e and f, and data not shown). DMBA/TPA treatments resulted in about 5 times more melanocytes in the lymphosinus of RXRα$^{ep-/-}$ 1 mice than after DMBA treatments. Most melanocyte-containing lymphosinus were markedly enlarged and clusters of melanocytes were seen in about 20% of them (FIG. 15h, and data not shown). In contrast, only few melanocytes were seen in only one of the lymph nodes of CT mice (data not shown).

As RXRα L2 alleles, but not L– alleles could not be detected in the RXRα$^{ep-/-}$ melanocytic tumors induced either by DMBA or DMBA and TPA, and L– but not L2 alleles in their epidermis (data not shown), these results demonstrate that the formation of melanoma in RXRα$^{ep-/-}$ mice is dependent on RXRα ablation in keratinocytes, but not in melanocytes.

8) Seventh Example

Role of RXRα in the Antitumoral Effect of Retinoic Acid

In agreement with previous results (Hansen, 2000; Huang et al., 1997; Leder et al, 1990; Slaga et al, 1980; Tennenbaum et al, 1998), topical application of all-trans retinoic acid (t-RA) efficiently blocked skin papilloma formation induced by DMBA/TPA in both female and male wild-type 129Sv (data not shown). RA application also efficiently inhibited tumor formation in CT, but not in RXRα$^{ep-/-}$ mice. Indeed, 25 weeks of RA treatment induced a reduction of size of the papilloma (from 2–3 mm to 1 mm, in 3 out of 8 papillomas of 6 mice) and the size remained the same in the other papillomas. In contrast, no decrease in size of the papilloma was observed in RXRα$^{ep-/-}$ mice. Furthermore, after ~25 weeks of DMBA/TPA treatment, an average of 1 tumor was observed in RA treated CT mice, whereas an average of ~17 tumors were found in similarly treated RXRα$^{ep-/-}$ mice. As previously observed in RXRα$^{ep-/-}$ mice in the absence of RA treatment, ~11% of the tumors were larger than 12 mm (data not shown), whereas the size of the tumors from CT mice was below 2 mm.

Furthermore, after RA treatment, both the number and size of melanocytic growths were increased in RXRα$^{ep-/-}$ mice compared to CT mice (data not shown).

REFERENCES

Akari et al. (1995) Proc. Natl. Acad. Sci. USA 92: 160–164.
Akagi et al. (1997) Nucleic Acids Res. 25: 1766–1773.
Arnheiter et al. (1990) Cell 62: 51.
Babinet (1995) Médecine/Sciences 11: 1154–1157.
Barbonis et al. (1993) Nucleic Acids Research, 21: 2025–2029.
Barettino et al. (1994) EMBO J. 13: 3039–3049.
Baur et al. (1996) EMBO J. 15: 110–124.
Beato (1989) Cell 56: 335–344.
Betz et al. (1996) Curr. Biol. 6: 1307–1316.
Bourguet et al. (1995) Nature 375: 377–382.
Brinster et al. (1982) Nature 296: 39–42.
Brocard et al. (1997) Proc. Natl. Acad. Sci. USA 94: 14559–14563.
Brocard et al. (1998) Nucleic Acids Res. 26: 4086–4090.
Broome Powell et al. (1999) Carcinogenesis 20: 1747–53.
Brown et al. (1987) Cell 49: 603–612.
Cadepond at al. (1997) Ann. Rev. Med. 48: 129–156.
Capecchi (1989) Science 244: 1288–1291.
Cavaillès et al. (1994) Proc. Natl. Acad. Sci. USA 91: 10009–10013.
Cavaillès et al. (1995) EMBO J. 14: 3741–3751.
Chambon (1996) FASEB J. 10: 940–954.
Danielian et al. (1992) EMBO J. 11: 1025–1033.
Denisen et al. (1995) Proc. Natl. Acad. Sci. USA, 92: 7376–7380.
Deuschle et al. (1990) Science 2: 480–483.
Diaz et al., (1999) JBC 274: 6634.
Durand et al. (1995) EMBO J. 13: 5370–5382.
Epstein et al. (1967) J Natl Cancer Inst 38: 19–30.
Epstein (1992) Photodermatol Photoimmunol Photomed 9: 91–8.
Evans (1988) Science 240: 889–895.
Feil et al. (1996) Proc. Natl. Acad. Sci USA 93: 10887–10890.
Feil et al. (1997) Biochemical and Biophysical Res. Com. 237: 752–757.
Figge al. (1988) Cell 52: 713–722.
Ghadially and Ghadially (1996) *Tumours of the skin*. IARC Sci Publ 126:1–43.
Goding (2000) *Melanocyte development and malignant melanoma*. Forum (Genova) 10 (3): 176–87.
Gossen et al. (1992) Proc. Natl. Acad. Sci. USA 89: 5547–5551.
Green and Chambon (1988) Trends Genetics 4: 309–314.
Gronemeyer (1991) Ann. Rev. Genet. 25: 89–123.
Gu et al. (1993) Cell 73: 1155–1164.
Halachmi et al. (1994) Science 264: 1455–1458.
Hansen et al (2000) Cracinogenesis 21: 1271–1279.
Hennings et al. (1993) Proc Soc Exp Biol Med 202: 1–8.
Hirobe (1995) Histol. Histopathol. 10: 223–37.
Hu et al. (1987) Cell 48: 555–556.
Huang et al. (1997) Proc. Natl. Acad. Sci USA 94: 5826–30.
Hug et al. (1990) Mol. Cell. Biol. 8: 3065.
Husain et al (1991) Cancer Res 51(18) :4964–70.
Hynes et al. (1981) Proc. Natl. Acad. Sci. USA 78: 2038–2042.
Imaï et al. (2000) Genesis 26: 147–148.
Indra et al. (1999) Nucl. Acid. Res. 27: 4324–4327.
Israel et al. (1989) Nucleic Acids Res. 17: 2589–2604).
Jackson et al., (1993) EMBO J. 12: 2809–2819.
Jaenisch (1988) Science 240: 1468–1474.
Kastner at al. (1994) Cell 78: 987–1003.
Kastner et al. (1996) Gene Dev. 10: 80–92. 67.
Kellendonk et al. (1996) Nucleic Acids. Res. 24: 1404–1411.
Kellendonk et al. (1999) J. Mol. Biol. 285: 175–182.
Kilby et al. (1993) TIG 9: 413–421.
Klein-Szanto et al. (1989) Carcinogenesis 10:2169–72.
Klock et al. (1987) Nature 329: 734–736.
Kühn et al. (1995) Science 269: 1427–1429.
Labow et al. (1990) Mol. Cell. Biol. 10: 3343–3356.
Lakso et al. (1992) Proc. Natl. Acad. Sci USA 89: 6232–6236.
Leder et al. (1990) Proc. Natl. Acad. Sci. USA 87:9176–82.
Ledouarin B. et al. (1995) EMBO J. 14: 2020–2033.
Lee et al. (1981) Nature 294: 228–232.
Lee et al. (1995) Nature 374: 91–94.
Leng et al. (1995) Mol. Cell. Biol. 15: 255–263.
Li et al. (1997) Proc. Natl. Acad. Sci USA 94: 9831–9835.
Li et al: (1998) Endrocrinology 139: 4391–4396).
Littlewood et al. (1995) Nucleic Acids Res. 23: 1686–1690.

Lobe et al. (1999) Dev. Biol. 208: 281–292.
Logie et al. (1995) Proc. Natl. Acad. Sci. USA 92: 5940–5944.
Mahfoudi et al. (1995) Proc. Natl. Acad. Sci. USA 92: 4206–4210.
Mao et al. (1995) Proc. Natl. Acad. Sci. USA 96: 5037–5042.
Mascrez et al. (1998) Development 125: 4691–4707.
Mayo et al. (1902) Cell 29: 99–108.
Metzger et al. (1995) Proc. Natl. Acad. Sci. USA 92: 6991–6995.
Metzger and Chambon (2001), Methods, in press.
Metzger and Feil (1999), Curr. Opin. Biotechnol. 5: 470–476.
Nover et al. (1991) in "Heat Shock Response", e.d.
Nover, L CRC, Boca Raton, Fla. pp, 167–220.
Orban et al. (1992) Proc. Natl. Acad. Sci USA 89: 6861–6865.
Parker (1993) Curr. Opin Cell. Biol, 5: 499–504.
Peters et al. (1997) J. Biol. Chem 272: 27307–27312.
Picard et al. (1994) Curr. Opin. Biotechnol. 5: 511–515.
Porter et al. (1998) J. Invent. Dermatol. 110: 951–957.
Rajewsky et al. (1996) J. Clin. Invest. 98: 600–603.
Reichrath et al. (1994) Brit. J. Dermatol. 131: 477–482.
Renaud et al. (1995) Nature 378: 681–689.
Ross et al. (1990) Proc. Natl. Acad. Sci USA 87: 9590–9594.
Saatcioglu et al. (1993) Mol. Cell. Biol. 13: 3675–3685.
St-Onge et al. (1996) Nucleic Acids Res. 24: 3875–3877.
Saitou et al. (1995) Nature 374: 159–162.
Sambrook et al. (198) Molecular cloning: a laboratory manual second edition—Cold Spring Harbor Laboratory Press. Cold Spring Harbor, N.Y., USA
Sauer (1994) Current opinion in Biotechnology 5: 521–527.
Sauer et al. (1990) The New Biologist 2: 441–449.
Sauer B. (1998) Methods 14 381–392.
Schmedt et al. (1998) Nature 394: 901–904.
Schmidt et al. (1990) Mol. Cell. Biol. 10: 4406–4411.
Schwenk et al. (1998) Nucleic Acids Res. 26: 1427–1432.
Seark et al. (1995) Mol. Cell. Biol. 5: 1480–1489.
Shaikh and Sadowski (2000) J. Mol. Biol. 302: 27–48.
Simons (1994) New York, Vitam. Horm. 49: 49–130.
Slaga et al. (1980) Proc Natl Acad Sci USA 77(4):2251–4.
Soriano (1999) Nature Genet 21: 70–71.
Sternberg et al. (1986) J. Mol. Biol. 187: 197–212.
Sumi-Chinose et al. (1997) Mol. Cell. Biology 17, 5976–5986.
Sundberg et al. (1996) Dermatol. 7: 249–267.
Tennenbaum et al. (1998) Cancer Res 58(7): 1435–43.
Vassar et al. (1989) Proc. Natl. Acad. Sci. USA, 86: 1563–1567.
Wang et al. (1997) Proc. Natl. Acad. Sci. USA 94: 219–226.
Wendling et al. (1999) Proc. Natl. Acad. Sci. USA 96: 547–551.
Wurtz et al. (1996) Natural Structural Biology 3: 87–93.
Yoshizawa et al. (1997) Nature Genet. 16: 391–396.
Zechel et al. (1994) EMBO J. 13: 1425–1433.
Zhang et al. (1996) Nucleic Acids Res. 24: 543–548.

The invention claimed is:

1. A method for producing spatio-temporally-controlled site-specific somatic recombinations in a mouse, wherein one or more gene or intergenic DNA sequences of interest naturally belonging to the genome of said mouse have been recombined, comprising:
   a) obtaining a transgenic mouse, wherein said transgenic mouse comprises a transgene encoding:
      (i) a Cre fusion protein comprising sequentially:
         (1) a Cre recombinase protein;
         a hinge region of at least 15 amino acids;
         a polypeptide comprising the ligand binding domain of the human nuclear estrogen receptor, or of a vertebrate nuclear estrogen receptor, said polypeptide exhibiting at least one mutation relative to the wild-type form of said ligand binding domains; and
         (2) said Cre fusion protein has a negligible, or even zero recombinase activity in the absence of a synthetic ligand endowed with antiestrogenic activity, the recombinase activity being induced by low dose of the synthetic ligand;
      (ii) one or more gene or intergenic DNA sequences of interest, naturally belonging to the mouse genome, flanked by one or more recognition sites for a Cre recombinase protein,
   b) administering to said transgenic mouse a low dose of said synthetic ligand in order to induce Cre-mediated recombination; and
   c) said gene or intergenic DNA sequences of interest undergo a site specific somatic recombination, as a result of the induction by said synthetic ligand, in at least 90% of the targeted cells of said mouse, whereas said gene or intergenic sequences of interest underwent recombination in less than 5% of the targeted cells of said mouse before step b).

2. The method of claim 1, wherein said one or more sites of recognition specific for said Cre recombinase protein comprise the sequences Lox P.

3. The method of claim 1, wherein said hinge region comprises all or part of the D hinge region of a nuclear estrogen receptor.

4. The method of claim 3, wherein said hinge region comprises amino acids 282 to 301 of the sequence of SEQ ID NO. 2.

5. The method of claim 1, wherein said polypeptide chosen from the ligand-binding domain of the nuclear human estrogen receptors is the ligand-binding domain of the human nuclear estrogen receptor α and wherein said ligand-binding domain exhibits at least the following mutations:
   mutation (G400V) glycine to valine at position 400 of the sequence SEQ ID No. 2; and
   mutation (methionine-leucine) to (alanine-alanine) situated at position 543–544 (M543A/L544A mutation) of the sequence SEQ ID No. 2.

6. The method of claim 1, wherein said transgene is under the control of expression elements ensuring its expression in the targeted cells of said mouse.

7. The method of claim 6, wherein said expression elements are chosen from elements controlling tissue-specific and cell-specific expression or ubiquitous expression.

8. The method of claim 6, wherein said expression elements controlling expression are chosen from elements controlling expression ensuring constitutive expression or elements controlling expression ensuring inducible expression.

9. The method of claim 6, wherein said expression element is chosen from the group composed of the promoter regions of cytokeratin 14 (K 14), of cytokeratin 5 (K 5), and of the adipocyte fatty acid binding protein 2 (aP2).

10. The method of claim 6, wherein said transgene has the sequence SEQ ID NO:5, which encodes the fusion protein Cre-ERT$^{T2}$ having the sequence SEQ ID NO:6.

11. The method of claim 1, wherein said DNA sequence of interest comprises the RXRα gene.

12. The method of claim 1, wherein the genome of said mouse comprises:
   a transgene encoding the fusion Cre-ERT$^{T2}$ having the sequence SEQ ID NO:6, said fusion protein being selectively expressed in adipocytes under the control of the adipocyte fatty acid binding protein 2 (aP2) promoter; and
   one or more chromosomal DNA sequence of interest in their natural chromatin context and flanked on each sided by one lox site, the two lox sites being oriented as a direct repeat.

13. The method of claim 1, wherein the synthetic ligand endowed with antiestrogenic activity is selected from the group consisting of Tamoxifen, 4-hydroxyTamoxifen, ICI 164 384 and ICI 182 780.

14. The method of claim 13, wherein the synthetic ligand endowed with antiestrogenic activity is Tamoxifen or 4-hydroxyTamoxifen.

* * * * *